US012673031B2

(12) United States Patent
Hsieh et al.

(10) Patent No.: US 12,673,031 B2
(45) Date of Patent: Jul. 7, 2026

(54) SOY PROTEINS FOR PREPARATION OF GELS, FIBERS AND FILMS

(71) Applicant: The Regents of the University of California, Oakland, CA (US)

(72) Inventors: You-Lo Hsieh, Oakland, CA (US); Xingchen Liu, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 1105 days.

(21) Appl. No.: 17/765,386

(22) PCT Filed: Oct. 1, 2020

(86) PCT No.: PCT/US2020/053754
§ 371 (c)(1),
(2) Date: Mar. 30, 2022

(87) PCT Pub. No.: WO2021/067568
PCT Pub. Date: Apr. 8, 2021

(65) Prior Publication Data
US 2022/0378713 A1      Dec. 1, 2022

Related U.S. Application Data

(60) Provisional application No. 62/908,826, filed on Oct. 1, 2019.

(51) Int. Cl.
| | |
|---|---|
| *A23D 7/005* | (2006.01) |
| *A23J 3/16* | (2006.01) |
| *A23J 3/28* | (2006.01) |
| *A61K 9/70* | (2006.01) |
| *A61K 31/5415* | (2006.01) |
| *A61K 47/42* | (2017.01) |
| *B01D 67/00* | (2006.01) |
| *B01D 71/74* | (2006.01) |

(52) U.S. Cl.
CPC .......... *A61K 9/7007* (2013.01); *A23D 7/0053* (2013.01); *A23J 3/16* (2013.01); *A23J 3/28* (2013.01); *A61K 31/5415* (2013.01); *A61K 47/42* (2013.01); *B01D 67/0004* (2013.01); *B01D 67/0083* (2013.01); *B01D 71/74*

(2013.01); *B01D 2323/081* (2022.08); *B01D 2323/12* (2013.01); *B01D 2323/39* (2013.01)

(58) Field of Classification Search
None
See application file for complete search history.

(56) References Cited

U.S. PATENT DOCUMENTS

| | | | | |
|---|---|---|---|---|
| 2003/0134918 A1* | 7/2003 | Ko | .......................... | A61K 31/65 |
| | | | | 521/50 |
| 2012/0027838 A1 | 2/2012 | Gordon et al. | | |
| 2014/0235737 A1 | 8/2014 | Parker et al. | | |
| 2015/0101979 A1 | 4/2015 | Joo et al. | | |
| 2018/0207232 A1* | 7/2018 | Lelkes | .................. | A61L 27/227 |

FOREIGN PATENT DOCUMENTS

| | | | |
|---|---|---|---|
| KR | 19990040616 A | * | 6/1999 |

OTHER PUBLICATIONS

Translation of KangHo et al. KR19990040616A. Published Jun. 5, 1999. Google Patents [online]. [retrieved on Mar. 4, 2026]. Retrieved from the Internet: <https://patents.google.com/patent/KR19990040616A/en?oq=1999-0040616> (Year: 1999).*

Feng J, Wang J, Li X, Li H, Chen H, Liu X, Linoleic acid and heat synergistically promote the aggregation of soybean proteins and the preliminary study of molecular interaction, LWT, vol. 223, Published 2025, p. 117710, <https://doi.org/10.1016/j.lwt.2025.117710> (Year: 2025).*

Wang et al. "Preparation of Alginate/Soy Protein Isolate Blend Fibers Through a Novel Coagulating Bath", Journal of Applied Polymer Science, 2006, 101(1), 425-431.

International Search Report and Written Opinion for PCT/US2020/53754, mailed Feb. 9, 2021, 10 pages.

* cited by examiner

*Primary Examiner* — Ali Soroush
*Assistant Examiner* — Afua Bamfoaa Boateng
(74) *Attorney, Agent, or Firm* — Mintz Levin Cohn Ferris Glovsky and Popeo, P.C.

(57) ABSTRACT

The present invention provides compositions of soy protein gel fibers, soy protein fiber membranes, and soy protein films. The present invention also provides methods of making the soy protein compositions and also uses of the compositions.

9 Claims, 27 Drawing Sheets

*Cut*

*As is*          *Squeezed*

$$y = -1.30x + 70.62$$
$$R^2 = 0.97$$

As-spun:
pH 7, 14 d

*-38.3 %*

2 μm

Genipin:
pH 7, 14 d

*-21.5 %*

2 μm

Heated:
pH 7, 14 d

276.9 ± 35.8 nm

*-5.6 %*

2 μm

Heated:
pH 0, 2 d

*-10.4 %*

3 μm

Heated:
pH 10, 2 d

*-8.9 %*

3 μm

Heated:
100 °C, pH 7, 2 h

*-12.4 %*

3 μm

| Samples | XRD | | FTIR-ATR | | |
|---|---|---|---|---|---|
| | α | β | α | β-Turn | β-Sheet |
| FD SPs | 14 | 16 | 37 | 14 | 28 |
| #1 (21 °C) | 37 | 7 | 26 | 25 | 33 |
| #2 (21 °C, vacuum) | 36 | 12 | 25 | 28 | 26 |
| #3 (21 °C, vacuum, moisture) | 43 | 5 | 28 | 23 | 34 |
| #4 (65 °C) | 29 | 23 | 33 | 16 | 40 |
| #5 (65 °C, vacuum, moisture) | 30 | 23 | 22 | 16 | 48 |
*FIG. 14C*
*FIG. 14D*
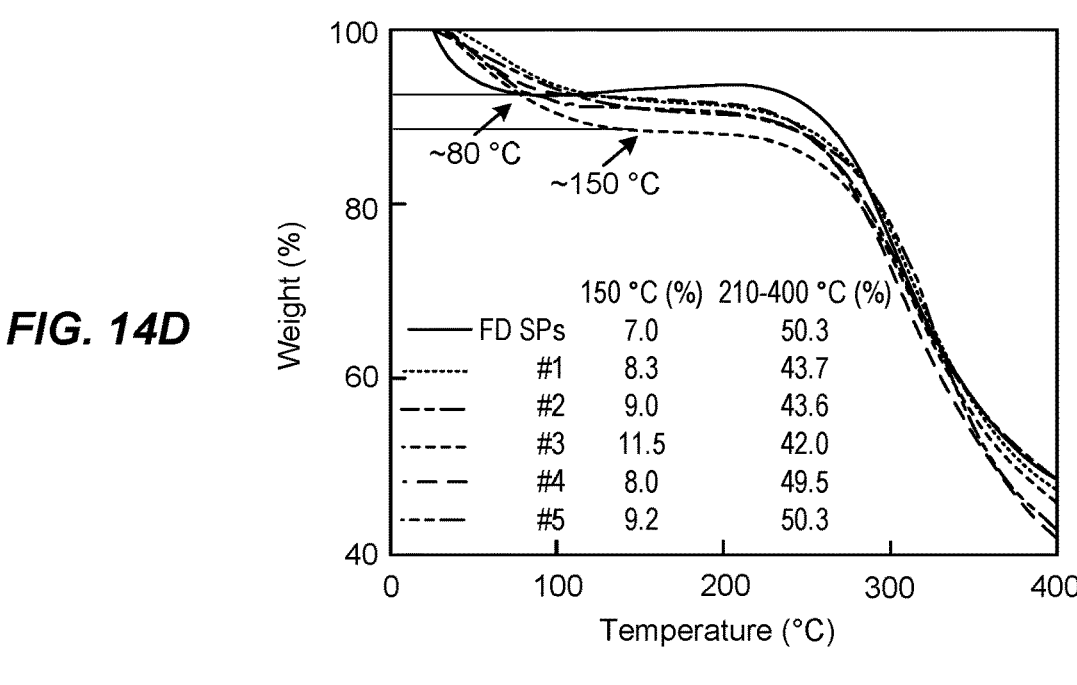
*FIG. 14E*
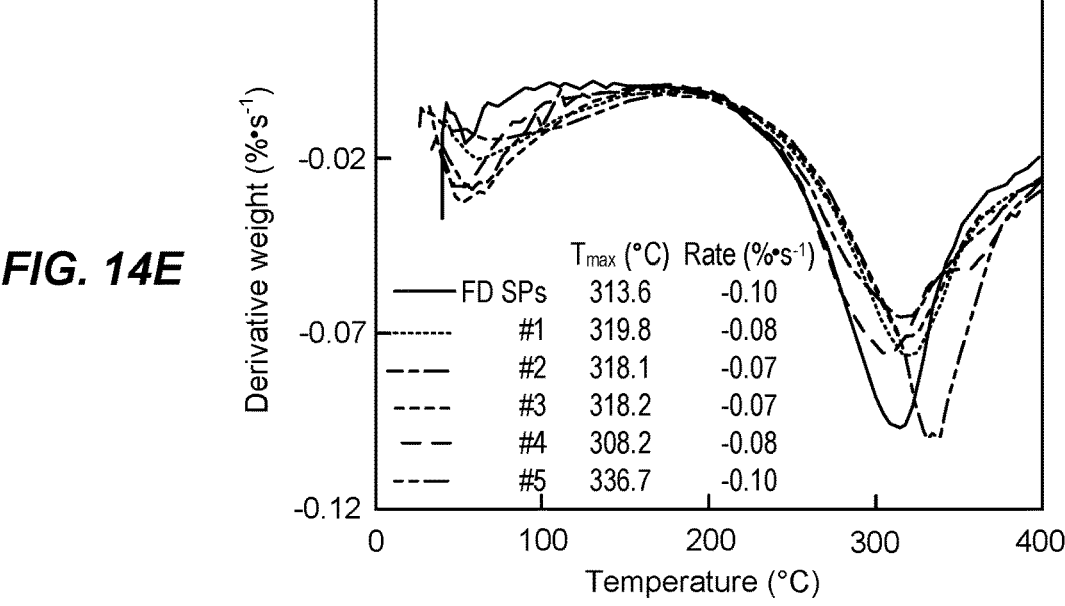

SOY PROTEINS FOR PREPARATION OF GELS, FIBERS AND FILMS

CROSS-REFERENCES TO RELATED APPLICATIONS

This application claims priority to U.S. Provisional Application No. 62/908,826 filed Oct. 1, 2019, which is incorporated herein in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. 2014-38502-22598 awarded by the U.S. Department of Agriculture (USDA). The Government has certain rights in the invention.

BACKGROUND OF THE INVENTION

Soy proteins (SPs) are abundant plant proteins that could be readily derived from the major byproduct of the largest edible oil and biodiesel industry in the United States. They are a heterogeneous mixture of globular proteins with distinct amino acid (AA) compositions, approximately overall 47.5 mol % polar and 52.5 mol % nonpolar ones. Meanwhile, such valuable and intrinsic amphiphilic features also enable them to be processed into high-performance functional materials. It has been shown that nearly all SPs (97.7%) in soy protein isolates (SPI) could be converted into homogeneous aqueous soy protein colloids (SPC) at up to 9% by simply blending with high mechanical shear force (30 k rpm, 15 min). Such colloids were amphiphilic, lowering water surface tension to 41.2 mN/m at above 0.98% concentration at which micelle-like structures formed. SPCs could also form 1D and 2D ordered fibrous structures via isotropic ice-templating and lyophilization. Interestingly, 2D laminated fibrous assemblies could be disassembled into amphiphilic soy protein microfibrils (SPMF) that were compatible with both polar and nonpolar solvents and facilely emulsify 90 v/v % hexadecane. So far, very few SP Pickering emulsifiers (mainly particles) have been reported, none has shown comparable emulsifying capability. Although surface-active properties (i.e. adsorption at the air-water interface and foaming behavior) of soy glycinin amyloid-like fibrils were recognized, they have not been explored as Pickering emulsifiers yet.

High internal phase emulsions (HIPEs, >74 v/v % internal phase) typically exhibit viscoelastic behavior and even turn into soft gels with the increasing of the internal phase due to the deformation of droplets and their dynamic displacement when subjected to a shear strain. Pickering emulsions particularly have superior stability because Pickering emulsifiers could irreversibly adsorb at the interface of two immiscible liquids. In the case of Pickering HIPEs, delicate synthesis or surface modification, additional additives and high-energy input are generally necessary to achieve the satisfactory intermediate wettability of Pickering emulsifiers. Pickering HIPEs have been studied for emulsion polymerization, enhanced oil recovery, catalyst recycling, and controlled release applications. Emulsion electrospinning has been explored to generate core-sheath gel fibers, where core is the dispersed phase and sheath is the continuous phase of emulsion. So far, the majority of Pickering emulsifiers are inorganics or derived from synthetic polymers, thus mostly nondegradable. Therefore, bio-based polymers, such as polysaccharides and proteins (ex. soy proteins), are more ideal resources for large-scale food, cosmetic and biomedical applications due to their environmental compatibility and biodegradability.

Further, soy proteins can be utilized to form membranes for filtering and recovery of compounds such as dyes. The increasing and cumulative presence of dyes from industrial effluents in our water ways has posed serious toxicity to aquatic ecosystems and human health. To remove dyes, activated carbon particulates and biosorbents derived from agricultural byproducts are among the most widely studied, however, also generate concentrated sludges as secondary pollutants that still require safe disposal and/or costly recycling. Polymeric adsorbents with tailored morphologies and adsorption and desorption properties that are capable of controlled separation and regeneration of valuable dyes are particularly appealing. Either negatively or positively charged synthetic and natural polyelectrolytes have been processed into adsorbents for selectively adsorbing either cationic or anionic dyes. The pH-responsive absorbents have only been derived from synthetic polyampholytes and polymer mixtures with various chemical modification and/or polymerization. None has been generated from natural polymers or polyampholytes, i.e. proteins, especially in the form of ultra-fine fibers.

Soy proteins (SPs) are mixtures of large and complex globular proteins with ca. 47 mol % amino acids containing strongly polar side groups, i.e., 20.5 mol % —COOH and 18.0 mol % —NH$_2$, thus natural polyampholytes. SPs are also readily available, being the vastly under-utilized byproducts of the largest edible oil and biodiesel production in the United States. Fibrous adsorbents, especially those with finer diameters, are desirable for their higher specific surface. However, spinning these complex and large globular SPs into fibers has been challenging in comparison to fibrous proteins, such as collagen and silk fibroin. To electrospin SPs, SPs must be denatured and hydrolyzed using heat (40-90° C., 40 min-8 d) and/or alkali (pH 12)) to disperse SPs in organic or aq. media first, then with the addition of polymer carriers, such as polyethylene oxide (PEO, 400-900 kDa at 10 w/w % or 200 kDa at 33 w/w %) and polyvinyl alcohol (PVA, 78 or 100 kDa at 50 w/w %), and/or surfactants (i.e. 0.5 or 1% Triton X-100 and 17.5% sodium dodecyl sulfate).

A green and facile process to overcome the processing challenges was developed to fabricate amphoteric SP polyelectrolytes into high specific surface fibrous membranes by electrospinning. To avoid using any chemical additives and treatments, electrospinning of aqueous SP colloids will be aided by hybridizing with fiber-forming PVA, then stabilized by crosslinking. Chemical crosslinking involve the use of a naturally occurring and biocompatible genipin that is 5,000-10,000 times less cytotoxic than glutaraldehyde and has shown to crosslink electrospun chitosan (21° C., 1 d) and gelatin (21° C., 7 d) fibers. Alternatively, heat induced self-condensation of amino acid side groups (105-180° C., 24-120 h) that had demonstrated to render electrospun collagen and gelatin fibers water-insoluble. The effects of crosslinking with genipin reactions and heat treatments were systematically evaluated by aqueous solubility and resiliency as well as the secondary structure of SPs, crystalline domains, chemical changes, and thermal behaviors. The pH-tunable amphoteric characteristics of the optimally crosslinked membranes were elucidated by their selective adsorption of cationic and anionic dyes as well as the adsorption isotherm and kinetics, and cyclic adsorption/desorption for dye recovery, fibrous membrane regeneration and reuse.

Soy protein fibers can also be used to fabricate biocompatible and non-toxic films which are pH responsive, making them useful for processes such as controlled drug delivery. pH-Responsive polymers are polyelectrolytes that own weak acidic or basic functional groups (i.e. carboxyl, pyridine, sulfonic, phosphate, and amine) that would either accept or release protons in response to a change in the environmental pH. Different organs, tissues and cellular compartments are known to have large differences in pH, such as the transition from the acidic (pH=2) environment in the stomach to the basic one in the intestine (pH=5-8), which makes the pH a practical and suitable stimulus for the drug/nutrient delivery. Therefore, pH-responsive polymers with a tolerable toxicity have been extensively studied within the setting of biological conditions. A current trend in this field is to adopt more bio-based polymers owing to their abundance, biodegradability and biocompatibility to reduce the toxicity. Cationic or anionic polyelectrolytes would only show the pH or electrical response in a specific and narrow pH range around their pKa. Recently, amphoteric membranes have been reported by using the mixture of cationic and anionic polysaccharides, i.e. chitosan and carboxymethylcellulose, and chitosan and carboxymethylchitosan. SPs fully denatured in 6 M guanidine hydrochloride have also been converted into pH- and electric-responsive hydrogel membranes at pH 2-12. However, acutely toxic chemical crosslinkers, such as glutaraldehyde and epichlorohydrin that mainly react with primary amine and/or carboxylic acid groups, have been applied in all above cases to improve the integrity of substrates in harsh aqueous media. This is against the original intension to pursue the biocompatibility and tolerate toxicity, thus may potentially limit their practical applications.

Like many other plant-based proteins (i.e. buckwheat seeds, rice, and pea), SPs have also been earlier confirmed to be β-type proteins by circular dichroism, meaning that they prefer to adopt the β domains, especially β-sheets, the most stable secondary structures that known to be water-insoluble and correlated to the superior mechanical performance of spider silk proteins. It is useful to induce the secondary structural transition of SPs towards the formation of more β-sheets to render the whole matrix water-insoluble without requiring any extra physical or chemical crosslinking.

Semi-crystalline SP microfibrils were selectively disassembled from the laminated fibrous products generated through the ice-templated self-assembly. They are amphiphilic and could be homogeneously dispersed in both polar (i.e. water, dimethylformamide, alcohols and acetone) and nonpolar solvents (i.e. toluene and chloroform), thus allowing a flexible processing environment. SP microfibril dispersions in ethanol (EtOH) were cast on either hydrophobic or hydrophilic substrates under different drying temperature and humidity to investigate how they may influence the secondary structure composition of SPs to render the films insoluble in aq. media and whether amphiphilic and amphoteric characteristics of SPs could be reflected in the final films. Surface morphology and wettability, moisture regain, and pH-responsive swelling behaviors of films were thoroughly studied. Cationic methylene blue (MB) has been selected as the model compound in this study. In addition to serve as active ingredients in pharmaceutical preparations, it is also a promising photosensitizer for catalysis, photodynamic therapy and wound healing, possessing a high quantum yield of $O_2$ generation with the excitation in the therapeutic window (600-900 nm). Its immobilization on a solid matrix is particularly favored because it helps avoid being reduced into the inactive leukomethylene blue after following systemic administration. MB at 0.8 mM has been earlier found to be facilely bound to SP microfibrils with the efficiency of 94.1% by directly and homogeneously dispersing it in colloids. Such MB-bound microfibrils were converted into films under the optimal condition and used for the controlled release study in vitro.

BRIEF SUMMARY OF THE INVENTION

In one embodiment, the present invention provides a gel fiber composition comprising: a soy protein colloid (SPC) or soy protein microfibril (SPMF); sodium alginate (SA); and a hydrocarbon solvent or soy oil.

In another embodiment, the present invention provides a method for preparing the gel fiber of the present invention, the method comprising: (a) forming a reaction mixture comprising a soy protein colloid (SPC) or soy protein microfibril (SPMF), sodium alginate (SA), and a hydrocarbon solvent or soy oil; and (b) spinning the reaction mixture into a CaCl₂ aqueous solution, thereby forming the gel fiber.

In another embodiment, the present invention provides a soy protein fiber membrane comprising: a soy protein colloid (SPC) or a soy protein microfibril (SPMF); and polyvinyl alcohol (PVA), wherein the soy protein fiber membrane is substantially water-insoluble.

In another embodiment, the present invention provides a method for preparing the soy protein fiber membrane of the present invention, the method comprising: (a) forming a reaction mixture comprising a soy protein colloid (SPC) or soy protein microfibril (SPMF), and polyvinyl alcohol (PVA); (b) electrospinning the reaction mixture into fibers; and (c) heat treating the fibers at a temperature of at least 100° C., thereby forming the soy protein membrane.

In another embodiment, the present invention provides a soy protein film comprising a soy protein colloid (SPC) or soy protein microfibril (SPMF), wherein the secondary structures of the SPC or SPMF comprises at least 40% β-sheets, and wherein the soy protein film is substantially water-insoluble.

In another embodiment, the present invention provides a method for selectively delivering a drug, the method comprising administering to a subject in need thereof, an effective amount of the soy protein film of the present invention, wherein the soy protein film further comprises a drug.

BRIEF DESCRIPTION OF THE DRAWINGS

FIG. 2A-2B show AFM height images of SPC on mica. FIG. 2C shows the optical microscopic image of SPMF on mica. FIG. 2D shows water droplets with contact angle denoted.

FIGS. 4A-4C show as-spun with the reverted spinning mixture insetted in FIG. 4A. FIG. 4D-4E show images after air-dried for 1 d. Phase contrast and black balance adjustment were applied in FIG. 4C and FIG. 4E.

Figure 5A:
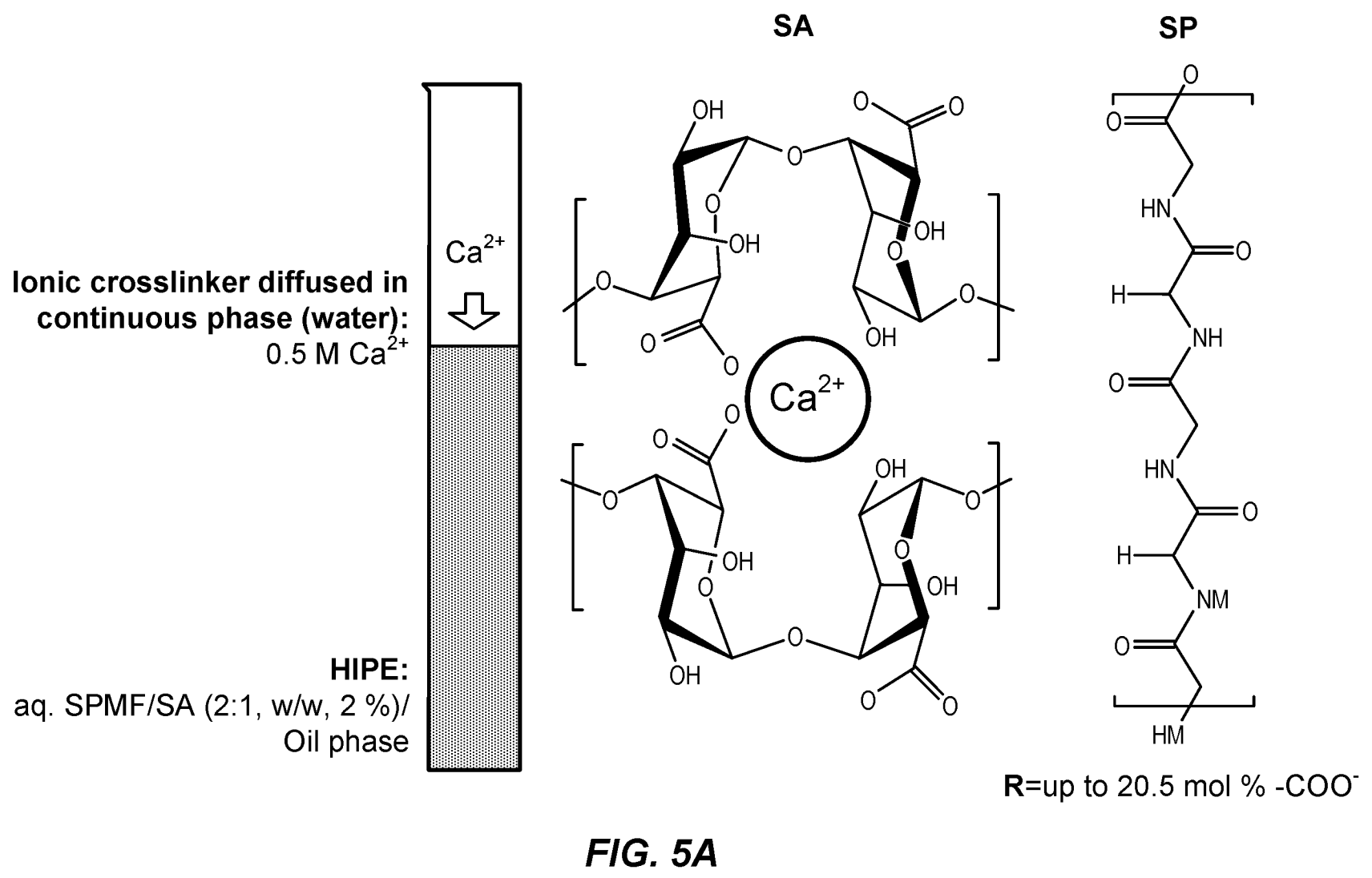

FIGS. 5A-5C show HIPE gels, 10/90 v/v aq. SPMF/SA (2:1, w/w, 2%)/oil phase. FIG. 5A shows a diagram for gel crosslinking mechanism. FIG. 5B shows hexadecane, gels in different morphologies, as is, cut or squeezed. FIG. 5C shows cyclohexane, mass loss in fume hood at ambient temperature.

FIG. 6A shows as-spun 7:3 SPC/PVA. FIG. 6B shows as-spun 9:1 SPC/PVA. FIG. 6C shows genipin-reacted (65° C., 1 h) and lyophilized 7:3 SPC/PVA. FIG. 6D shows heated (150° C., 12 h) 7:3 SPC/PVA. Photograph of membrane is shown as inset in each.

FIG. 7A shows FTIR-ATR spectra. FIG. 7B shows DSC. FIG. 7C shows TGA.

FIG. 8A shows as-spun SPC/PVA. FIG. 8B shows genipin-crosslinked (65° C., 1 h) SPC/PVA. FIGS. 8C-8F show heated (150° C., 12 h) SPC/PVA. Mass loss values in % (N=3) are denoted.

FIG. 9A shows photographs of as is, wet, and air-dried (AD) membranes. FIG. 9B shows K/S values with color strength denoted in parenthesis. FIGS. 9C-9D show SEM images of AD genipin-crosslinked and heated membranes.

FIG. 10A shows aqueous MB and CBY (500 mg/L), and Sudan IV in hexadecane (50 mg/L) with the average water CA denoted (N=5). Adsorption of MB (blue) and CBY (orange) at 1 mg/mL membrane to solution ratio over time: at pH 7 (FIG. 10B) and at pH 2 (FIG. 10C).

FIG. 11A shows 5 repetitive MB (20 mg/L) adsorption (pH 7) and desorption (pH 2) cycles. FIG. 11B shows photographs and SEM images of membranes after the fifth cycle. FIG. 11C shows images and UV-vis spectra of MB/MO mixture (1:1, 20 mg/L) before and after selective adsorption of MB at pH 7. FIG. 11D shows UV-vis spectra of MO at pH 2.

FIGS. 14A-14D show XRD patterns (FIG. 14A), amide I peak by FTIR-ATR (FIG. 14B) and the derived secondary structure composition (FIG. 14C), TGA (FIG. 14D) and DTA (FIG. 14E) of FD SPs and films: #1 (21° C.); #2 (21° C., vacuum); #3 (21° C., vacuum, moisture); #4 (65° C.); #5 (65° C., vacuum, moisture).

DETAILED DESCRIPTION OF THE INVENTION

I. General

Figure 1A:
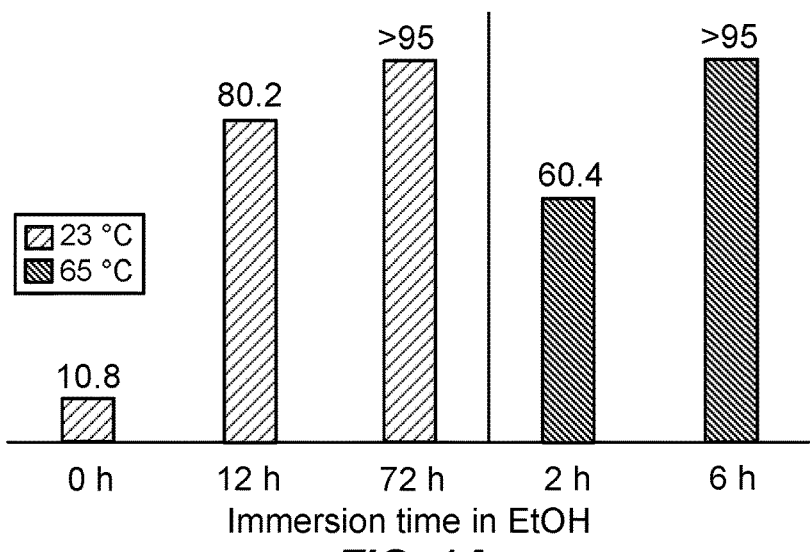
FIG. 1A shows the extent of SPMF in water after immersion in EtOH at 23 or 65° C. for 0-72 h.
Figure 1B:
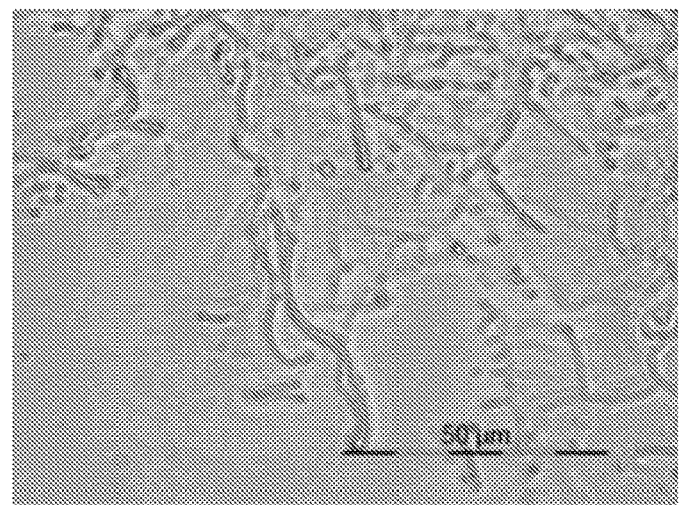
FIG. 1B shows aq. SPMF at 0.1% air-dried and imaged by the optical microscope.

The present invention provides compositions of soy protein gel fibers, soy protein fiber membranes, and soy protein films. Further, the present invention also provides methods of preparing the soy protein gel fibers, membranes, and films. The gel fibers can be useful for pickering emulsions to stabilize two phases in an emulsion. The soy protein fiber membranes can be used for filtering and recovering compounds such as dyes. The soy protein films can be used for controlled drug delivery and release.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"A," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

"Gel fiber" refers to a semi-solid fiber comprising soy protein fibers from SPC, SPMF, or both, and an organic liquid solvent. Gel fibers can have a diameter on the micrometer scale, such as, but not limited to 100 to 1500 μm.

"Soy protein colloid (SPC)" refers to a homogenous aqueous solution comprising soy protein fibers which are amphiphilic. Soy protein fibers in the colloid after removal of aqueous solution by drying are referred to as dried soy protein colloids. Soy protein colloids are made from soy protein isolates which are stirred are blended. Fibers of soy protein colloids have can have a diameter of about 150 to 250 nm in aqueous solution, and about 5 to 50 nm when dried.

"Soy protein microfibril (SPMF)" refers to soy protein fibers, which have a diameter of about 1 to 10 μm. Soy protein microfibrils can be made from freezing and lyophilizing soy protein colloids.

"Solvent" refers to a substance, usually a liquid, but can also be a solid or gas, that can dissolve other compounds and small molecules to form a solution. Liquid solvents include, but is not limited to organic solvents such as hydrocarbon and aromatic solvents. Examples of hydrocarbon solvents include, but are not limited to hexane, cyclohexane, octane, decane, and hexadecane.

"Soy oil" refers to a type of vegetable oil that is extracted from the seeds of the soybean.

"Soy protein fiber membrane" refers to a membrane layer comprising soy protein fibers from SPC, SPMF or both, that is permeable to certain species of compounds, while filtering out other species of compounds. The membrane further comprises synthetic polymers such as, but not limited to, polyvinyl alcohol. Depending on reaction conditions, the membrane can adsorb cationic or anionic compounds of interest for recovery of materials.

"Substantially water-insoluble" refers to a composition or compound which is not water soluble to a great or significant extent. For example, substantially water-insoluble can include, but is not limited to, a composition or compound which is greater than 90% insoluble in water.

"Crosslinker" refers to a bifunctional compound that reacts with two different reactive functional groups on a solid phase support, thereby linking functional groups to each other. This can be beneficial for minimizing pore sizes for films and membranes, and for strengthening the stability of the films or membranes. The preferred crosslinkers of the present invention are able to stabilize the films or membranes of the present invention, such that the films or membranes do not disintegrate in aqueous solutions.

"Amphoteric" refers to compositions comprising functional groups which can act as either an acid or a base. Amphoteric compositions, such as amphoteric films and membranes, can be utilized for adsorption or desorption of either cationic or anionic dyes depending on the reaction conditions.

"Soy protein film" refers to a film layer comprising soy protein fibers from SPC, SPMF, or both, wherein at least 40% of the secondary structures of the soy protein fibers comprise β-sheets. Dried soy protein films can regain moisture in aqueous solution or relatively high humidity conditions, and swell to form a more flexible film, which may be useful for drug delivery.

"Secondary structures" refers to protein secondary structures such as, but not limited to, alpha helices, beta sheets, beta strands, beta turns, and omega loops.

"Drug" refers to an agent capable of treating and/or ameliorating a condition or disease. A drug may be a water-soluble drug or a hydrophobic drug. Water-soluble drugs useful in the present invention include, but are not limited to, methylene blue, penicillin G, and gentamicin. One of skill in the art will appreciate that other drugs are useful in the present invention.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Subject" refers to animals such as mammals, including, but not limited to, primates (e.g., humans), cows, sheep, goats, horses, dogs, cats, rabbits, rats, mice and the like. In certain embodiments, the subject is a human.

"Therapeutically effective amount or dose" or "effective amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

III. Gel Fibers

In some embodiments, the present invention provides a gel fiber composition comprising: a soy protein colloid (SPC) or soy protein microfibril (SPMF); sodium alginate (SA); and a hydrocarbon solvent or soy oil.

The gel fiber composition of the present invention comprises a soy protein colloid (SPC) or soy protein microfibril (SPMF) as described herein. The soy protein colloids and soy protein microfibrils can have different fiber diameters. For example, the diameter of soy protein colloids are within the nanometer scale, whereas soy protein microfibrils are on the micrometer scale.

The soy protein colloids can have any suitable diameter. For example, the soy protein colloids can have a diameter from 1 to 1000 nm, or from 1 to 750, 1 to 500, or from 5 to 250 nm. In some embodiments, soy protein colloids have a diameter of 100 to 250 nm in aqueous solution. In some embodiments, soy protein colloids have a diameter of 150 to 250 nm in aqueous solution. Dried soy protein colloids can have a diameter of from 1 to 100 nm, or from 1 to 75, from 1 to 50, 5 to 50, 5 to 25, 5 to 20, or from 5 to 10 nm. In some embodiments, dried soy protein colloids have a diameter of 5 to 50 nm. In some embodiments, dried soy protein colloids have a diameter of 5 to 20 nm. In some embodiments, dried soy protein colloids have a diameter of 5 to 10 nm.

The soy protein microfibrils can have any suitable diameter. For example, the soy protein microfibrils can have a diameter from 1 to 100 μm, or from 1 to 75, 1 to 50, 1 to 25, 1 to 10, 1 to 5, 1 to 4, 1 to 3, or 1 to 2 μm. In some embodiments, soy protein microfibrils have a diameter of 1 to 50 μm. In some embodiments, soy protein microfibrils have a diameter of 1 to 25 μm. In some embodiments, soy protein microfibrils have a diameter of 1 to 10 μm. In some embodiments, soy protein microfibrils have a diameter of 1 to 2 μm.

The gel fiber composition of the present invention further comprises sodium alginate (SA). The sodium alginate can be present in any suitable ratio to the SPMF. For example, the gel fiber composition can include SPMF and SA in a ratio of 1:1 to 100:1 (w/w), or 1:1 to 75:1, 1:1 to 50:1, 1:1 to 25:1, or 1:1 to 10:1. In some embodiments, the gel fiber composition comprises SPMF and SA in a ratio of 1:1 to 10:1 (w/w). In some embodiments, the gel fiber composition comprises SPMF and SA in a ratio of 1:1 to 7:1 (w/w). In some embodiments, the gel fiber composition comprises SPMF and SA in a ratio of 1:1 to 4:1 (w/w). In some embodiments, the gel fiber composition comprises SPMF and SA in a ratio of 1:1 or 2:1 (w/w/).

The gel fiber composition of the present invention also comprises a hydrocarbon solvent or soy oil. Hydrocarbon solvents useful in the present invention include, but are not limited to, cyclopentane, cyclohexane, cyclohexene, cycloheptane, cyclooctane, pentane, hexane, heptane, octane, decane, dodecane, tetradecane, and hexadecane. In some embodiments, the hydrocarbon solvent is cyclopentane, cyclohexane, cycloheptane, dodecane, tetradecane, or hexadecane. In some embodiments, the hydrocarbon solvent is cyclohexane or hexadecane. In some embodiments, the hydrocarbon solvent is hexadecane.

In some embodiments, the gel fiber composition of the present invention comprises cyclopentane, cyclohexane, cycloheptane, dodecane, tetradecane, hexadecane, or soy oil. In some embodiments, the gel fiber composition comprises cyclohexane, hexadecane, or soy oil. In some embodiments, the gel fiber composition comprises cyclohexane. In some embodiments, the gel fiber composition comprises hexadecane. In some embodiments, the gel fiber composition comprises soy oil.

In some embodiments, the gel fiber composition comprises: SPMF and SA in a ratio of 1:1 to 4:1 (w/w); and cyclohexane, hexadecane, or soy oil in an amount of 60 to 90% (v/v). In some embodiments, the gel fiber composition comprises: SPMF and SA in a ratio of 2:1 (w/w); and hexadecane in an amount of 75% (v/v).

In some embodiments, the gel fiber has a diameter of 100 to 1500 μm. In some embodiments, the gel fiber has a diameter of 300 to 1000 μm. In some embodiments, the gel fiber has a diameter of 100 to 200 μm, 300 to 500 μm, 600 to 700 μm, or 800 to 1000 μm. In some embodiments, the gel fiber has a diameter of 300 to 500 μm.

In some embodiments, the present invention provides a method for preparing the gel fiber of the present invention, the method comprising: (a) forming a reaction mixture comprising a soy protein colloid (SPC) or soy protein microfibril (SPMF), sodium alginate (SA), and a hydrocarbon solvent or soy oil; and (b) spinning the reaction mixture into a CaCl₂ aqueous solution, thereby forming the gel fiber.

The reaction mixture of the present invention comprises SPMF and SA in a ratio as described above. In some embodiments, the reaction mixture comprises SPMF and SA in a ratio of 1:1 to 4:1 (w/w). Further, the combination of SPMF and SA can be present in the reaction mixture in any suitable amount. In some embodiments, the combination of SPMF and SA is present in an amount of 1% to 20% (w/w). In some embodiments, the combination of SPMF and SA is present in an amount of 1% to 10% (w/w). In some embodiments, the combination of SPMF and SA is present in an amount of 1% to 5% (w/w/). In some embodiments, the combination of SPMF and SA is present in an amount of 1%, 2%, 3%, or 4%. In some embodiments, the combination of SPMF and SA is present in an amount of about 2%.

In some embodiments, the reaction mixture comprises SPMF and SA in a ratio of 1:1 to 4:1 (w/w), and the combination of SPMF and SA is present in an amount of 1% to 5% (w/w). In some embodiments, the reaction mixture comprises SPMF and SA in a ratio of 1:1 to 4:1 (w/w), and the combination of SPMF and SA is present in an amount of about 2% (w/w). In some embodiments, the reaction mixture comprises SPMF and SA in a ratio of 2:1 (w/w), and the combination of SPMF and SA is present in an amount of about 2% (w/w).

The CaCl₂ aqueous solution of the present invention can have any suitable molarity. In some embodiments, the CaCl₂ aqueous solution comprises 0.1 M to 2.0 M CaCl₂. In some embodiments, the CaCl₂ aqueous solution comprises 0.1 M to 1.0 M CaCl₂. In some embodiments, the CaCl₂ aqueous solution comprises 0.5 M CaCl₂.

IV. Soy Protein Fiber Membranes

In some embodiments, the present invention provides a soy protein fiber membrane comprising: a soy protein colloid (SPC) or a soy protein microfibril (SPMF); and polyvinyl alcohol (PVA), wherein the soy protein fiber membrane is substantially water-insoluble.

The soy protein colloid (SPC) and soy protein microfibril (SPMF) useful in the membrane is described above. In some embodiments, the membrane comprises SPC and PVA. In some embodiments, the membrane comprises SPC and PVA in a ratio of 1:1 to 10:1 (w/w). In some embodiments, the membrane comprises SPC and PVA in a ratio of 1:1 to 9:1 (w/w). In some embodiments, the membrane comprises SPC and PVA in a ratio of about 1:1, 3:1, 7:3, or 9:1 (w/w). In some embodiments, the membrane comprises SPC and PVA in a ratio of about 7:3 (w/w).

The membrane of the present invention can further comprise a crosslinker. In some embodiments, the membrane further comprises a genipin, gallic acid, ferulic acid, formaldehyde, or glutaraldehyde crosslinker. In some embodiments, the membrane further comprises genipin, gallic acid, or ferulic acid crosslinker. In some embodiments, the membrane further comprises a genipin crosslinker.

The membrane of the present invention is substantially water-insoluble. Substantially water-insoluble can refer to the membrane being at least 90% insoluble in water. In some embodiments, the membrane is about 90%, 91%, 92%, 93%, 94%, 95%, 96%, 97%, 98%, or 99% water-insoluble. In some embodiments, the membrane is about 90% to 95% water-insoluble.

The membrane of the present invention is substantially water-insoluble in a solution having a broad pH range. For example, the membrane can be substantially water-insoluble in a solution having a pH of less than 12, 11, 10, 9, 8, 7, 6, 5, 4, 3 or less than 2. In some embodiments, the membrane of the present invention is substantially water-insoluble at a pH of less than 12. In some embodiments, the membrane of the present invention is substantially water-insoluble at a pH of less than 10. In some embodiments, the membrane of the present invention is substantially insoluble between a pH of 1 to 10.

In some embodiments, the membrane of the present invention is amphoteric. Without being bound by any particular theory, amphoteric membranes can be useful for selective adsorption of either cationic or anionic dyes, as well as for selective adsorption and desorption for dye recovery and membrane recycling.

In some embodiments, the present invention provides a method for preparing the soy protein fiber membrane of the present invention, the method comprising: (a) forming a reaction mixture comprising a soy protein colloid (SPC) or soy protein microfibril (SPMF), and polyvinyl alcohol (PVA); (b) electrospinning the reaction mixture into fibers; and (c) heat treating the fibers at a temperature of at least 100° C., thereby forming the soy protein membrane.

The reaction mixture of the present invention comprises SPC and PVA in a ratio as described above. In some embodiments, the reaction mixture comprises SPC and PVA in a ratio of 1:1 to 9:1 (w/w). In some embodiments, the reaction mixture comprises SPC and PVA in a ratio of about 7:3 (w/w).

The membrane of the present invention is formed by electrospinning the reaction mixture into fibers. Electrospinning is a fiber production method which uses electric force to draw charged threads of polymer solutions or polymer melts wherein the fiber diameters can be as small as some hundred nanometers. The membranes of the present invention can be formed by electrospinning at any suitable voltage. For example, the electrospinning can be performed at 5 to 50 kV, 5 to 25 kV, or 10 to 20 kV. In some embodiments, the electrospinning is performed at 5 to 25 kV. In some embodiments, the electrospinning is performed at 10 to 20 kV. In some embodiments, the electrospinning is performed at about 15 kV.

Heat treating the membranes of the present invention can be useful for improving the aqueous stability of the membranes. In some embodiments, the method for preparing the membrane comprises heat treating the fibers at a temperature of at least 100° C. In some embodiments, the temperature is between 100° C. to 200° C. In some embodiments, the temperature is 150° C.

The length of time for heat treating the membranes of the present invention can be any suitable time. In some embodiments, heat treating the fibers is performed for 6 to 120 hours. In some embodiments, heat treating the fibers is performed for 6 to 72 hours. In some embodiments, heat treating the fibers is performed for 12 to 48 hours. In some embodiments, heat treating the fibers is performed for 24 to 48 hours.

In some embodiments, heat treating the fibers at 150° C. is performed for 12 to 48 hours.

V. Soy Protein Films

In some embodiments, the present invention provides a soy protein film comprising a soy protein colloid (SPC) or soy protein microfibril (SPMF), wherein the secondary structures of the SPC or SPMF comprises at least 40% β-sheets, and wherein the soy protein film is substantially water-insoluble.

The soy protein colloid (SPC) and soy protein microfibril (SPMF) useful in the membrane is described above. Without being bound to any particular theory, the secondary structures of SPC and SPMF are useful in formation of the substantially water-insoluble soy protein film. The substantially water-insoluble soy protein film comprises at least 40% β-structures including, but not limited to β-sheets and β-turns. In some embodiments, the secondary structures of the SPC or SPMF comprises at least 50% β-structures. In some embodiments, the secondary structures of the SPC or SPMF comprises at least 60% β-structures. In some embodiments, the secondary structures of the SPC or SPMF comprises 64% β-structures.

In some embodiments, the secondary structures of the SPC or SPMF comprises at least 40% β-sheets. The presence of secondary structures can be measured by circular dichroism (CD) or Fourier-transform infrared spectroscopy (FTIR). Using FTIR, β-sheets are detected within the range of 1613-1637 cm⁻¹ and 1682-1689 cm⁻¹. For further details regarding known FTIR techniques to determine secondary structures, see Liu, X.; Hsieh, Y.-L., Amphiphilic and amphoteric aqueous soy protein colloids and their cohesion and adhesion to cellulose. *Industrial Crops and Products,* 2019. In some embodiments, the secondary structures of the SPC or SPMF comprises about 48% β-sheets. In some embodiments, the soy protein film comprises SPMF, and the secondary structure of SPMF comprises about 48% β-sheets.

The soy protein film of the present invention is substantially water-insoluble in a solution having a broad pH range.

For example, the soy protein film can be substantially water-insoluble in a solution having a pH of less than 12, 11, 10, 9, 8, 7, 6, 5, 4, 3 or less than 2. In some embodiments, the soy protein film of the present invention is substantially water-insoluble at a pH of less than 12. In some embodiments, the soy protein film of the present invention is substantially water-insoluble at a pH of less than 10. In some embodiments, the soy protein film of the present invention is substantially insoluble between a pH of 1 to 10.

In some embodiments, the present invention provides a method for selectively delivering a compound, the method comprising administering to a subject in need thereof, an effective amount of the soy protein film of the present invention, wherein the soy protein film further comprises a compound.

In some embodiments, the present invention provides a method for selectively delivering a drug, the method comprising administering to a subject in need thereof, an effective amount of the soy protein film of the present invention, wherein the soy protein film further comprises a drug.

Drugs useful in the present invention include any suitable hydrophobic drug or water-soluble drug. Water-soluble drugs include non-ionic and ionic drugs. In some embodiments, the drug is methylene blue, penicillin G, atenolol, or gentamicin. In some embodiments, the drug is methylene blue.

VI. Examples

Example 1: SPC and SPMF Used in Gel Fibers

Materials. Soy protein isolate (SPI, 92% protein) was purchased from MP Biomedicals, LLC. Ethanol (EtOH, anhydrous, histological grade), hexadecane (Certified ACS), soybean oil, and calcium chloride dihydrate (Certified ACS, >99.0%) were purchased from Fisher Scientific. Sodium alginate was from Acros Organics. Regenerated cellulose dialysis membranes with 3.5 kDa molecular weight cut-off were purchased from Fisherbrand (Pittsburgh, PA). Highest Grade V1 Mica Discs (15 mm) were purchased from Ted Pella. All water used was purified by Milli-Q plus water purification system (Millipore Corporate, Billerica, MA).

Adsorption of SPC and SPMF on mica and polystyrene. Freshly cleaved mica or polystyrene films were immersed in aq. SPC or SPMF at 1.5% for 15 min, rinsed with three different sets of deionized water and then dried under filtered compressed air stream.

Aq. SPMF (0.01%, 10 μL) air-dried on a freshly cleaved mica and the mica coated with one layer of SPC were respectively imaged by atomic force microscopy (AFM, MFP-3D, Oxford Instruments Asylum Research, Inc., Santa Barbara, CA) and scanned in the tapping mode with OMCL-AC160 TS standard silicon probes (tip radius<10 nm, spring constant=28.98 N/m, resonant frequency of ca. 310 kHz) (Olympus Corp.) at 1 Hz scan rate under the ambient condition. Both the air-dried aq. SPMF (0.1%) and wet-spun fibers on glass slides and the mica coated with one layer of SPMF were also observed under a Leica DM2500 optical microscope equipped with the cross-polarizing filter. The isoelectric point (PI) of SPMF (1%, 25 g) was determined by titrating with 0.1 M HCl and the pH was recorded using OAKTON pH/Con 510 series meter to derive the pH at which the second derivative was zero. Surface tensions of aq. SPMF dispersions with serial dilutions were measured over the concentration gradient by the Wilhelmy plate method using a liquid tensionmeter (K100, Kruss GmbH, Germany) at ambient temperature. The platinum plate was immersed for 3 mm and thoroughly rinsed after each measurement with water and dried under filtered compressed air stream. Each measurement was repeated for 5 times and the average with the standard deviation was plotted.

To study the chemical composition and the secondary structure of crude SPI, air-dried and freeze-dried SPC and SPMF, Fourier transform infrared attenuated total reflection (FTIR-ATR) spectra was collected from 1700 to 1600 cm$^{-1}$ at a resolution of 2 cm$^{-1}$ by a Nicolet iN10 microscope spectrometer (Thermo Fisher Scientific, USA) using a liquid nitrogen cooled detector and analyzed as reported (Liu, X.; Hsieh, Y.-L., Amphiphilic and amphoteric aqueous soy protein colloids and their cohesion and adhesion to cellulose. *Industrial Crops and Products,* 2019). X-ray diffraction (XRD) patterns were collected on a Scintag XDS 2000 powder diffractometer using a Ni-filtered Cu Kα radiation (=1.5406 Å) at an anode voltage of 45 kV and a current of 40 mA. Samples were compressed between two glass slides into flat sheets with around 1 mm thickness and diffractograms were recorded from 5° to 40° at a scan rate of 2°/min. Peak deconvolution analysis was conducted using Peak Fit (Systat Software) and individual peaks were fitted by Gaussian functions with R$^2$>0.99 for all deconvolutions. The ratio of total crystalline peak areas and the sum of both crystalline and amorphous area was taken as the crystallinity index (CrI) and the unit cell dimension was calculated based on Bragg's law. Thermal behavior of crude SPI, air-dried and freeze-dried SPC and SPMF were measured using a Shimadzu thermal analysis system (TA-SOWSI), including a differential scanning calorimeter (DSC-60) and a thermo gravimetric analyzer (TGA-50). Both DSC and TGA were performed by heating at 10° C./min under flowing N$_2$ at a 50 mL/min rate to 400° C. The first derivative was derived from the TGA data and plotted as the DTG curve. Water contact angle of the mica and polystyrene surface coated with one layer of SPC or SPMF was measured by using the drop shape analysis method.

Figure 1C:
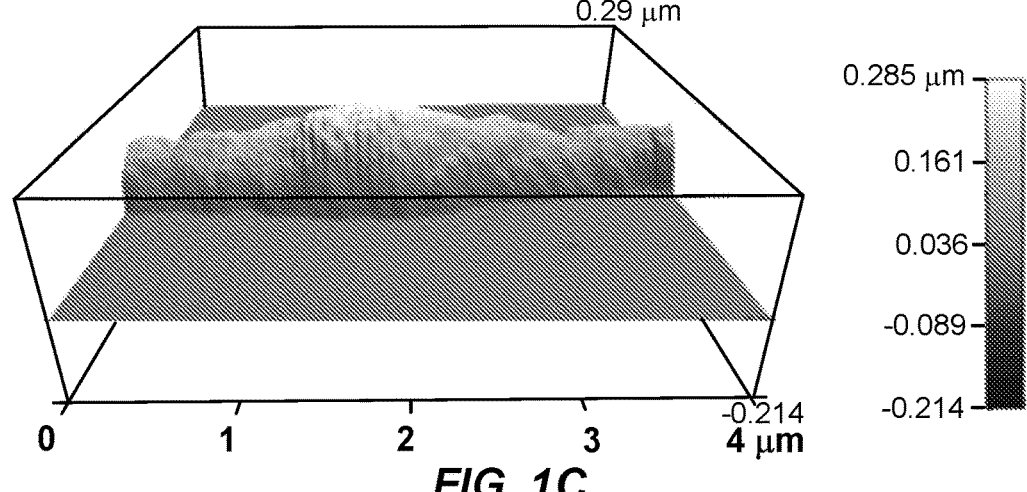
FIGS. 1C-1E show the AFM images of SPMF air-dried at 0.01%: 3D (FIG. 1C), height (FIG. 1D), and phase (FIG. 1E).
Figure 1D:
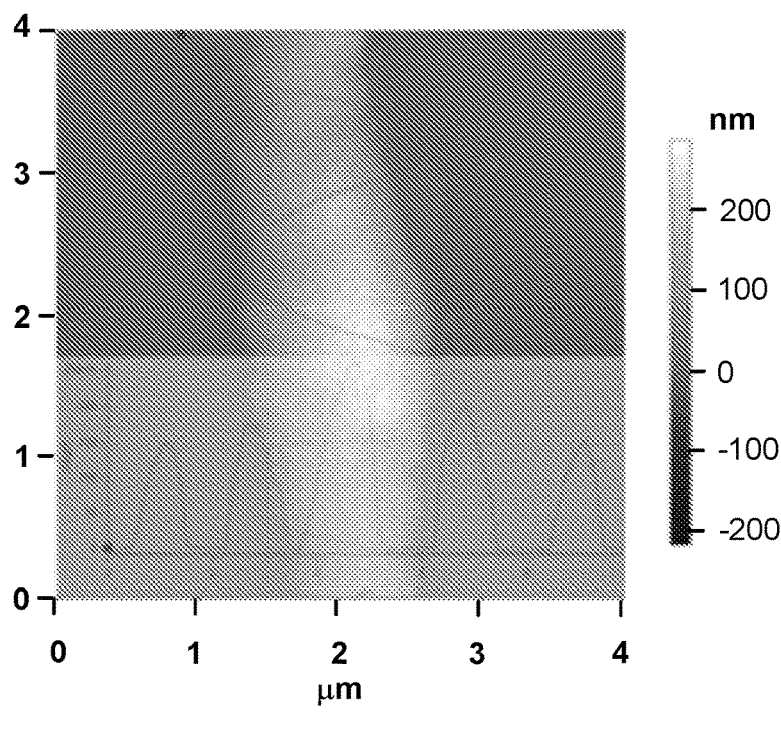
Figure 1E:
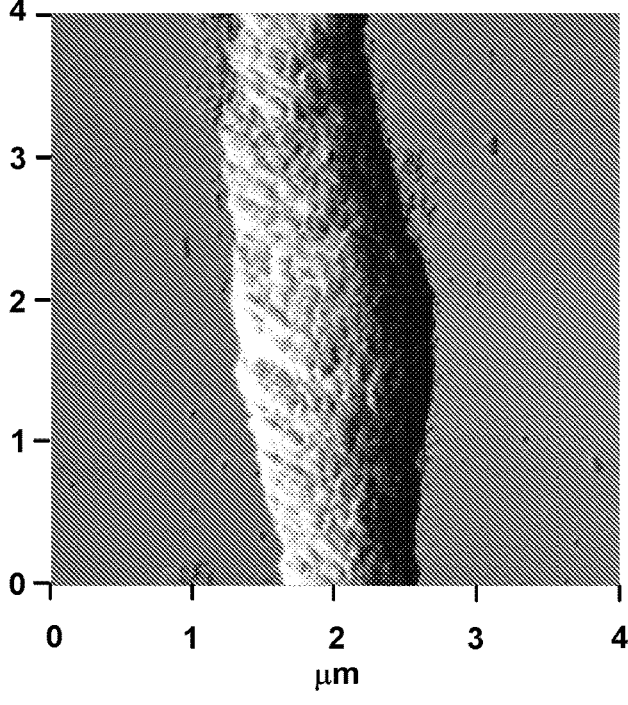

Aq. SPC and SPMF characteristics. Aqueously dispersed soy protein isolate (SPI) was mechanically blended (30 k rpm, 15 min) into soy protein colloids (SPC) with the isoelectric point of 4.51 and had an average hydrodynamic diameter of 157.1-233.1 nm with the ζpotential of +33.1 to −42.9 mV at pH 2-10 (Table 1). Freezing (−196° C., 5 min) and lyophilization of 1 SPC produced laminated fibrous structures that could be dispersed into 1.19-1.29 μm wide and 44.8-70.0 μm long SPMF in organic polar solvents (i.e. alcohols, DMF, and acetone) as well as lipids (i.e. soy and olive oil) (Table 1) and non-polar solvents (i.e. chloroform and toluene). but only 10.8% remained the fibrous morphology in water (FIG. 1A). To render more SPMF water-insoluble, the effect of EtOH immersion was investigated in terms of the time and temperature. At ambient temperature, 12 and 72 h EtOH immersion respectively increased the yield of SPMF in water to 80.2 and >95% (FIG. 1A). By incubating them in EtOH at 65° C. for merely 2 and 6 h, the yield respectively arose to as high as 60.4 and >95% (FIG. 1A). The aqueously dispersed SPMFs had a relatively uniform average width of 1.25 (±0.19) μm and more wide ranging lengths from 15 to 225 μm or 12 to 200 length-to-width aspect ratios by optical microscopy. A close look at SPMF under AFM showed that they were merely 150-250 nm thick, due to their soft nature and adsorption on the mica surface and very irregular in width, meanwhile, they also had wrinkled showing rough surfaces with abundant nanoparticles near the fiber surfaces (FIGS. 1C-1E), corresponding to their formation through the self-assembly of particulates with diverse sizes. Their PI was determined to be 4.98 from the second derivative of the titration curve, slightly more basic side groups than acidic ones exposed on surface as compared to the 4.5 PI of SPC. Alcohols are known to promote the crystallization of proteins (i.e. silk fibroin), particularly the formation of β domains, by exposing more hydrophobic side groups and the simultaneous rearrangement of local H-bondings. EtOH immersion at a higher temperature at 65° C. seemed to accelerate the rearrangement of the H-bondings and induce the significant secondary structural transition towards more β domains.

TABLE 1

| SPC and SPMF characteristics | | |
|---|---|---|
| | SPC | SPMF |
| Dimension | Thickness (air-dried): 6.0 ± 8.0 nm (aq.) or 5.4 ± 5.6 nm (DMF); Width (air-dried): 16.4 ± 11.6 nm (aq.); Hydrodynamic diameter: 157.1-233.1 nm (pH = 2-10, aq.). | Length (air-dried): 44.8-70.0 μm; Width (air-dried): 1.19-1.29 μm. |
| Isoelectric point (PI) | 4.51 | 4.98 |
| CAC, surface tension | 0.98%, 41.3 mN/m | 0.62%, 48.4 mN/m |
| Compatible solvents[a] | Water, DMF[b] or MeOH/Water (4:1, v/v)[b] | Polar: water[c], DMF, alcohols or acetone; Non-polar[c]: chloroform, toluene or hexane/EtOH (1:2, v/v); Lipid: soybean or olive oil |

[a]SPC: uniformly dispersed and remained stable against centrifugal force at 4,500 g; SPMF: uniformly dispersed.
[b]Solvent-exchanged from water
[c]Redispersed from EtOH Assemblies of SPC and SPMF as affected by drying methods. Both freeze-drying and air-drying were respectively applied on 1% aq. SPMF to explore how drying method may affect their assembled structures, crystalline domains, secondary structure composition and thermal behavior. Upon freezing (−196° C., 5 min) and lyophilization, they assembled into ordered capillary-like structures aligning parallel to the temperature gradient with thick cell walls composed of associated microfibrils. Unlike the control and SPC, SPMF cast film exhibited abundant circular structures with Maltese-cross extinction patterns under the crossed polar with a small proportion of well-aligned microfibrils with strong birefringence, indicative the highly oriented fine structures.

Both FD (72%) and AD (71%) SPMF had a similarly high CrI like crude SPI (71%), significantly higher than FD control (43%) and SPC (41%) and very close to that of AD SPC (72%). All analyzed SP materials owned a similar ratio of α- and β-structures except that crude SPI had 13% more β domains based on the XRD analyses. Consistent with XRD results, the FTIR amide I band analysis indicated that both FD and AD SPMF showed distinct band morphologies shifting to the β-sheet region (1613-1637 cm$^{-1}$) and owned

Figures 2A, 2B, 2C:
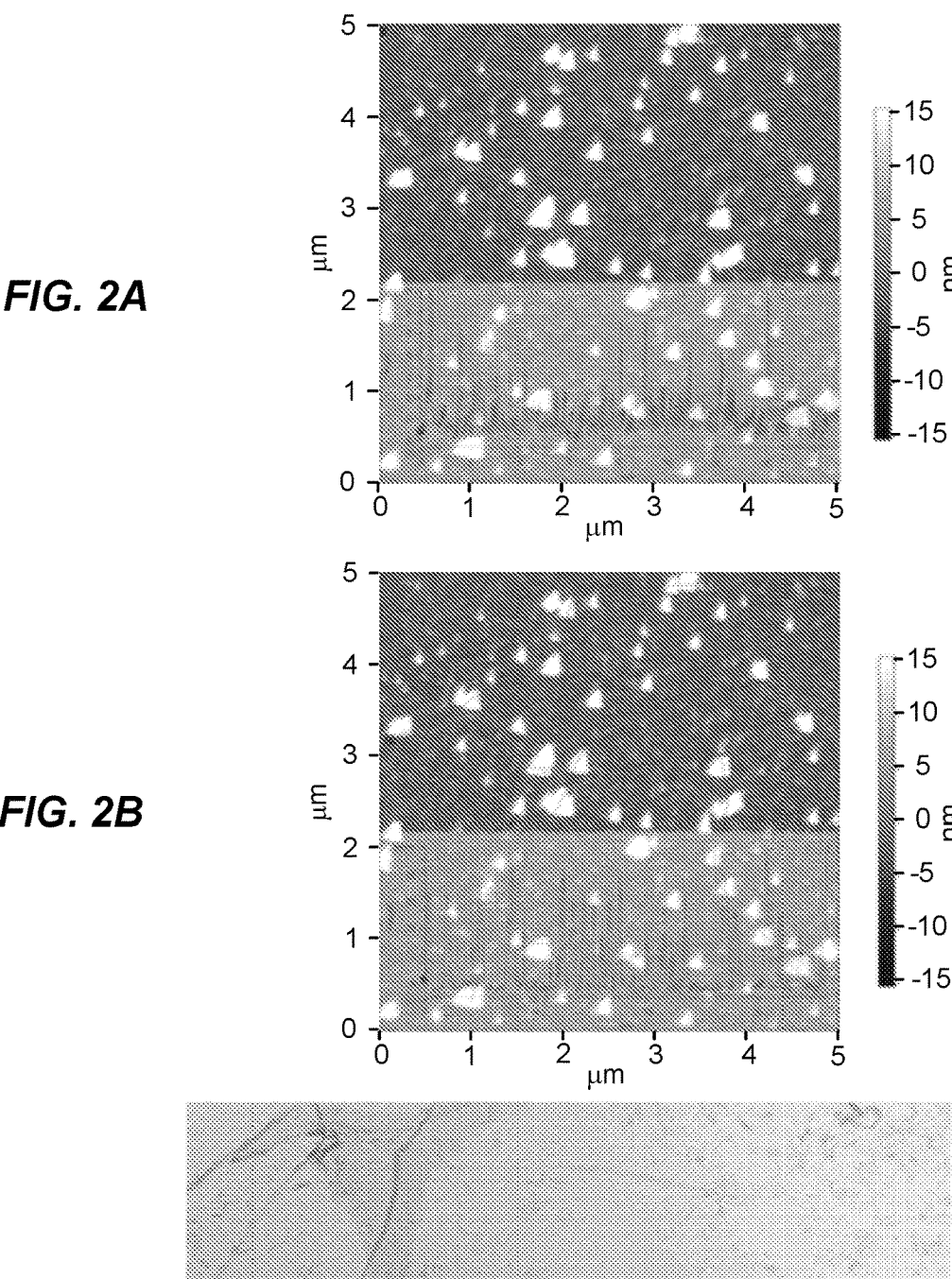
FIGS. 2A-2D show freshly peeled mica and polystyrene surfaces deposited with water (control) or one layer of SPC or SPMF.

15 the substantially higher content of ordered secondary structures (95 and 95%), especially as high as 61 and 71% β structures. As compared to lyophilization, more β structures were formed during the air-drying process, such as 11% more parallel β-turns in AD SPC and 20% more anti-parallel β-sheets in AD SPMF (FIGS. 2B-2C). Unlike the sublimation in freeze-drying, evaporation in air-drying seems to encourage the formation of intense intermolecular interactions that lead to more crystalline domains and ordered secondary structures. However, in the case of SPMF, they may reach the maximal proportion of crystalline domains or highly ordered structures, the effect of drying methods was minor. Glass transition temperature ($T_g$) of SPs was overall identified at 199.5-199.9° C. from the DSC curve except that both FD and AD SPMF had a substantially higher one at 213.5 and 220.9° C., respectively. The presence of α-helical and β secondary structures in proteins are generally thought to resemble crystalline zones in other polymers and $T_g$ of protein materials typically increases by 6-10° C. for a 10% increase in the content of crystalline domains. Therefore, higher $T_g$ of FD and AD SPMF seems to be consistent with their higher CrI (71 and 72%) and more ordered secondary structures (95 and 95%).

Intermediate wettability of SPC and SPMF. Both SPC and SPMF have shown to exhibit surface active behaviors with SPMF capable of reducing the surface tension of water to 48.4 mN/m a CAC of 0.62% as opposed to the 41.3 mN/m surface tension at 0.98% a CAC. While aq. colloidal SPC showed limited solvent-exchange ability to DMF or 4:1 v/v methanol/water, SPMF could be homogeneously dispersed in almost all polar and nonpolar solvents except for alkanes (Table 1), suggesting a more balanced surface hydrophilic and hydrophobic moieties. Hydrophilic-Lipophilic Balance (HLB) of surfactant molecules could be determined as the following per Davie's methods, $$HLB = 7 + \sum_{i=1}^{m} H_i - n \times 0.475$$

where m is the number of hydrophilic groups in the molecule, n is the number of lipophilic groups in the molecule and $H_i$ is the value of the $i_{th}$ hydrophilic groups. As SPC and SPMF consist the same AA compositions, their HLB values depend on the surface functional groups and the charged state of polar ones. Therefore, distinct surface-active properties of SPC and SPMF reflect the conformational freedom of colloidal SPC and the balanced proportions of surface hydrophilic and hydrophobic moieties of SPMF.

Figure 2D:
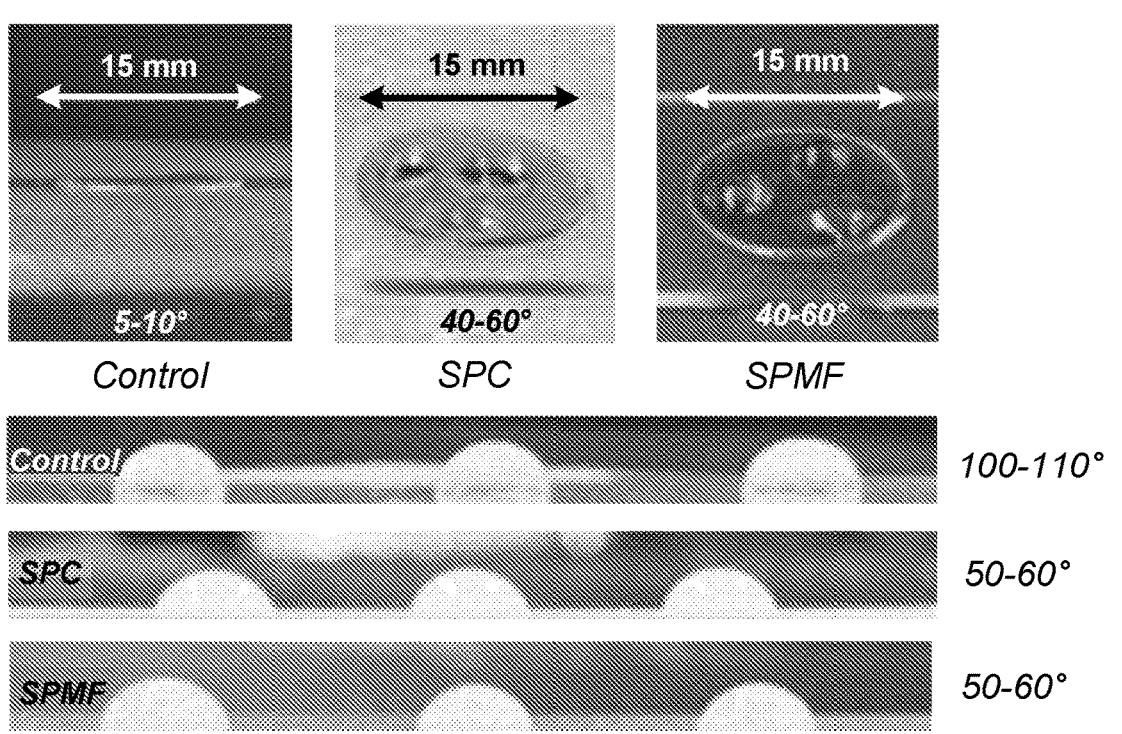

Aq. SPC and SPMF were deposited on either freshly cleaved hydrophilic mica (<5° water contact angle) and hydrophobic polystyrene (PS) following the layer-by layer procedure to explore how they respond to different surfaces. With 1-4 nm thick SPC or 150-250 nm thick SPMF coating on mica, the water contact angle was substantially increased to 40-60° (FIGS. 2A-2D). Coating the same on hydrophobic PS surface (RMS<1 nm, WCA 100-110°) with the root mean square roughness of <1 nm also led to changed water contact angle to the similar range of 50-60° (FIG. 2D). That SPMFs capable of orient themselves to be adsorb on a hydrophilic or hydrophobic surface via hydrophilic-hydrophilic or hydrophobic-hydrophobic interactions and yet exposing the same amphiphilic surface implies their potential applications for surface modification. Particularly, amphoteric SPC (PI=4.51) and SPMF (PI=4.98) could carry different charges by protonating —$NH_2$ or deprotonating —COOH groups to create amphoteric surfaces on polar and non-polar surface via layer-by-layer deposition.

Example 2: Gel Fiber Formation

SPC, SPMF and their assemblies via freeze-drying and air-drying. Crude SPI was dispersed in water by a glass rod and dialyzed at 8-11° C. for 24 h. They were either magnetically stirred for 1 h as the control or blended at 30 k rpm for 15 min using a high-speed blender (Vitamix 5200) and then centrifuged (5 k rpm, 15 min) to collect the supernatants that designated as aq. SP colloids (SPCs). Aq. SPC (1%, 25 g) was put in 50 mL polypropylene centrifuge tubes with the diameter of 1.1 inch, frozen by immersing in liquid nitrogen (−196° C., 5 min), and then lyophilized (−50° C., 2 d) in a freeze-drier (FreeZone 1.0 L Benchtop Freeze Dry System, Labconco) into "freeze-dried or FD SPC for short. FD SPC were then dispersed in EtOH at 1 w/v % by sonication (Branson ultrasonic processor model 2510, Danbury, CT, 130 W, 5 min) and stored at 23 or 65° C. for 0-3 d, centrifuged (5 k rpm, 15 min) to collect precipitates and then redispersed in water. The same centrifugation and redispersion of precipitates were repeated twice to achieve the final aq. soy protein microfibril (SPMF) dispersions. The yield of SPMF in water was calculated by measuring the dry weight of SPs in triplicate. Aq. SPMF dispersion at 1% was frozen and freeze-dried in the same way as described above to achieve FD SPMF. Cast films of SPMF at 1% were prepared by air drying 1 g in weight boats at 65° C. for 4 h. All SP concentrations were in weight % and reported simply as % unless stated otherwise.

Pickering emulsions, gels and gel fibers. Pickering emulsions were prepared at ambient temperature by the vortex mixing (~3.2 k rpm) the mixture of aq. SPC or SPMF at 0.1-6% with different volume fractions of hexadecane (33.3-97.5 v/v %) or soybean oil (10 v/v %) unless stated otherwise. Two different protocols were used to load hexadecane: (1) direct mixing of all hexadecane with aq. SPC or SPMF; (2) a pre-emulsion (Ø=50%) was prepared first then the remaining hexadecane was mixed. Vortexing was applied for no longer than 5 min and then the top clear oil layer was carefully removed, and its volume was measured. The max internal phase was then calculated from dividing the emulsified volume by the total volume.

HIPE gels and gel fibers. HIPEs (Ø=60-90%, cyclohexane, hexadecane, or soy oil) stabilized by aq. SPMF/SA (1:1-4:1, w/w, 2 w/v %) were loaded into a 10 mL syringe and spun into 0.5 M $CaCl_2$ aq. solutions at room temperature through a stainless needle (27 or 34 G). The flow rate was fixed at 0.2-1.5 mL/min by using a Fusion 100 syringe pump (Chemyx Inc.). The fibers were instantly and continuously collected on a 50 mm winding spool, at a line speed of 2-4 m/min. Aq. $CaCl_2$ solutions (0.5 M) were filled on the top of HIPEs (Ø=90%, hexadecane or cyclohexane) stabilized by aq. SPMF/SA (2:1, w/w, 2 w/v %) for Xh to allow the diffusion of $Ca^{2+}$ into the continuous phase to crosslink the gel.

TABLE 2

| | | | Continuous phase | | Spinning condition | | Observation of fibers | | |
|---|---|---|---|---|---|---|---|---|---|
| # | Oil | $\phi$ (%) | SPMF:SA (w/w, 2 %) | Syringe (G) | Feeding rate (mL/h) | Width ($\mu$m) | Collection | | |
| 1 | Cyclohexane | 60 | 1:1 | 27 | 12 | 800-1000 | Continuous and smooth | | |
| 2 | | | | 27 | 60-90 | 300-500 | spinning; fibers were strong | | |
| 3 | | | | 34 | | 100-200 | enough to be instantly | | |
| 4 | | 75 | 2:1 | 27 | | 300-500 | collected from the coagulant | | |
| 5 | Soy oil | 85 | | | | 300-500 | bath on a winding spool. | | |
| 6 | Hexadecane | 75 | | | | | | | |
| 7 | | 60-80 | 3:1 | | | | Spinnable but not strong | | |
| 8 | | 80-90 | 4:1 | | | | enough to be picked up. | | |

When aq. SPC and SPMF at 0.5% were respectively mixed with hexadecane at the volume ratio of 2:1 or 1:2 by vortexing (~3.2 k rpm, 10 s), the oil phase could only be fully emulsified by SPMF, probably corresponding to their lower CAC. Only when the concentration of aq. SPC was increased to 1 and 2% above their CAC, a homogeneous emulsion with 66.6 v/v % of hexadecane was achieved, while as low as 0.1% SPMF was able to completely emulsify one third volume of hexadecane. Under the optical microscope, emulsion droplets stabilized by SPMF (50-300 µm) were polymodal and overall 2-5 folds larger than those emulsified by SPC (5-50 µm) probably due to their at least one magnitude larger dimensions. Meanwhile, adoptions of smaller droplets on larger ones were widely observed in both cases, implying the sharing of Pickering emulsifiers among droplets and the heterogeneous distribution of hydrophobic and hydrophilic moieties on the surface of SPC and SPMF. The emulsion droplet sizes could be readily decreased by applying higher mechanical shear. For instance, applying high-speed blending (30 k rpm, 15 min) on the mixture of aq. SPC (1%) and soy oil at 9:1 v/v substantially decreased the droplet size from 12.6±9.0 µm (~3.2 k rpm, 10 s) to 0.47±0.22 µm, two magnitude smaller than those stabilized by thermally-induced SP nanoparticles.

Figure 3A:
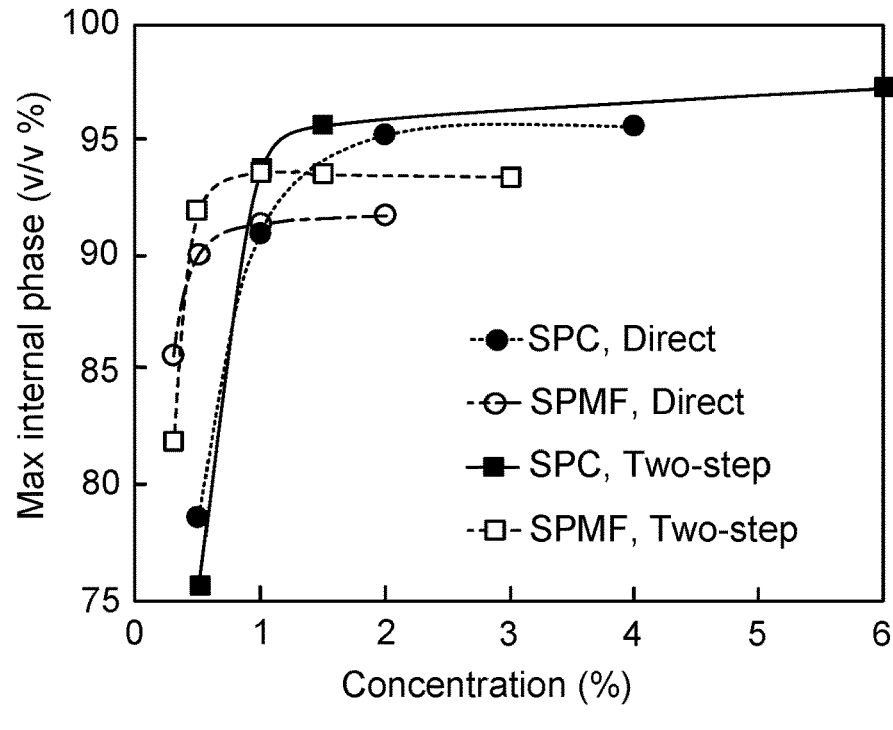
FIG. 3A shows the max internal phase (hexadecane) respectively stabilized by aq. SPC and SPMF following either the direct or two-step mixing approach plotted against their concentration in continuous phase (water). Rheological properties.
Figure 3B:
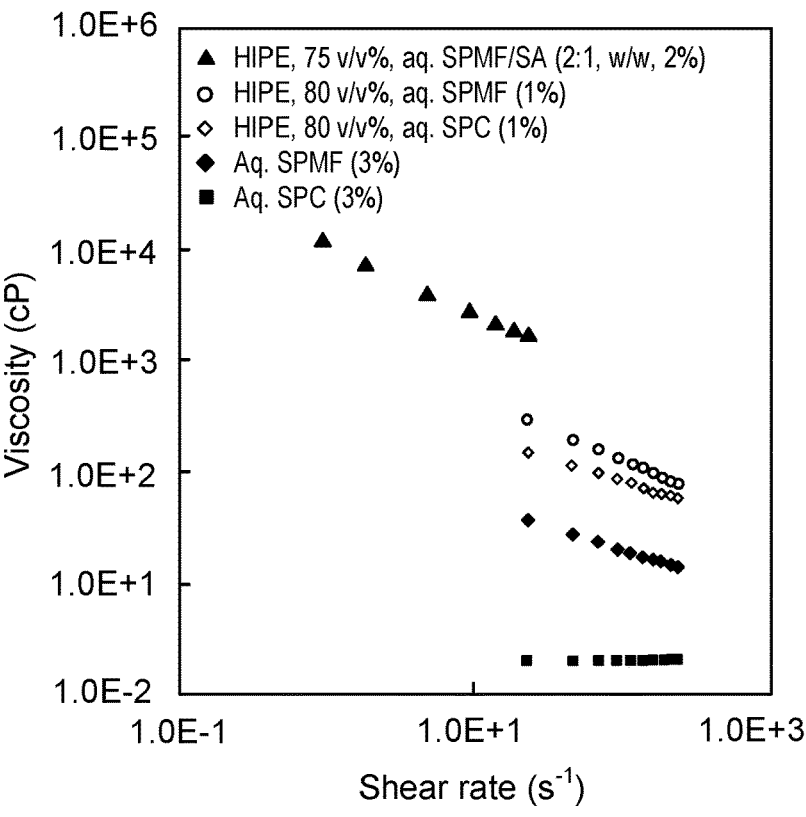
FIG. 3B shows apparent viscosity versus shear rate ($\alpha$=0) and FIG. 3C shows shear stress versus shear rate ($\alpha$=0).
Figure 3C:
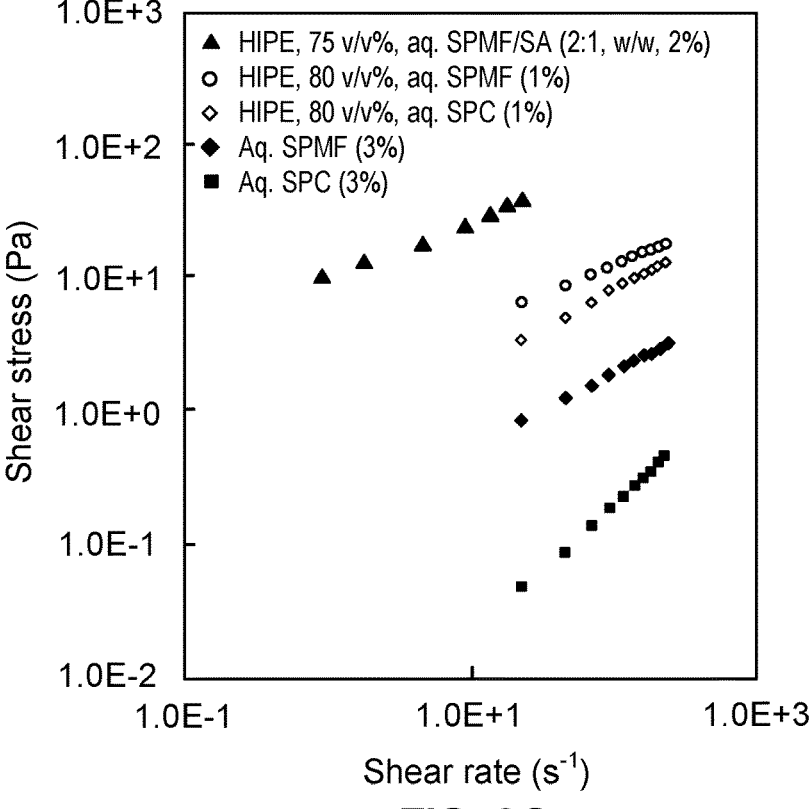

Both aq. SPC and SPMF were able to facilely emulsify >74 v/v % hexadecane via merely vortexing for 10 s-3 min or even shaking by hands, implying their superior intermediate wettability. The internal phase volume of emulsions could be increased by either increasing the polydispersity of droplets size to fill the space among the droplets or deforming droplets from spherical to polygonal to decrease the empty interdroplet space. A two-step procedure, forming a pre-emulsion then loading the remaining liquid has been reported to address both strategies and lead to a higher internal phase volume and/or the formation of a stronger deformable viscoelastic gel. Both the direct and two-step approaches were applied by vortexing the mixture for no longer than 5 min in total to explore the maximal internal phase. Merely 0.3% aq. SPMF could emulsify 85.6 and 81.8 v/v % hexadecane via the direct and two-step approach, respectively, whereas 0.5% aq. SPC could stabilize at most 78.5 and 75.5 v/v % hexadecane (FIG. 3). The maximal internal phase increased with the concentration of SPC and SPMF and reached a plateau respectively at above ca. 1.5 and 1.0% (FIG. 3). Aq. SPC were capable of emulsifying a slightly higher proportion of hexadecane (i.e. 95.6 vs 93.5 v/v %) at 1.5% (FIG. 3). Particularly, 6% pristine aq. SPC were able to emulsify as high as 97.2 v/v % hexadecane via the two-step approach (FIG. 3), meaning that per volume aq. SPC could emulsify 34.7 volumes of hexadecane, even higher than the known maximal (96 v/v %) achieved by chitin nanocrystals with 20 mM NaCl and 0.01 mM HCl at a much lower 0.3 w/v %. Meanwhile, the two-step approach only allowed to emulsify slightly 1.6 and 1.9 v/v % more oil phase for SPC and SPMF, and was not as critical as in the case of sulfated cellulose nanocrystals, in which they were capable of emulsifying 40 v/v % more oil phase. Such facile emulsification process using SP Pickering emulsifier is particularly suitable for applications requiring rapid and facile emulsifications, such as oil separation, food dressing and cosmetic cleansing products.

When a few drops of water or hexadecane were added to HIPEs with very gentle hand shaking, water uniformly distributed while hexadecane separated as a single layer at the top, implying the identity of oil-in-water (o/w) emulsions and the preferential hydrophilicity over the hydrophobicity of SP Pickering emulsifiers. The three-phase contact angle of a solid particle at the water phase when situated at an o/w interface could be derived by the Young's equation, $$\cos\theta_w = \frac{\gamma_{s/o} - \gamma_{s/w}}{\gamma_{o/w}}$$

where $\gamma_{s/o}$ is the solid particle-oil interfacial tension, $\gamma_{s/w}$ is the solid particle-water interfacial tension and $\gamma_{o/w}$ is the oil-water interfacial tension. Pickering emulsifiers stabilizing o/w HIPEs generally have the $\theta_w$ of 70-86°, suggesting that the $\theta_w$ of SPC and SPMF may fall within this range. The majority of biopolymer-derived Pickering emulsifiers were reported to be more hydrophilic except that the esterified bacteria cellulose nanofibrils could stabilize the water-in-oil (w/o) HIPEs.

After dilution, HIPEs appeared as droplets with quite diverse sizes in the range of submicron to a few hundred micrometers under the optical microscope. In HIPEs ($\phi$=80%), a higher concentration of 1% aq. SPC obtained a slightly smaller average droplets diameter (17.8 µm) and 22% more droplets smaller than 5 µm as compared to 0.5% (20.5 µm), approximately half of those stabilized by 1% SPMF (44.9 µm), mainly attributed to their dimensional difference. In comparison, droplets of HIPEs with 80 v/v % hexane stabilized by gelatin particles were 10-50 µmin diameter as determined by dynamic light scattering.

After completely drying one drop of the diluted HIPEs ($\phi$=90%) that stabilized by 1% SPC on glass slides, polygonal and continuous networks composed of SPC that adsorbed at the o/w interface were observed. SPMF were found to be able to bend and adsorb at the surface of emulsion droplets as illustrated by the optical microscope. SPC- and SPMF-stabilized HIPEs with a ϕ of >80% were overall gel-like and self-resistant when they were inverted. After three days, the coalescence was observed on HIPEs with the maximal internal phase stabilized by 1 and 1.5% SPC and 0.5% SPMF, while those stabilized by a higher 1 and 1.5% SPMF were still stable, indicating the better stability of HIPEs emulsified by more concentrated SPMF. The one stabilized by 1.5% SPMF could remain stable for approximately another one week but it would soon show the sign of creaming afterwards.

The total emulsion droplet surface area ($S_d$) could be represented by $$S_d = 4\pi R^2 \times \frac{V_{oil}}{\frac{4}{3}\pi R^3} = \frac{3V_{oil}}{R}$$

where $V_{oil}$ is the volume of oil included in the emulsion and R is the mean radius of the droplets. The theoretical maximum surface that can be covered by the particles or microfibrils is, $$S = N \times \text{Contact surface area} = \frac{m}{h\rho}$$

where N is the number of colloidal particulates or microfibrils, m is the mass of SPs applied in the emulsion, h is the thickness, and ρ is the density of SPs. Therefore, the theoretical surface coverage could be derived as, $$C = \frac{S}{S_d} = \frac{mR}{3h\rho V_{oil}}$$

When the same amount of oil is emulsified by the same amount of SPC or SPMF and the density of particulates and microfibrils is assumed to be the same, $$\frac{C_{SPC}}{C_{SPMF}} = \frac{R_{SPC}h_{SPMF}}{R_{SPMF}h_{SPC}}$$

where $h_{SPMF}$ and $h_{SPC}$ are assigned to be 1.2 μm and 157 nm, respectively. In the case of SPC- and SPMF-stabilized HIPEs (ϕ=80%, 1%), the respective averaged droplet sizes were 17.8 and 46.8 μm, therefore, $C_{SPC}$ and $C_{SPMF}$ were derived as merely 12.3 and 4.2%, respectively, implying the limited stability of both HIPEs in theory. SPC and SPMF with heterogeneous surface hydrophilic and hydrophobic moieties may allow one to serve at the interface of more than one droplet, thus enabling the formation of HIPEs with such low theoretical surface coverage of emulsifiers. The creaming rate of emulsions could be estimated from Stokes' equation:

$$\upsilon = \frac{2R^2}{9\eta}(\rho_c - \rho_d)g$$

where υ is the creaming rate, R is the droplet radius, $\rho_d$ and $\rho_c$ are the density of the dispersed and continuous phase, and η is the viscosity of the continuous phase. This indicates that creaming could be inhibited by small droplet radius and/or a highly viscous continuous phase. Therefore, the better stability of the SPMF-stabilized HIPEs in terms of slower creaming rate may be attributed to the substantially higher viscosity.

Example 3: Soy Protein Fiber Membrane

Uniquely amphoteric soy protein (SP)-rich ultra-fine fibers (231 nm average diameter) have been facilely electrospun from aq. colloids and heat treated to be rendered water-insoluble (pH 7, 14 d) as well as highly stable under extremely acidic to basic (pH 0-10, 2 d) or boiling (2 h) conditions. The SP-rich fibrous membrane could be easily tuned to be either negatively or positively charged by deprotonation above or protonation below the PI (4.5) of SPs. This pH-responsive amphoterism has been demonstrated for rapid adsorption of either cationic or anionic dyes, selective adsorption of either dye from their mixtures as well as cyclic adsorption-desorption for dye recovery and membrane recycling. Ionic dye adsorption on SP-rich fibrous membranes was confirmed to be governed by chemisorption and heterogeneous adsorption by close fitting to the pseudo-second-order kinetic model ($R^2$=0.9977-0.9999) and Freundlich adsorption isotherm ($R^2$=0.9879). These water-resilient and pH-robust ultra-fine fibrous membranes are the first ones to be generated from natural polyampholytes, i.e. globular proteins, from under-utilized agricultural biomass, in aq. media, and without chemical additives to exhibit unique amphoterism that is versatile for applications in the separation and recovery of ionic species.

Materials. Soy protein isolate (SPI, 92% protein) was from MP Biomedicals, LLC. Urea (98.0%, ACS reagent grade), polyvinyl alcohol (PVA, 146-186 kDa, 87-89% hydrolyzed), cibacron brilliant yellow 3G-P (CBY) and Sudan IV red were from Aldrich Chemical Company. Hydrochloric acid (HCl, 1 N, Certified), sodium hydroxide (NaOH, 1 N, Certified), ethanol (EtOH, histological grade), hexadecane (Certified), toluene (Certified), chloroform (Certified) and methylene blue (MB) were obtained from Fisher Scientific. Genipin (98%, HPLC grade) was purchased from Wako Pure Chemical Industries, Ltd., and methyl orange (MO) was from EMD Chemicals. All chemicals were used as received. All aq. solutions and suspensions were prepared with water purified by the Millipore Milli-Q plus water purification system.

Characterizations. The morphologies of as-spun and crosslinked electrospun SPC/PVA (7:3, 9%) fibrous membranes were observed using a field emission scanning electron microscope (FE-SEM) (XL 30-SFEG, FEI/Philips, USA; Quattro, Thermo Scientific, USA) at a working distance of ca. 5 mm and an accelerating voltage of 5 kV. Each sample was mounted with conductive carbon tapes and sputter coated with gold/palladium before imaging. Widths of fibers were measured from 100 individual fibers and the mean and standard deviation were reported. Heated (12 h) membranes were blended (30 k rpm, 1 min) in water at 0.1%, and air-dried on the freshly peeled mica (Highest Grade V1 Mica Discs, 15 mm, Ted Pella, Inc.). Then both Leica DM2500 optical microscope equipped with the cross-polarizing filter and atomic force microscopy (AFM, MFP-3D, Oxford Instruments Asylum Research, Inc., Santa Barbara, CA) were applied for the imaging. AFM scanned in the tapping mode with OMCL-AC160 TS standard silicon probes (tip radius<10 nm, spring constant=28.98 N/m, resonant frequency of ca. 310 kHz, Olympus Corp.) at 1 Hz scan rate under the ambient condition.

Soy protein isolate (SPI) in water was successfully homogeneously dispersed as colloids at up to 9% by high speed blending (30 k rpm, 15 min). Aq. SP colloids (0.1%) were amphoteric, exhibiting ζ-potential ranging from −39.4 to +32.4 mV and an isoelectric point (PI) of 4.5.

The chemical composition and secondary structures of SPs in fibrous membranes were studied by Fourier transform infrared attenuated total reflection (FTIR-ATR) spectra collected from 3500 to 1000 cm$^{-1}$ at a resolution of 2 cm$^{-1}$ using a Nicolet iN10 microscope spectrometer (Thermo Fisher Scientific, USA) equipped with a liquid nitrogen cooled detector. The secondary structure composition, including α-helix (1645-1662 cm$^{-1}$), β-sheet (1613-1637 cm$^{-1}$, 1682-1689 cm$^{-1}$), β-turn (1662-1682 cm$^{-1}$), and random coil (1637-1645 cm$^{-1}$), was analyzed in the range of 1600-1700 cm$^{-1}$ (Liu, X.; Hsieh, Y.-L., Amphiphilic and amphoteric aqueous soy protein colloids and their cohesion and adhesion to cellulose. *Industrial Crops and Products*, 2019). X-ray diffraction (XRD) patterns were collected to study the crystalline structures of SPC cast film and electrospun PVA and hybrid fibers on a Scintag XDS 2000 powder diffractometer using a Ni-filtered Cu Kα radiation (=1.5406 Å) at an anode voltage of 45 kV and a current of 40 mA. Samples were compressed into 1 mm thick flat sheets between two glass slides and diffractograms were recorded from 5° to 40° at a scan rate of 2°/min. Peak deconvolution analysis was conducted using Peak Fit (Systat Software) and individual peaks were fitted by Gaussian functions with R$^2$>0.99 for all deconvolutions. The ratio of the total crystalline peak area and the sum of both crystalline and amorphous area was taken as the crystallinity index (CrI).

Thermal behavior of SPC cast film and electrospun membranes were measured using a Shimadzu thermal analysis system (TA-SOWSI), including a differential scanning calorimeter (DSC-60) and a thermo gravimetric analyzer (TGA-50). Both DSC and TGA were performed by heating at 10° C./min under flowing N$_2$ at a 50 mL/min rate to 400° C. The first derivative was derived from the TGA data and plotted as the DTG curve. The L* (lightness), a* (red to green) and b* (yellow to blue) color coordinates and K/S (absorption/scattering) values of as-spun and crosslinked hybrid fibrous membranes were measured using a Gretag Macbeth Color-Eye 7000A tester (Akron, Ohio, United States). All samples were sandwiched between two glass slides, measured at four different locations and the average reported. K/S values were calculated by Kubelka-Munk equation based on the spectral reflectance (R in %) of the samples as:

$$\frac{K}{S} = \frac{(1-R)^2}{2R}$$

The color strength (CS) was calculated by using the as-spun hybrid membrane as the standard:

Color strength (CS)=[(K/S)$_{sample}$/(K/S)$_{standard}$]×100%

The dry mass of each membrane before and after immersion in aq. media with pH of 0-10 for 1-14 d and air-drying at 65° C. was measured to 0.01 mg using an analytical balance (Shimadzu, AUW220D). Water contact angle (CA, 10 μL) on the surface of fibrous membranes was measured by the drop shape analysis method before the spreading of water droplets. Each membrane was measured 5 times in different locations to derive the average and standard deviation. The liquid (water, toluene, hexadecane, and octane, N=5) uptake of the as-spun and heat-treated (12 h) membrane was also weighed to report the average and standard deviation. The length, width and thickness swelling of the heat-treated membrane immersed in water for up to 2 h were determined by measuring with a vernier scale to the nearest 0.01 mm.

Adsorption and Desorption. The adsorption of cationic MB or anionic CBY on heat-treated (12 h) 7:3 SPC/PVA fibrous membrane was carried out by immersing ca. 100 mg adsorbent in 100 mL aq. MB (10-1000 mg/L) at pH 7 or CBY (10-200 mg/L) at pH 2 at ambient temperature, hand-shaking for 10 s then in a shaker (100-150 rpm) for up to 2 h. At predetermined time intervals, 0.5 mL solution was taken to quantify the amount of MB or CBY using Evolution 600 UV-vis spectrophotometer (Thermo Scientific) based on the calibration curve determined in the same aq. media. The percentage of MB or CBY removal was calculated as:

$$\text{Percentage of removal} = \frac{C_0 - C}{C_0} \times 100\%$$

where C$_0$ and C is the initial and current dye concentration, respectively. The amount of MB or CBY adsorbed at each time interval on the membrane, q (in mg/g), was calculated as:

$$q = \frac{(C_0 - C) \times V}{m}$$

where V is the solution volume and m is the mass of the membranes. The adsorption kinetics of MB on heat-treated membranes, i.e., t/q$_t$ (q$_t$, quantity adsorbed at time t) versus t plot, was fitted with both Lagergren's pseudo-first-order and Ho's pseudo-second-order models for physisorption and chemisorption, respectively, as well as Freundlich and Langmuir isotherms, typical of adsorption to heterogeneous and homogeneous surfaces, respectively. The recovery of MB and regeneration of the fibrous membrane (ca. 100 mg) was conducted in 5 repetitive adsorption-desorption cycles of 5 min adsorption of MB (20 mg/L, 100 mL) at pH 7, and 1 min desorption of MB at pH 2. Following each adsorption-desorption cycle, the membrane was thoroughly washed by acid (pH 2), then neutralized for the next cycle. The adsorption efficiency was evaluated based on dyes left in the solution and the desorption efficiency was derived from the dyes recovered. Selective absorption of either cationic MB or anionic methyl orange (MO) dye from 100 mL 1:1 w/w MB/MO mixture (20 mg/L) was studied at pH 7 and 2. Anionic MO was used in place of anionic CBY as CBY precipitated when mixed with MB.

Figures 8A, 8B, 8C, 8D, 8E, 8F:
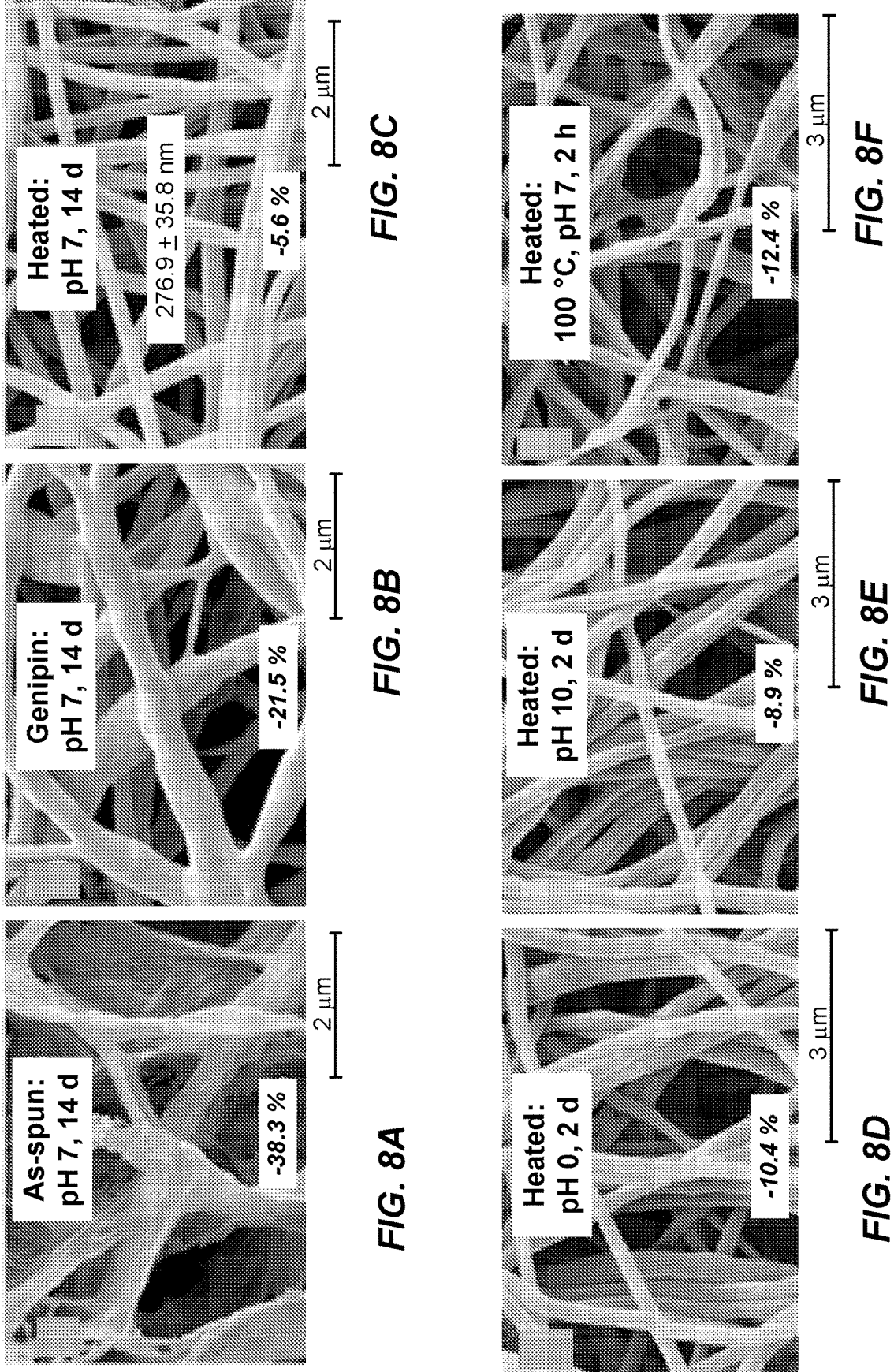
FIGS. 8A-8F show SEM images of electrospun SPC/PVA (7:3, 9%) fibrous membranes lyophilized after water immersion under different conditions and lengths of time.

Stability in Water. The stability of these fibrous membranes in water was observed by their mass and morphology (FIG. 8A-8F). The as-spun fibrous membranes lost substantial mass (36.9%) after 1 d and only 1.4% more after prolonged 14 d (FIG. 8A). The water-immersed membrane remained opaquely white after lyophilization, but their cylindrical fiber shapes were lost, deformed and merged (FIG. 8A). The genipin-reacted membrane lost less mass and more gradually, 10.8% mass after 1 d, then another 10.7% after 14 d, for a total of 21.5%, thus reduced dissolution of either or both SPs and PVA. The lyophilized membrane appeared pale blue, an evidence of genipin loss and the fibers merged (FIG. 8B), evident of reactions between genipin and SP amines. In contrast, the heat-treated membrane only lost 5.4% weight after 14 d in water and retained the same fiber morphology except for ca. 20% wider fibers (277±36 nm, N=100) (FIG. 8C). Most impressively, the heat-treated fibers remained essentially unchanged morphologically from extended 2 d immersions in strong acid (1 M HCl, pH 0) or base (0.0001 M NaOH, pH 10) and slightly deformed at boil for at least 2 h, losing respective 10.4, 8.9, and 12.4% weight (FIGS. 8D-8F). The heat treated membrane was dispersed into single fibers by high speed blending (30 k rpm, 1 min), then air-dried and imaged by AFM to show excellent shape retention from shear force and average root mean squared (RMS) roughness of 118.5±23.6 nm became significantly more hydrophobic with an average water CA of 110.5° (Table 3) while the bulk of the membrane remained amphiphilic, absorbing similar quantities of both water (20.5 mL/g) and non-polar solvents (15.5-23.4 mL/g) (Table 3). The heat-induced hydrophobicity is consistent with dehydration reactions among polar —OH, —COOH and —NH$_2$ groups into less polar amide and non-polar esters. Lengthening the heat treatment to 48 h only slightly increased the water CA to 119.8±1.8°, possibly due to further condensations.

TABLE 3

Liquid contact angle (CA) and absorption of as-spun and heat-treated membranes
(N = 5)

| Liquid | Surface tension (mN/m) | Dielectric constant | Density (g/cm³) | As-spun | | | Heated | | |
|---|---|---|---|---|---|---|---|---|---|
| | | | | CA (°) | mL/g | g/g | CA (°) | mL/g | g/g |
| Water | 72.8 | 80.3 | 0.997 | 39.2 (±1.6) | 21.2 (±0.7) | 21.1 (±0.7) | 110.5 (±6.4) | 20.5 (±1.6) | 20.4 (±1.6) |
| Toluene | 28.4 | 2.4 | 0.867 | 0 | 7.1 (±0.7) | 6.2 (±0.6) | 0 | 15.5 (±2.2) | 13.4 (±1.9) |
| Hexadecane | 27.5 | 2.1 | 0.770 | 0 | 8.8 (±0.9) | 6.8 (±0.7) | 0 | 23.4 (±4.4) | 18.0 (±3.4) |
| Octane | 21.6 | 2.0 | 0.703 | 0 | 9.4 (±1.1) | 6.6 (±0.8) | 0 | 16.2 (±2.4) | 11.4 (±1.7) |

(N=5) corresponding to the aggregated SPs and the desirable higher specific surface for sorption applications. The excellent integrity of heated fibers following prolonged aq. immersions under extreme pH and at boil or strong shear force with limited mass loss of 5.4 to 12.4% confirms the effectiveness of heating in crosslinking SPs and possibly with PVA.

Figure 4A:
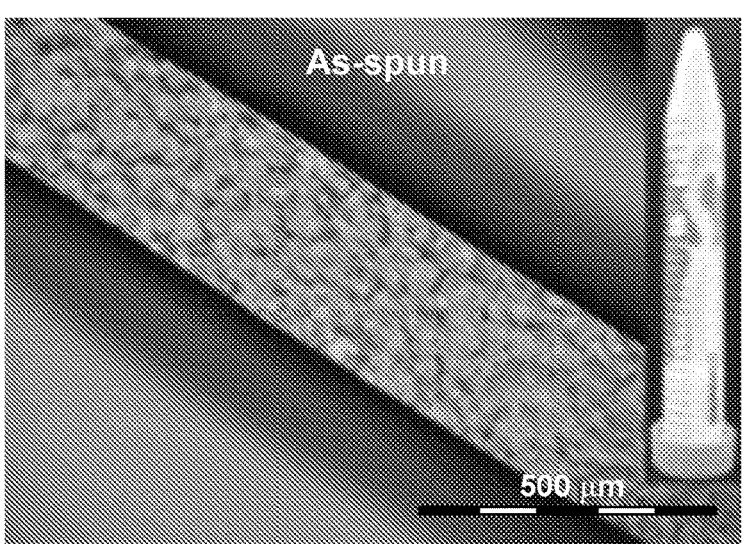
FIGS. 4A-4E show optical microscopic images of SPMF-HIPE gel fibers wet spun from the 25/75 v/v aq. SPMF/SA (2:1, w/w, 2%)/hexadecane using a 27 G syringe at a feeding rate of 90 mL/h into aq. 0.5 M CA$^{2+}$.
Figure 4B:
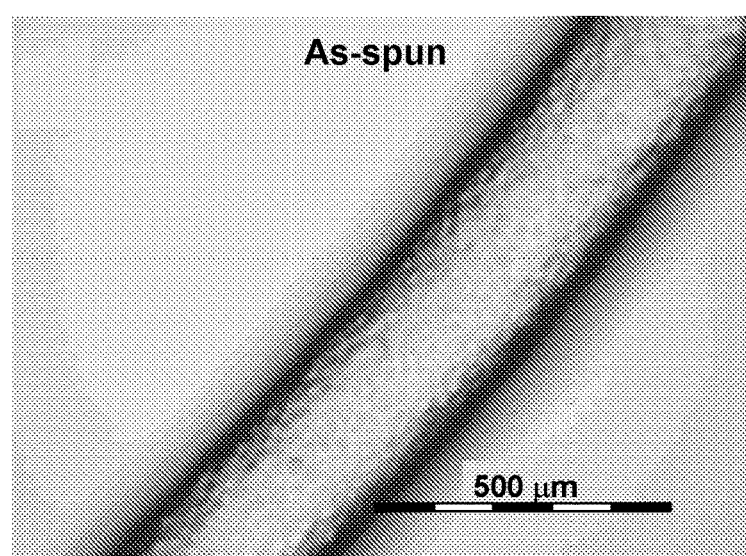
Figure 4C:
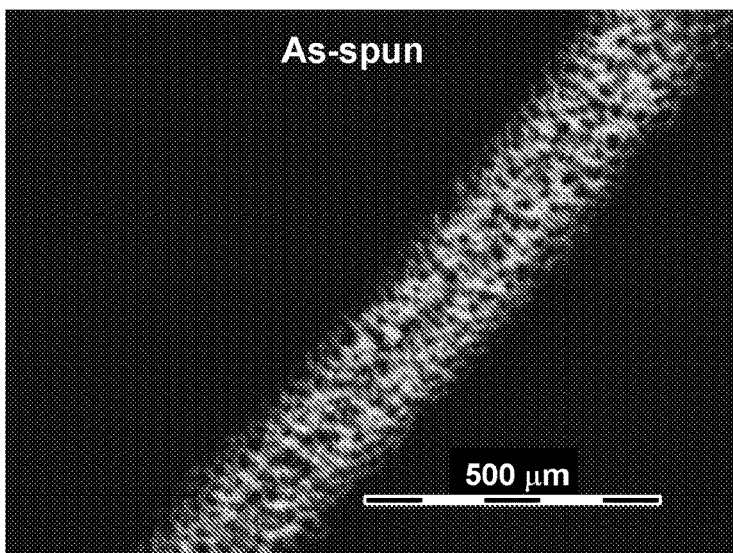
Figure 4D:
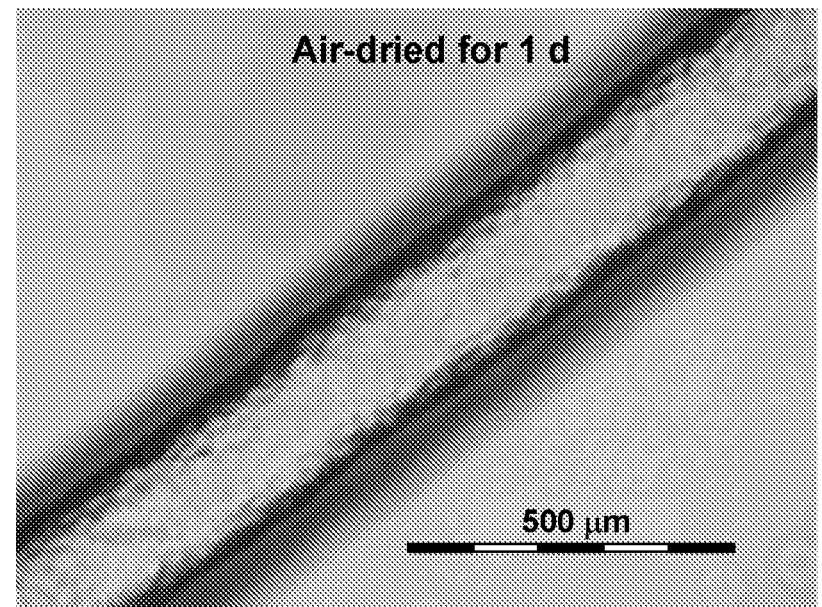
Figure 4E:
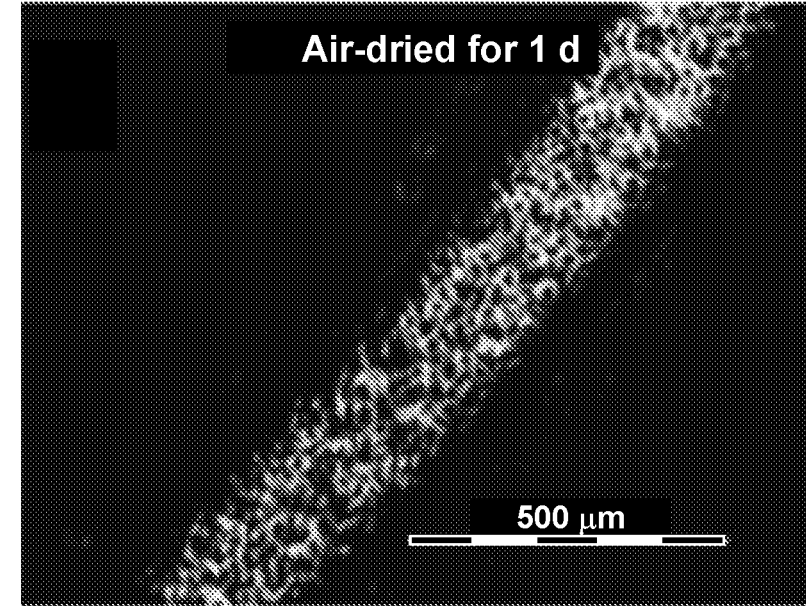
Figure 5B:
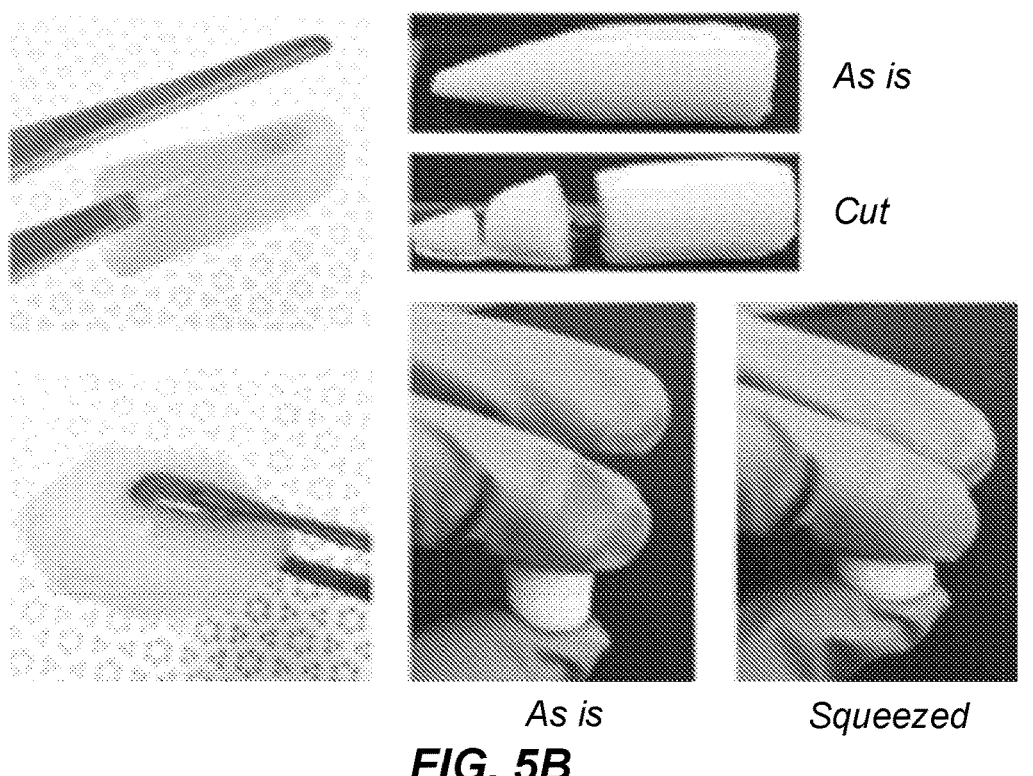
Figure 5C:
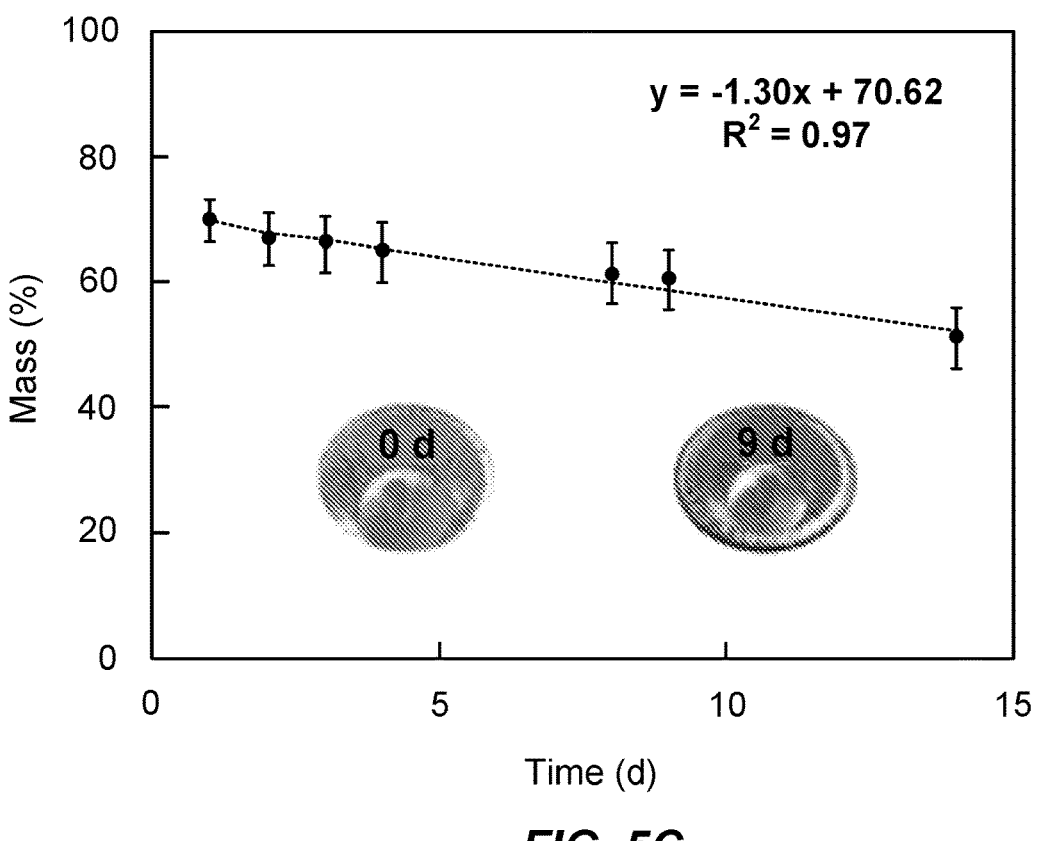
Figure 9A:
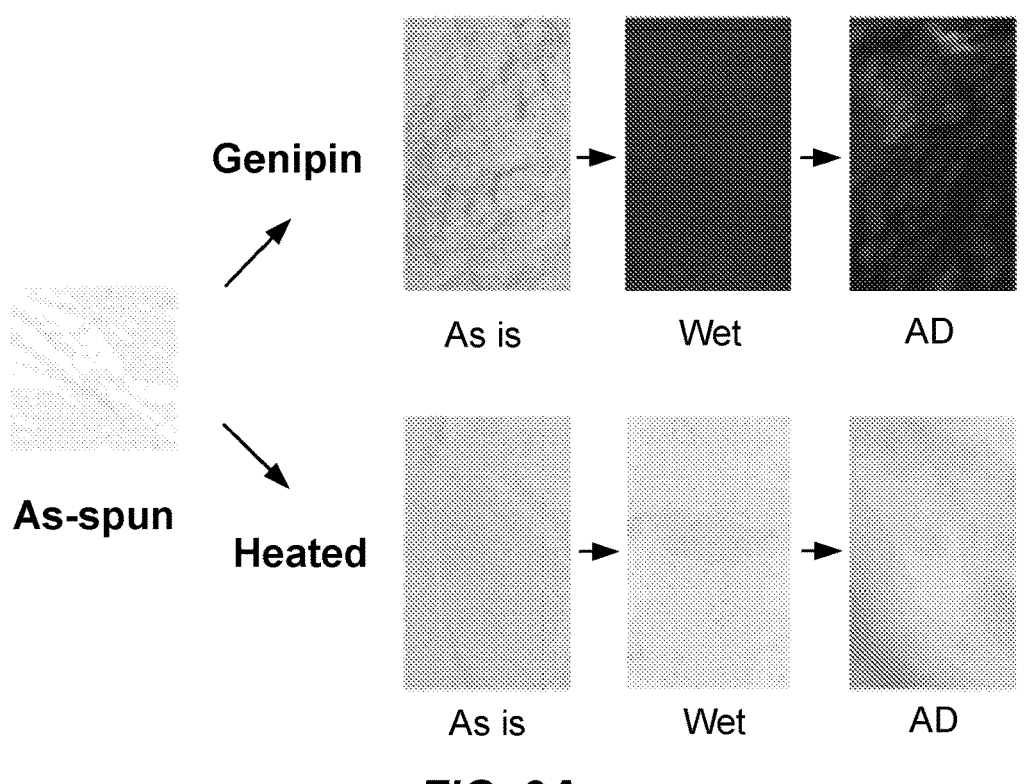
FIGS. 9A-9D show the as-spun, genipin-crosslinked (65° C., 1 h) and heated (150° C., 12 h) SPC/PVA (7:3, 9%) fibrous membranes.
Figure 9B:
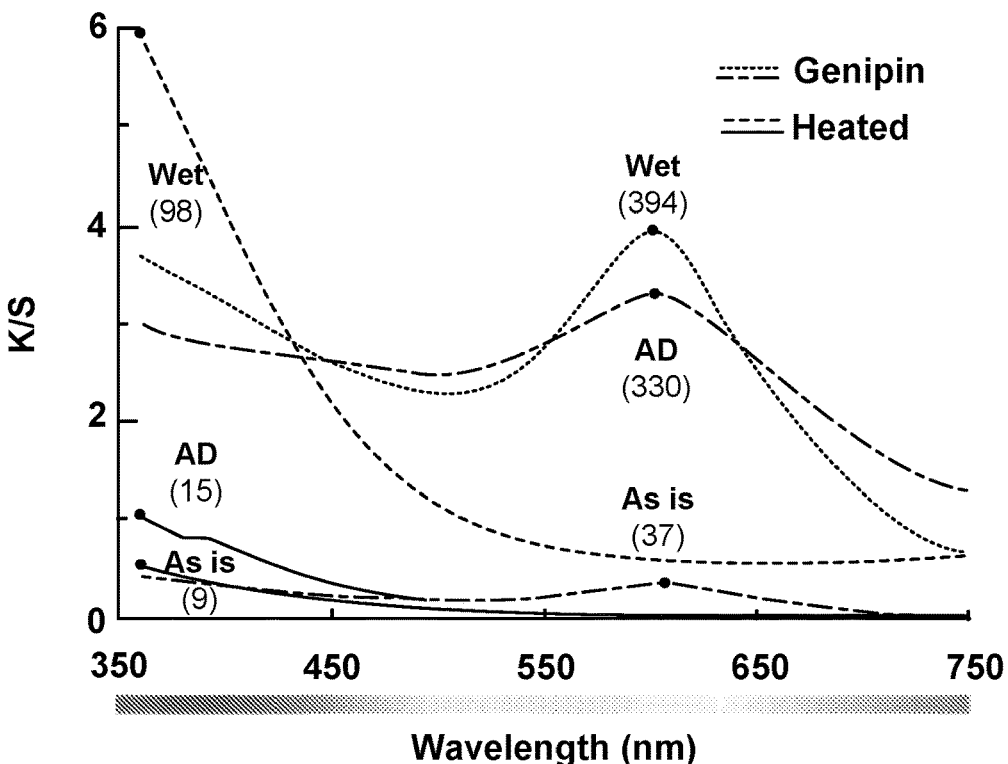
Figure 9C:
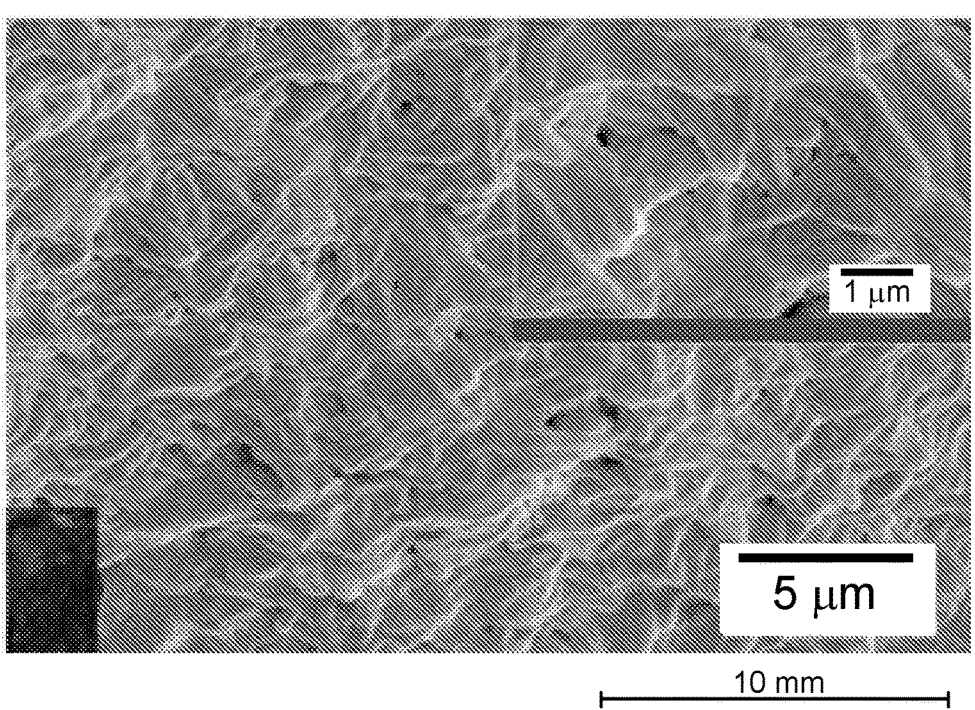
Figure 9D:
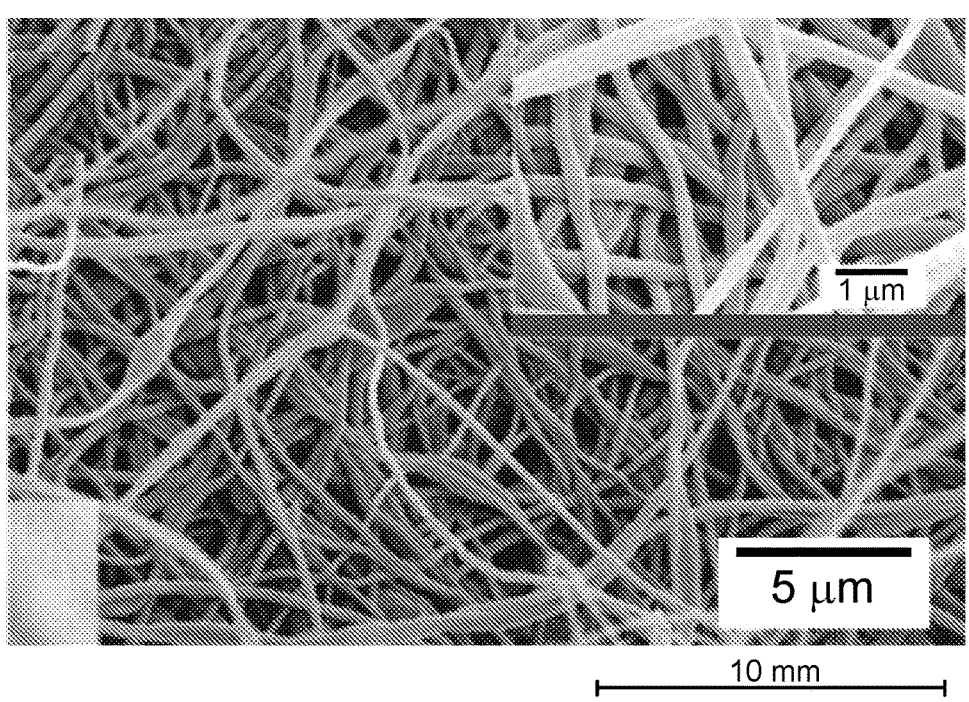

Color Change in Wet and Dry State. The as-spun fibrous membranes appeared opaquely white, became translucent and gel-like when wet by water, then translucent pale yellow and film-like when air-dried, losing most of fibrous features. Both genipin and heat-treated SPC/PVA fibrous membranes showed remarkable changes in colors and color strength (CS) when saturated with water (FIGS. 9A-9B). The genipin reacted membrane turned from pale blue (CS=36) into dark blue (CS=394) once wet by water and remained dark blue (CS=330) when air-dried into a thin film (FIG. 4A-4C). The heat-treated membranes were khaki (Ch=9) in color and became orange (CS=98) when wet, then reversed back to similarly khaki (CS=15) when air dried (FIGS. 4A, 4B and 4D). Therefore, the color changes to the respective orange and dark blue colors of both genipin and heat-treated membranes can signal the presence of water, but only the heated membrane remained fibrous and could return to the original color upon air-drying, reversible for a few times, giving another clear evidence of sufficient crosslinking and water stability of the heat-treated fibrous membranes.

Figure 10A:
FIGS. 10A-10C show dye wetting and absorption on heat-treated electrospun SPC/PVA (7:3, 9%) fibrous membranes.

Rapid and Selective Adsorption and Desorption of Ionic Dyes. The as-spun membranes were wettable by water, having an average water CA of 39.2° and absorbing 21.2±0.7 mL/g (N=5) water and even more readily wettable by non-polar toluene, hexadecane and octane, but absorbed much less (7.1-9.4 mL/g) of these low-surface-tension liquids and lost almost no mass (Table 3). The as-spun membranes were clearly amphiphilic on their surfaces, but more hydrophilic in the bulk and in fact partially water soluble, losing over one third of mass and fibrous structures as observed earlier. The 12-h heat treated membrane surface Wetting and adsorption of aq. cationic MB and anionic CBY as well as lipophilic Sudan IV in hexadecane wet the fibrous membranes and was absorbed differently under the neutral condition. Aq. MB and CBY droplets (10 μL) wetted the as-spun membrane within 3-5 s and water in both dye solutions spread to wet larger areas than the initial droplets. However, cationic MB only colored the original footprint of the droplet whereas anionic CBY spread nearly to the edge of the wetted area (FIG. 10A). That swift affinity of cationic MB over the anionic CBY to the as-spun membrane indicates its more negatively charged nature. The heat-treated membrane also showed similarly higher affinity to cationic MB than anionic CBY (not shown), but took longer to wet, i.e., 10 s or a few minutes for that heated for 12 or 48 h, respectively, indicative of the increased hydrophobicity while remaining more negatively charged. The one heated for 48 h even caused the aq. CBY to bead up (FIG. 10A, right), but insufficiently hydrophobic to adsorb lipophilic Sudan IV in hexadecane.

Figure 10B:
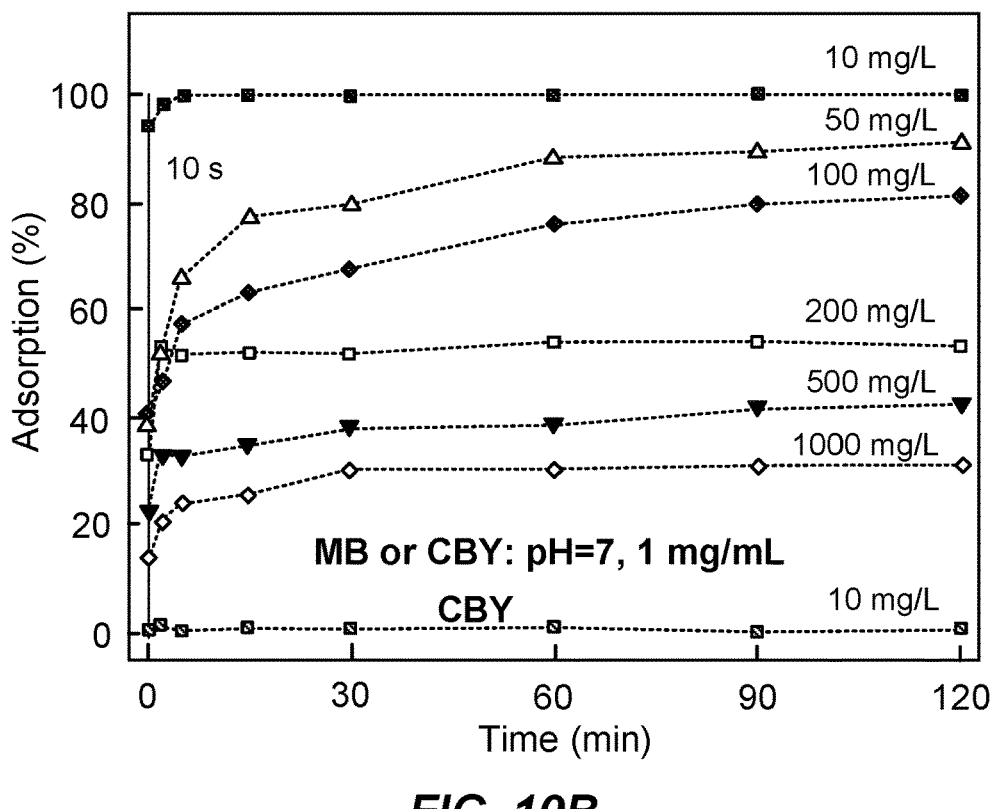
Figure 10C:
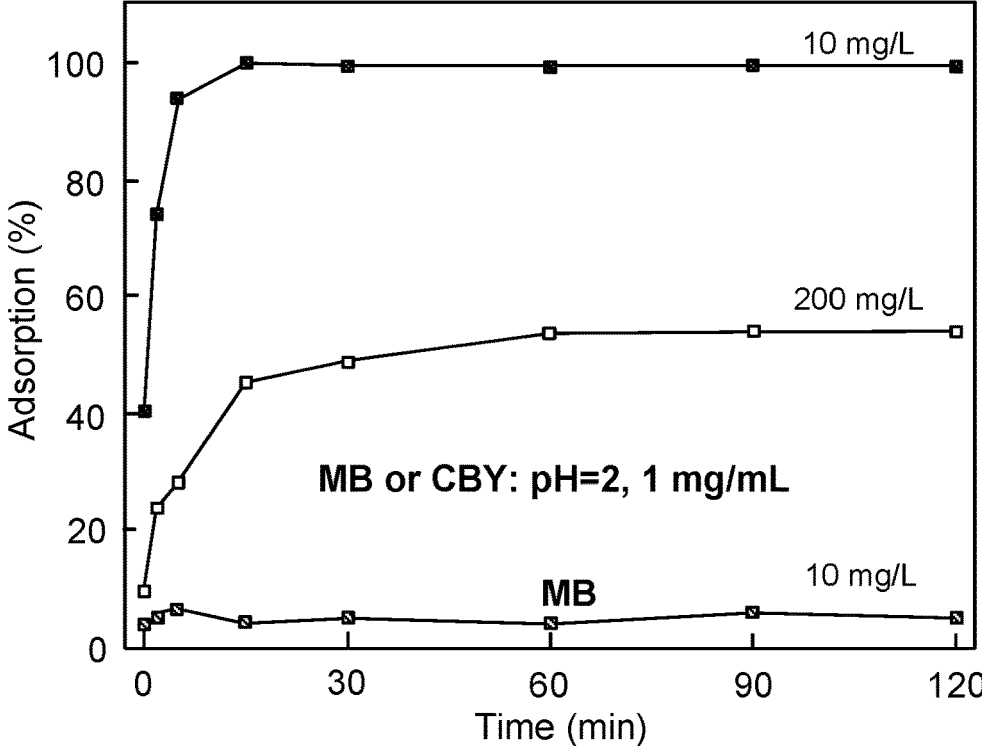

The pH-dependent amphoteric characteristics of the heat-treated fibrous membranes were further demonstrated by the adsorption of cationic MB and anionic CBY under neutral and acidic (pH 2) conditions, respectively. At pH 7, above the PI of SPs (pH 4.5), the fibrous membrane was negatively charged and adsorbed cationic MB rapidly to remove 94.3% from the 10 mg/L mixture in 10 s but adsorbed only 9.9% CBY (FIG. 10B). At pH 2, 94.0% of anionic CBY in the 10 mg/L mixture was adsorbed in 5 min while only 6.2% MB was adsorbed (FIG. 10C). Again, the distinct pH-dependent and switchable electrostatic binding preference toward ionic species of the heated membrane is attributed to deprotonation of —COOH at neutral or protonation of —NH$_2$ groups at pH 2, i.e., above and below the PI. With increasing initial concentrations of 50, 100, 200, and 1000 mg/L, the MB absorbed decreased, i.e., 91.3, 81.4, 54.2, and 31.1%, respectively, and levelled off ca. 15 min at lower 10-200 mg/L and ca. 30 min at higher 500-1000 mg/L concentrations (FIG. 10B). Total MB adsorbed per gram of the heat-treated membrane increased with initial concentrations, i.e., from 10.5 to 311.3 mg at 10-1000 mg/L initial concentrations. In the case of anionic CBY (200 mg/L), the total removal (54.0%) at pH 2 was similar to that of cationic MB (54.2%) at pH 7, although taking much longer ca. 60 min to reach equilibrium (FIG. 10C). While the maximum adsorption capability (312.5 mg/g, pH 7) of heat-treated (12 h) fibrous membranes is similar to values reported on some activated carbons (9.8-980 mg/g, 0.1-1 h), the most significant distinction is in its short 0.5 h time to reach equilibrium, far shorter than fibers electrospun from other proteins and/or synthetic polymers, i.e., 6 h by keratin (170 mg/g, pH 6), 2 h by sericin/β-cyclodextrin/PVA (2:1:7, 187 mg/g, pH 8), and 6 h by β-cyclodextrin/poly(acrylic acid) (5:1, 826 mg/g, pH 9) and most agricultural and industrial wastes (0.84-472.1 mg/g, ca. 0.5-24 h).

The MB adsorption data on heat-treated membranes showed a significantly higher correlation coefficient $R^2$ values of >0.99 in Ho's pseudo-second-order model than the merely 0.47-0.70 in Lagergren's pseudo-first-order model. Therefore, the overall MB adsorption is confirmed to be mainly controlled by chemisorption instead of physisorption. The adsorbed MB quantities also showed a better fit of Freundlich isotherm with the $R^2$ of 0.9879 over the Langmuir isotherm ($R^2$=0.9269) to support more heterogeneous adsorption of MB onto on the fiber surfaces where the —COOH and —$NH_2$ groups are randomly distributed.

Figure 11A:
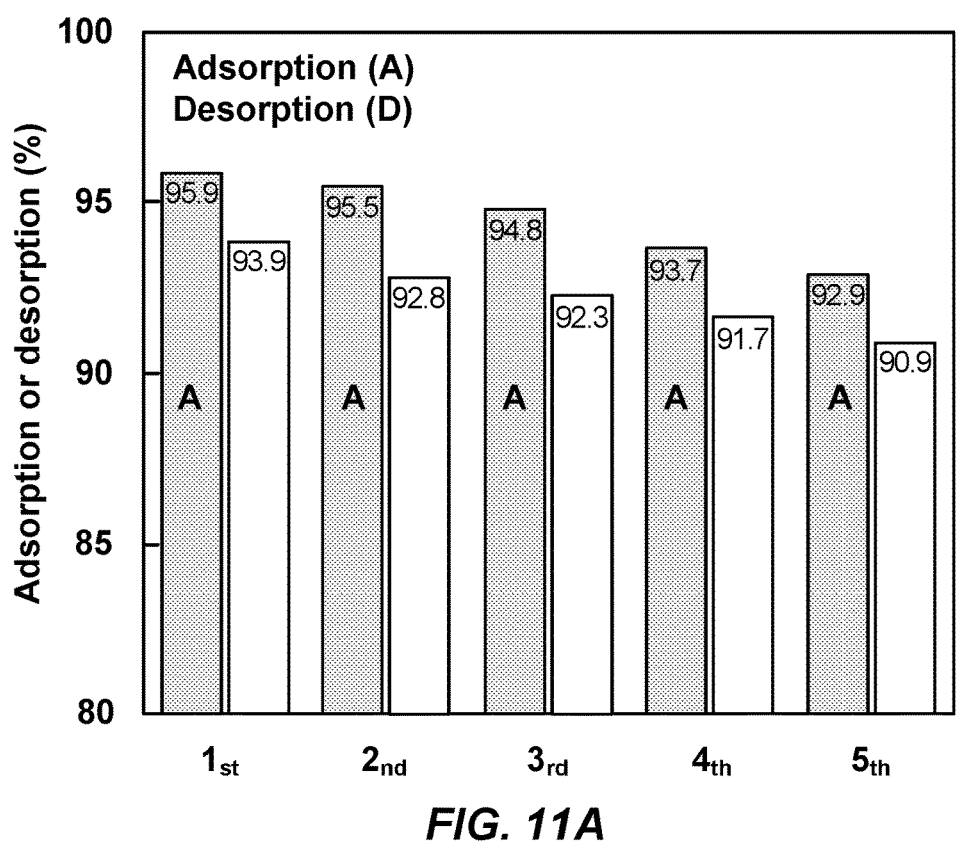
FIGS. 11A-11D show repetitive and selection dye adsorption on electrospun SPC/PVA (7:3, 9%) heat treated (150° C., 12 h) fibrous membranes (100 mg) at fixed 1 mg/mL membrane:dye ratio.
Figure 11B:
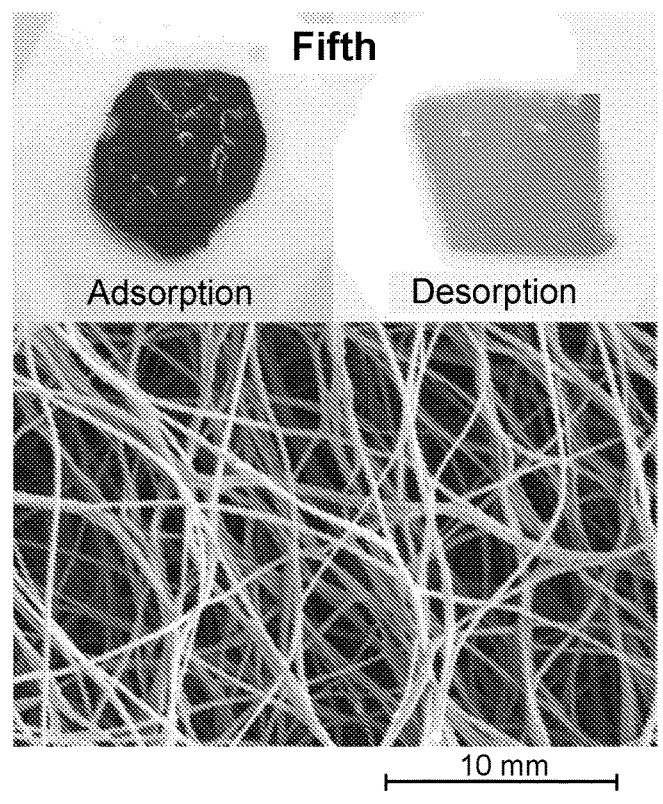
Figure 11C:
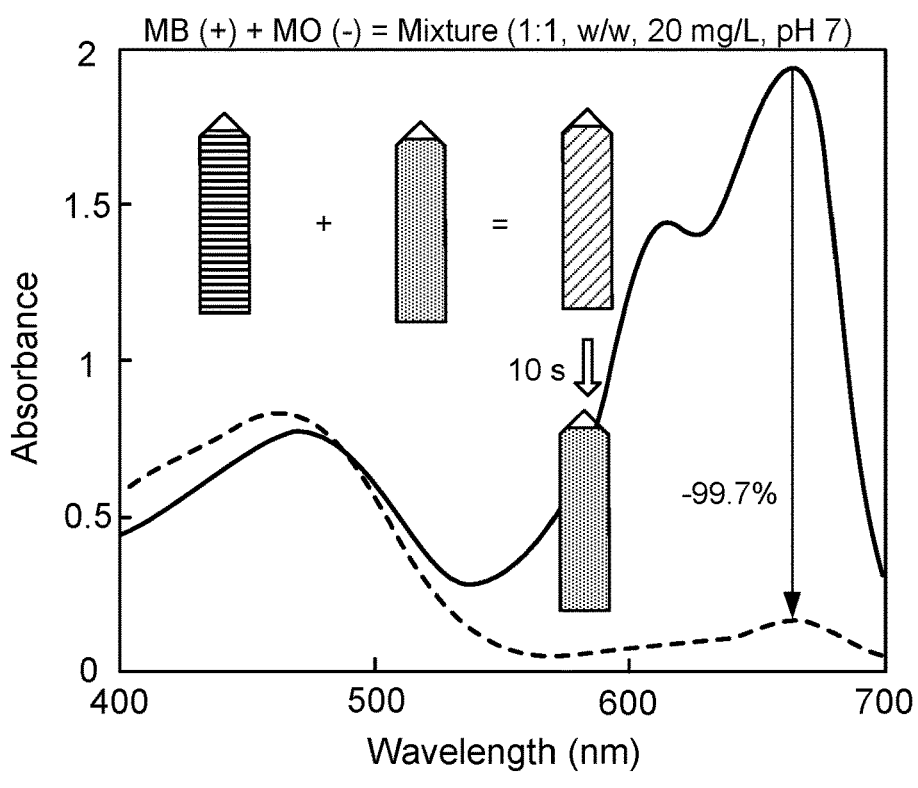
Figure 11D:
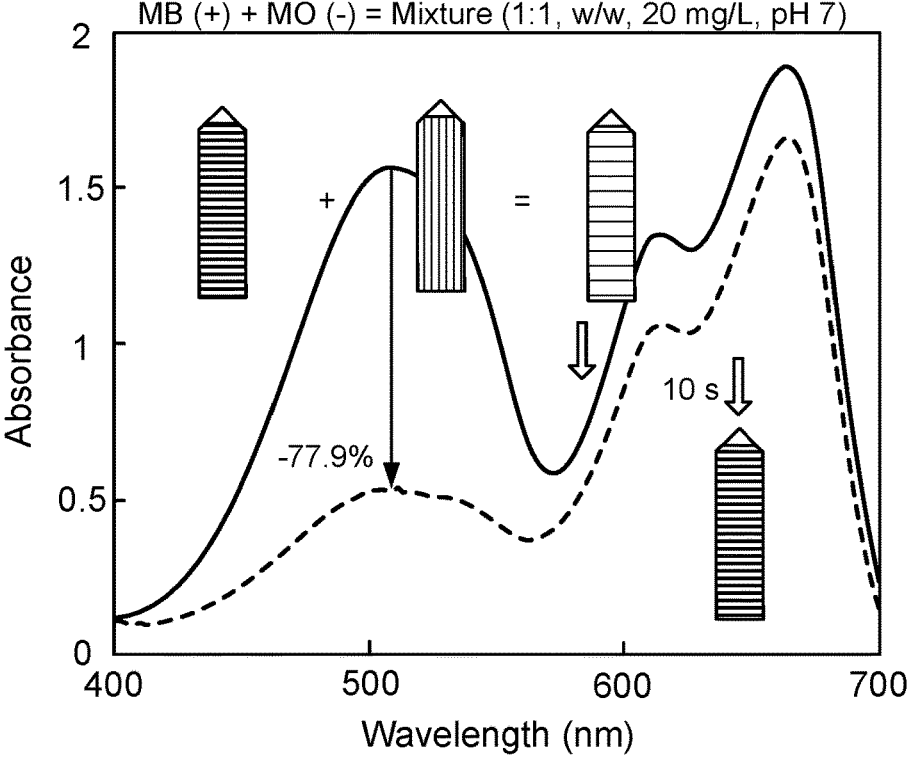
Figure 12:
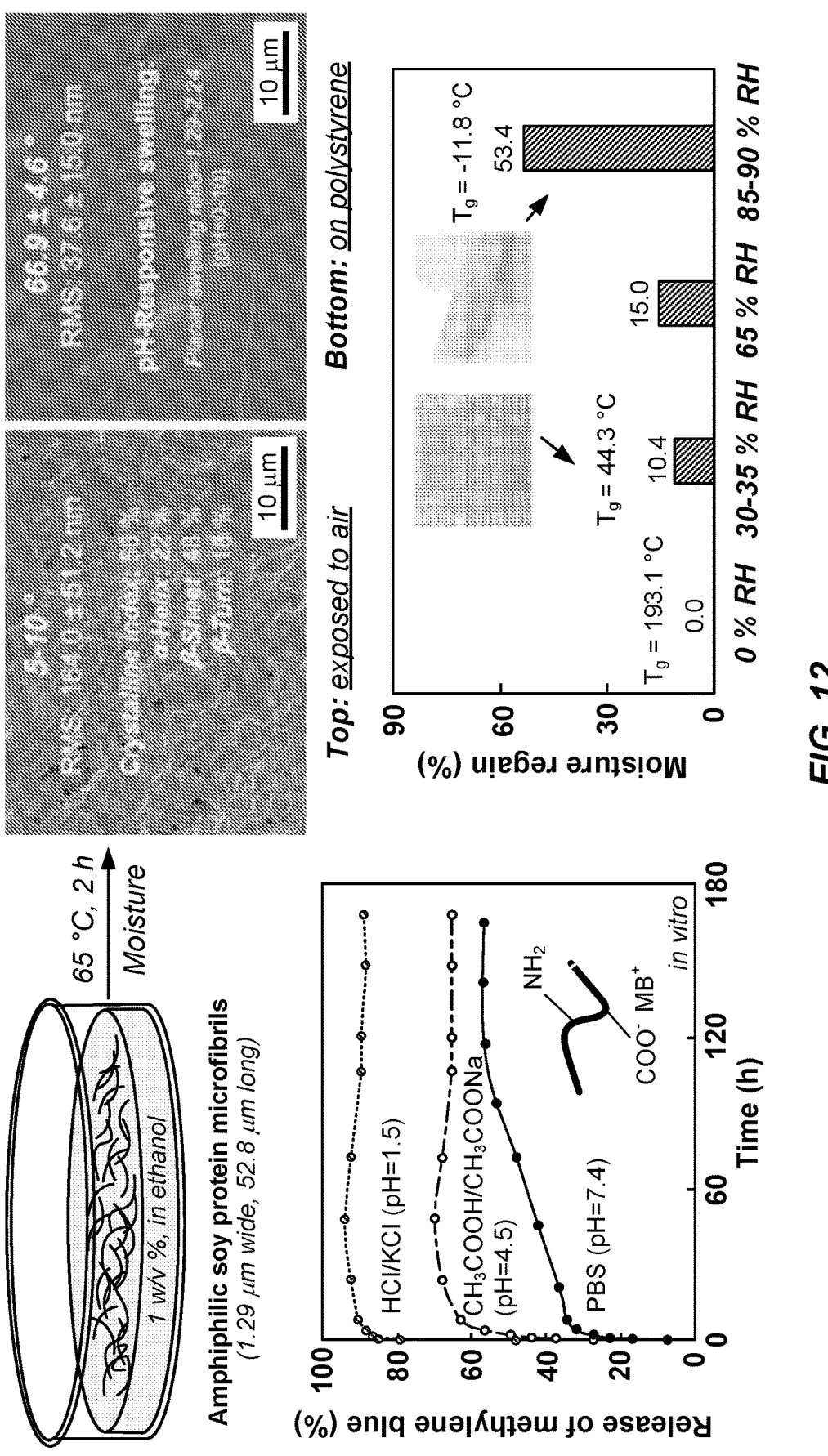
FIG. 12 shows a summary of the properties of the soy protein films.

The five cyclic MB desorption-desorption of heat-treated membranes showed 93-97% was adsorbed in 5 min and 91-94% of MB desorbed within 1 min, turning the dark blue membrane into the original dark yellow color (FIGS. 11A-11B). MB adsorption and desorption were over 90% in all 5 cycles while the membranes retained their fibrous morphologies (FIGS. 11A-11B), validating the feasibility of recovering MB and regenerating membranes for practical repetitive adsorption-desorption applications.

Figure 6A:
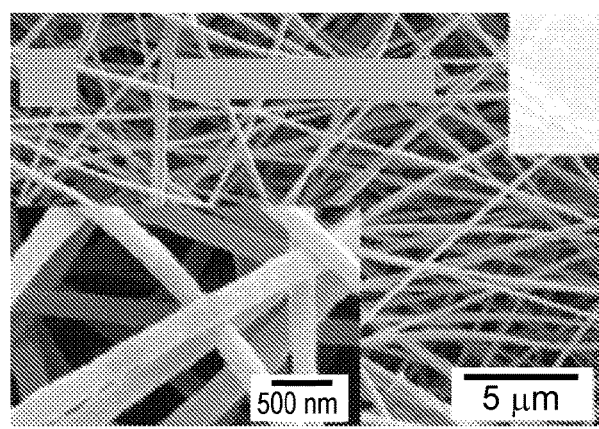
FIGS. 6A-6D show SEM images of electrospun SPC/PVA fibrous membranes.
Figure 6B:
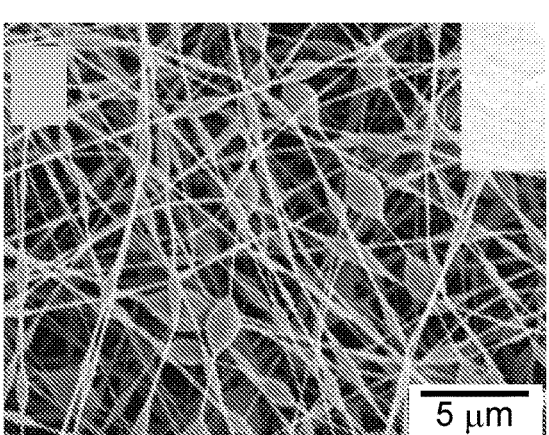
Figure 6C:
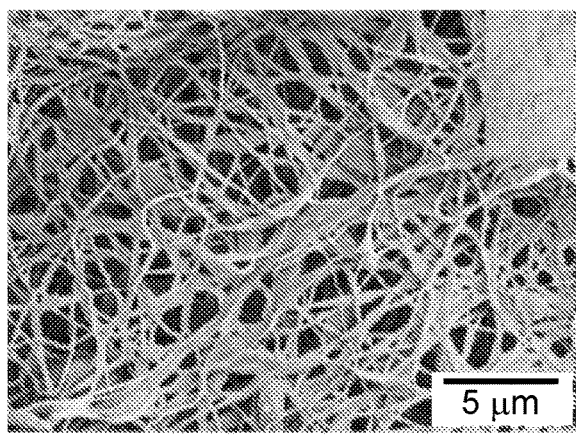
Figure 6D:
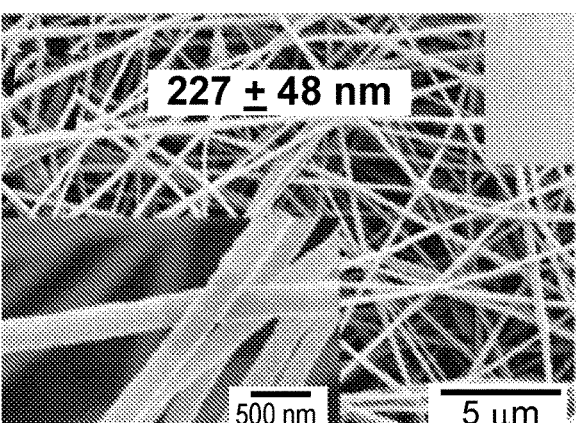

Under neutral condition, it took only 10 s for the anionically charged membrane to remove 99.7% of the cationic MB from the 1:1 MB/MO mixtures, turning the clover green mixture into lemon yellow and leaving 89.9% anionic MO (FIG. 6C). At pH 2, the positively charged fibrous membranes selectively adsorbed 77.9% anionic MO within 10 s, leaving a blue solution containing 79.7% MB (FIG. 6D). While selective adsorption took only seconds in both cases, low extents of the oppositely charged dyes, i.e., ca. 10% MO and 20% MB, were also adsorbed in due process, indicating very high but not absolute selectivity. Nevertheless, the unique pH-dependent amphoteric characteristics as demonstrated by selective binding of cationic and anionic dyes demonstrate the potential of these SP fibrous membranes for applications in separation and recovery of oppositely charged ionic species.

Example 4: Method of Preparing the Soy Protein Fiber Membrane

Electrospinning. Aq. soy protein (SP) suspensions were prepared by adding 9% crude SPI in water under constant magnetically stirring for 1 h at ambient temperature, followed by either adjusting the pH to 12 using 1 M NaOH then heated at 90° C. for 45 min or treating in the opposite order. Aq. SP colloid (SPC) was the supernatant from blending 9% SP suspensions at 30 k rpm for 15 min using a high-speed blender (Vitamix 5200), cooled to ambient temperature, then centrifuged at 5 k rpm for 15 min. Aq. PVA solutions were prepared at 9 or 12% by heating at 95° C. for 6 h under constant stirring and then cooled to ambient temperature. All concentrations were in wt % and expressed as % throughout.

Electrospinning was performed using mixtures of either magnetically stirred (ca. 2 k rpm, 1 h) 9% SP suspension or SPC with 9% PVA at 1:1, 7:3 and 9:1 w/w ratios. Each mixture was loaded into a 30 mL horizontally placed syringe (Popper & Sons, Inc.), fed at 0.01-2 mL/h using a syringe pump (KDS 200, KD Scientific, USA) through a flat-end metal needle (21 gauge) and electrospun at 15 kV operated with a DC power supply (ES 30-0.1 P, Gamma High Supply, USA). The fine fibrous membranes were collected on a vertically placed aluminium foil (30 cm×30 cm) at 25 cm from the needle tip to reach a typical thickness of 150-200 μm.

Aqueous (aq.) 9% SP control suspension that was magnetically stirred for 1 h phase separated in hours and could only be electrosprayed into droplets. Adding equal mass of 9% PVA to the aq. SP control enabled electrospinning only at a very low 0.01 mL/h rate and produced mostly beads with very few fibers, while dripped continuously. Heating (90° C., 45 min) aq. SP control caused gelation that was attributed to denaturation or the unfolding of globular structures to reduce exposure of hydrophobic moieties to water. Following pH adjustment to 12, the gel became miscible with equal mass of PVA, but still generated mostly beads stringing along thin fibers. Treating aq. SP control in the reverse order, i.e., adjusting pH to 12 then heating at 90° C. for 45 min, enabled continuous electrospinning of 1:1 SP/PVA mixture at 1.5 mL/h for at least 20 h without any dripping into a white membrane composed of uniform, straight and smooth fibers with the average diameter of 267 nm (±65 nm, N=100). Heating the basic adjusted SP control also enable electrospinning with less PVA, but 7:3 SP/PVA(9.75%)\ fibers were irregular in widths and among lots of beads and splashes. This mixture also phase separated in 7-8 h to prevent continuous electrospinning. Both the heterogenous electrospun products and phase separation indicated the instability of the mixture.

In contrast, aq. SP colloid (SPC), the supernatant from high speed blending, mixed with PVA at 7:3 mass ratio could be facilely electrospun at 1.5-2 mL/h feeding rate continuously for at least 20 h. The fibrous membrane appeared white initially, then became pale yellow when thickened. Fibers were uniform in 231 nm (±46 nm, N=100) width with slightly angulated surfaces (FIG. 6A). Further increasing SPC in the mixture to 90% could also be electrospun continuously but beads were observed regularly spaced along much thinner fibers (FIG. 6B). The significantly improved electrospinnability of SPC mixtures is attributed to the surface-active behavior of aq. SPCs that have shown to reduce the surface tension of water to 41.2 mN/m at above 0.98%. The presence of residual salts from alkali extraction and acid precipitation of SPI isolations may also increase the net charge density to aid electrospinning. These most uniform 7:3 SPC/PVA hybrid fibrous membranes were therefore selected for further studies and denotes simply as fibrous membranes from here on.

Genipin Crosslinking and Heat Treatment. Electrospun SPC/PVA (7:3, 9%) fibrous membranes (ca. 100 mg) were chemically reacted with genipin or heat treated to improve aq. stability. Chemical crosslinking with 11 mM genipin in 1:1 v/v EtOH/water was performed by either complete submersion in genipin in open Petri dish to expose to ambient oxygen for 24 h or saturation with ca. 600 mg genipin solutions in a sealed centrifuge tube at 65° C. for 1 h. Following each process, the membrane was thoroughly washed with EtOH and water in sequence, frozen at −20° C.

for 1 h, and then lyophilized at −50° C. for 24 h in a freeze-drier (Free Zone 1.0 L Benchtop Freeze Dry System, Labconco, Kansas City, MO). Electrospun SPC/PVA (7:3, 9%) fibrous membranes were heated at 150° C. under vacuum (ca. 20 Hg) for 12 or 48 h and cooled to ambient temperature.

The 7:3 SPC/PVA fibrous membranes were chemically crosslinked with 11 mM genipin in 1:1 v/v EtOH/water under two conditions or heat treated (150° C., 12 h). Complete submersion in genipin solutions at ambient temperature turned the top of the membrane yellowish initially, then some pale blue spots appeared after 5 h, and all dark blue after 24 h; while the bottom remained pale blue, probably due to the lack of access to oxygen. The membrane saturated with genipin solutions at 65° C. appeared bluish in 15 min, then dark blue on both sides in 30-60 min and, upon lyophilization, became a pale blue and fluffy mass of irregularly sized, deformed and merged fibers (FIG. 6C). The heat-treated membrane, on the other hand, retained the same fiber sizes (227±48 nm, N=100) and morphology, but became slightly pale brown (FIG. 6D). The brownish color may be attributed to the formation of Melanoidins pigments via Maillard reactions between amines of SPs and carbonyl groups of reducing sugars, i.e. glucose and lactose, known to be present in SPI. Primary amines of SPs may either react with the genipin ester group via $SN_2$ nucleophilic substitution to form secondary amides or attack the olefinic C-3 carbon of genipin nucleophilically to open the dihydropyran ring to heterocyclic tertiary amine intermediate 1, then into intermediate 2 after removing the C-10 hydroxyl. Aided by oxygen radicals, these intermediates have shown to polymerize into blue color products that are commonly recognized as indication of successful genipin crosslinking of proteins. The significantly darker and uniformly blue fibrous membranes from reaction with genipin at 65° C. for merely 1 h provided clear evidence of crosslinking and was further studied.

Figure 7A:
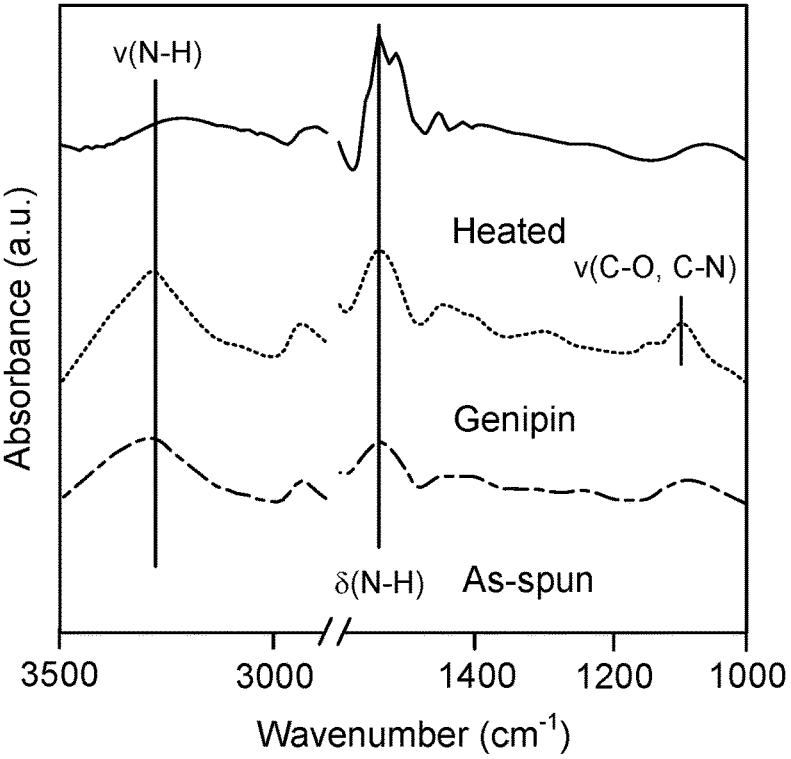
FIGS. 7A-7C show characterization of SPC/PVA (7:3, 9%) as-spun, genipin-crosslinked (65° C., 1 h) and heated (150° C., 12 h) fibrous membranes.

None of the bonds expected from genipin crosslinking reactions could be discerned on the FTIR-ATR spectra due to their overlapping with C N and C—O stretch of SPs and PVA at 1090 cm$^{-1}$ and genipin characteristic peaks at 1443 and 1080 cm$^{-1}$ (FIG. 7A). Whereas the heat-treated membrane exhibited a significantly reduced peak at 3362 cm$^{-1}$ (N—H and O—H stretchings, FIG. 7A), consistent with the amidation and esterification of the —NH$_2$, —COOH, and —OH among SPs and possibly esterification between SPs and PVA. Analyses of FTIR amide I bonds in fibers electrospun from SPC as well as those reacted with genipin or heat treated all showed very high extents (86-89%) of the ordered α-helix and β domains, 18-21% higher than those electrospun from pH adjusted then heated SP suspensions (not shown). X-ray diffraction diagrams also confirmed that all fibrous membranes were similarly semi-crystalline with the crystalline index (CrI) of 60.8-66.8%.

Figure 7B:
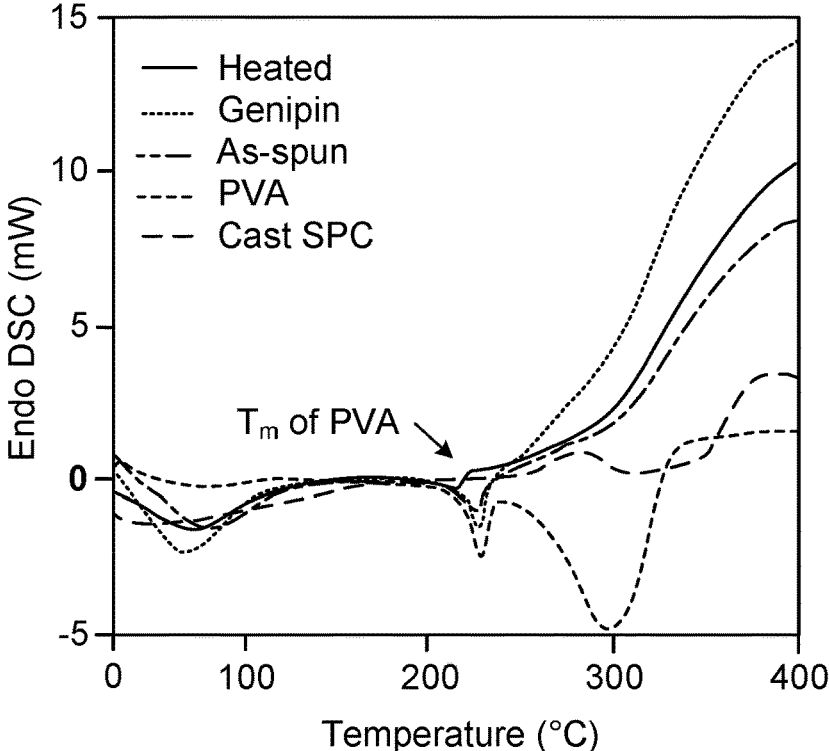
Figure 7C:
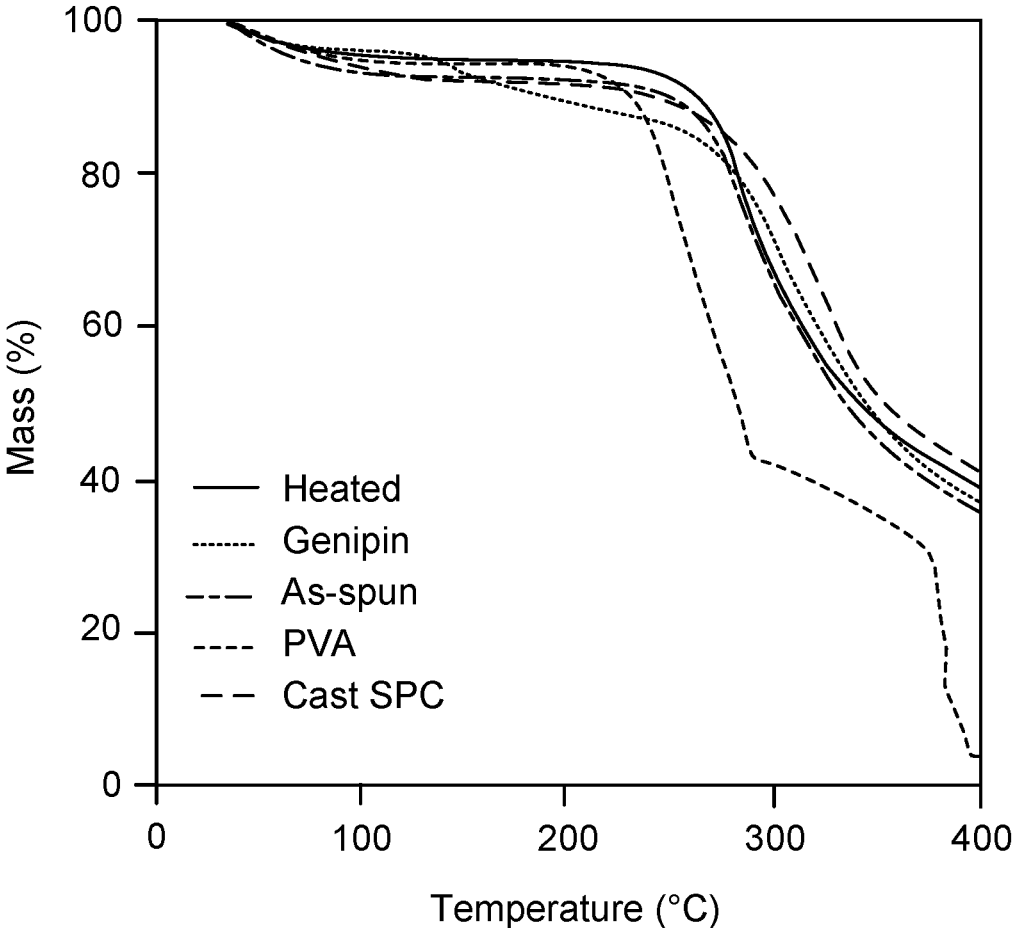

A similar PVA melting endotherm (ca. 227° C., 29.7-45.1 J/g) was observed in as-spun and genipin-reacted fibrous membranes as in electrospun PVA (228° C., 55 J/g), but with lowered endotherm and broad exotherms above 210° C. (FIGS. 7B-7C). The peak decomposition temperature in both genipin (298° C.) and heat (287 and 313° C.) treated samples was distinctively higher than that of as-spun membranes (284° C.), indicating the improved thermal stability, although their weight losses at 400° C. was similar (51.7-56.5%, FIG. 7C). These data confirmed both genipin reaction (65° C., 1 h) and heat treatments (150° C., 12 h) improved thermal stability of the hybrid membranes.

Homogeneous and stable aq. SP colloids have been facilely produced by high speed blending (30 k rpm, 15 min) of SPI and robustly electrospun into SP-rich fibrous membranes of uniform ultra-fine fibers in 231 nm average width. While both chemical reaction with genipin or heat treatment could render the SP-rich fibrous membrane water-insoluble, the heat treated membranes were particularly wet resilient, retaining 90% mass and essentially same fibrous morphologies from prolonged aq. exposure under neutral (pH 7, 14 d), extremely acidic (pH 0, 2 d) and basic (pH 10, 2 d) conditions, as well as boiling (2 h) and mechanical blending (30 k rpm, 1 min). This simple and effective approach of mechanical shear force to stable SP colloids and heat crosslinking to fabricate wet-resilient fibrous membranes is the first for globular proteins without needing any surfactants, alkali or urea as reported by others previously. Furthermore, the heat treatment turned the hydrophilic (39° water CA) surfaces of as-spun membranes to hydrophobic (111° water CA) while the bulk remained amphiphilic, capable of absorbing similar amounts of water and nonpolar liquids. These amphoteric SP-rich fibrous membranes could be simply deprotonated to carry negative (—COO$^-$) charges under neutral or protonated to be positively (—NH$_3$$^+$) charged under acidic (pH 2) conditions to selectively adsorb cationic MB or anionic CBY and MO dyes via electrostatic interactions. The adsorption of MB at pH 7 was rapid and reached the equilibrium in 15-30 min, absorbing 31-91% at 50-1000 mg/L initial concentrations or 46-311 mg dyes per g of membranes. MB adsorption fit the pseudo-second-order kinetics model and Freundlich adsorption isotherm, supportive of chemisorption onto the chemically heterogeneous SP fiber surfaces. The absorbed MB could be desorbed to recover >90% of the dyes and to regenerate the wet-resilient fibrous membranes in five adsorption-desorption cycles. This demonstrated ability to selectively separate and recover cationic and anionic dyes can be expanded in the separation and recovery of other cationic and anionic compounds relevant to environmental, biological or industrial applications.

Example 5: Soy Protein Film

Pristine amphiphilic and amphoteric soy protein (SP) microfibrils, selectively disassembled from the laminated and fibrous self-assembled products, were assembled into pH-responsive and β-rich films with distinct surface characteristics by simply manipulating the drying temperature and environmental moisture. When casting on hydrophobic substrates, hydrophobic moieties of SP microfibrils preferentially accommodated themselves towards it to achieve a more hydrophobic bottom surface (54.3°-70.8°), whereas films with very hydrophilic (ca. 5°-10°) bottom surface were obtained on hydrophilic substrates. Translucent films derived through optimal drying conditions (65° C., vacuum, moisture) contained 64% β structures, particularly 48% β-sheets, significantly contributing to the superior insolubility in harsh aqueous media at pH 0-10 for at least two weeks. Semi-crystalline films were highly sensitive to moisture with a moisture regain of 53.4% when conditioned at 85-90% relative humidity, leading to the decrease of the glass transition temperature from 193.1 to −11.8° C. The pH-responsive swelling behavior was validated with the minimal planar swelling ratio (S$_p$, 1.17) at pH 3 that close to the isoelectric point (PI, 4.51) of SPs and a much larger one (S$_p$=2.24 or 1.87) at pH 1 or 10. When cationic methylene blue (MB)-bound SP microfibrils were cast into films, a three-stage steady release of MB was observed in PBS buffer (pH=7.4) in vitro, following a quasi-Fickian diffusion mechanism.

Materials. Soy protein isolate (SPI, 92% protein) was purchased from MP Biomedicals, LLC. Hydrochloric acid (HCl, 1 N, Certified), sodium hydroxide (NaOH, 1 N, Certified), Ethanol (EtOH, anhydrous, histological grade), sodium chloride (NaCl, Certified), potassium chloride (KCl), acetic acid (CH₃COOH, Certified), sodium acetate (CH₃COONa, Certified) and methylene blue (MB) were all from Fisher Scientific. Sodium phosphate dibasic (99.95% trace metals basis) and potassium dihydrogen phosphate were purchased from Sigma-Aldrich. Regenerated cellulose dialysis membranes (3.5 kDa molecular weight cut-off, Fisherbrand, Pittsburgh, PA) were used for dialysis. All water used was purified by Milli-Q plus water purification system (Millipore Corporate, Billerica, MA). All chemicals were used as received without further purification.

Freeze-dried SP and SP/MB. Crude SPI was dispersed in water by a glass rod at 2 w % and dialyzed at 8-11° C. for 24 h. The dialyzed dispersions were then diluted to 1 w % and blended at 30 k rpm for 15 min using a high-speed blender (Vitamix 5200), cooled to ambient temperature, then centrifuged (5 k rpm, 15 min) to collect the supernatants, which were designated as colloids and stored at 8-11° C. Aq. SP colloids at 1 w % or their mixtures with MB (SP:MB=40:1, w/w, 1.025 w %) were frozen in 50 mL polypropylene centrifuge tubes (diameter: 1.1 inch) by immersing them in liquid nitrogen (−196° C., 5 min), then lyophilizing at −50° C. for 2 days in a freeze-drier (FreeZone 1.0 L Benchtop Freeze Dry System, Labconco, USA). The frozen and freeze-dried solids were referred as "freeze-dried or FD" for short from here on unless specified otherwise.

Preparation of films/membranes. FD SPs were dispersed in ethanol (EtOH, 10 mL) at 1 w/v % by sonication (130 W, 5 min), which can form soy protein microfibrils (SPMF). The solution was then put in the polystyrene (PS) hexagonal weighing boat, Teflon dish or Pyrex glass petri dish and respectively dried at 21° C. (#1-3) and 65° C. (#4-5). Vacuum was applied on #2, 3 and 5 to accelerate the drying process. For #3 and 5, a beaker of water was also put into the vacuum chamber to provide a moisty environment and a digital humidity meter (Traceable Humidity Meter, Fisher Scientific, Hampton, NH, USA) was used to measure the relative humidity (RH). Time was recorded when films were dry enough to automatically detach from the substrate. FD SP/MB were also dispersed in the same way and cast into films following the same conditions as #5. All films were stored under ambient conditions (21° C., 30-35% RH) if not specified. Their thickness was read to the nearest 0.01 mm by a vernier scale and their weight was measured using an analytical balance (Shimadzu, AUW220D) with an accuracy of 0.01 mg.

Characterization. Both sides of films/membranes were mounted with the conductive carbon tape and sputter coated with gold and observed using a field emission scanning electron microscope (FE-SEM) (XL 30-SFEG, FEI/Philips, USA) at a working distance of 5 mm and accelerating voltage of 5 kV. They were also stabilized on glass slides and scanned with the atomic force microscopy (AFM, MFP-3D, Oxford Instruments Asylum Research, Inc., Santa Barbara, CA) in the tapping mode with OMCL-AC160TS standard silicon probes (tip radius<10 nm, spring constant=28.98 N/m, resonant frequency of ca. 310 kHz) (Olympus Corp.) at 1 Hz scan rate under the ambient condition. The root mean square (RMS) roughness was calculated based on scanning over a 5 μm×5 μm area (N=5) on AFM images with 512×512 pixel resolution. Water contact angle (N=5) of both surfaces of films was measured on different batches of samples using the drop shape analysis method to report the average and standard deviation.

X-ray diffraction (XRD) patterns were collected to study the crystalline structures of FD SP and films/membranes on a Scintag XDS 2000 powder diffractometer using a Ni-filtered Cu Kα radiation (=1.5406 Å) at an anode voltage of 45 kV and a current of 40 mA. Diffractograms were recorded from 5° to 40° at a scan rate of 2°/min. Peak deconvolution analysis was conducted using Peak Fit (Systat Software) and individual peaks were fitted by Gaussian functions with $R^2>0.99$ for all deconvolutions. The ratio of total crystalline peaks area and the sum of both crystalline and amorphous area was taken as the crystallinity index (CrI). The unit cell dimension was calculated based on Bragg's law, $$d_{hkl} = \frac{\lambda}{2\sin\theta}$$

The secondary structure composition of FD SP and films/membrane was evaluated by Fourier transform infrared attenuated total reflection (FTIR-ATR) on a Nicolet iN10 microscope spectrometer (Thermo Fisher Scientific, USA) using a liquid nitrogen cooled detector. Each spectrum was collected from 1700 to 1600 cm⁻¹ at a 4 cm⁻¹ resolution to characterize the amide I band. The secondary structure composition was analyzed in the same way as reported above. Thermal behavior of FD SP and films was evaluated using a differential scanning calorimeter (DSC-60, Shimadzu) and thermo gravimetric analyzer (TGA-50, Shimadzu) with Shimadzu thermal analysis system (TA-SOWSI). It was performed by heating at 10° C./min under flowing N₂ at a 50 mL/min rate to 400° C. Derivative thermogravimetric (DTG) curve was the first derivative derived from the TGA data.

Films, originally conditioned and stored at 21° C. and 30-35% RH, were respectively reconditioned at 21° C. with 65% RH or 85-90% RH for 24 h and weighed using an analytical balance (Shimadzu, AUW220D) with an accuracy of 0.01 mg. The moisture regain of each film was calculated and plotted by defining the one at 150° C. (0% RH, read from TGA data) as 0.0%. Film #3 and 5 or the SP/MB film were cut into 3 cm×1 cm (ca. 30 mg) strips and immersed in water, aq. HCl (pH=0, 1 or 3) or NaOH (pH=10 or 12) solutions at 21° C. or in phosphate-buffered saline (PBS, pH=7.4), CH₃COOH/CH₃COONa (pH=4.5) or HCl/KCl (pH=1.5) buffer at 37° C. for different lengths of time. Each sample was removed from the aq. media at the prescribed time and the surface liquid was gently wiped off with Kimwipes. The width, length and thickness were measured by a vernier scale to the nearest 0.01 mm and the mass was weighed using the analytical balance. The planar (length×width), thickness and mass swelling ratios were calculated as the ratios of the corresponding measured values of swollen films to that of original dry samples, and denoted as $S_p$, $S_t$ and $S_m$, respectively. Three measurements were conducted to report the mean with standard deviations.

FD SP/MB dispersions (0.1 w/v %, 10 μL) in EtOH were put on a glass slide and observed under a Leica DM2500 optical microscope equipped with the cross-polarizing filter. SP/MB films (ca. 20 mg) were respectively immersed in 25 mL phosphate-buffered saline (PBS, pH=7.4), CH₃COOH/CH₃COONa (pH=4.5) and HCl/KCl (pH=1.5) buffer and their in vitro release of MB was performed in a shaker bath at 37° C. At predetermined time intervals, 1 mL solution was taken to quantify the amount of MB using Evolution 600 UV-vis spectrophotometer (Thermo Scientific) based on the calibration curve determined in the same aq. media. Then, 1 mL fresh buffer was added to the tubes to keep the volume consistently. The mechanisms of release from SP/MB films were investigated using a semi-empirical model known as the power law or the Korsmeyer-Peppas model that is usually used to describe the drug release from a polymeric system, $$\frac{M_t}{M_\infty} = kt^n$$

where $M_t$ and $M_\infty$ represent the amount of drug released at a time t at equilibrium, k is a constant characteristic of the release system, and n is the diffusion exponent characteristic of the release mechanism.

Figure 13:
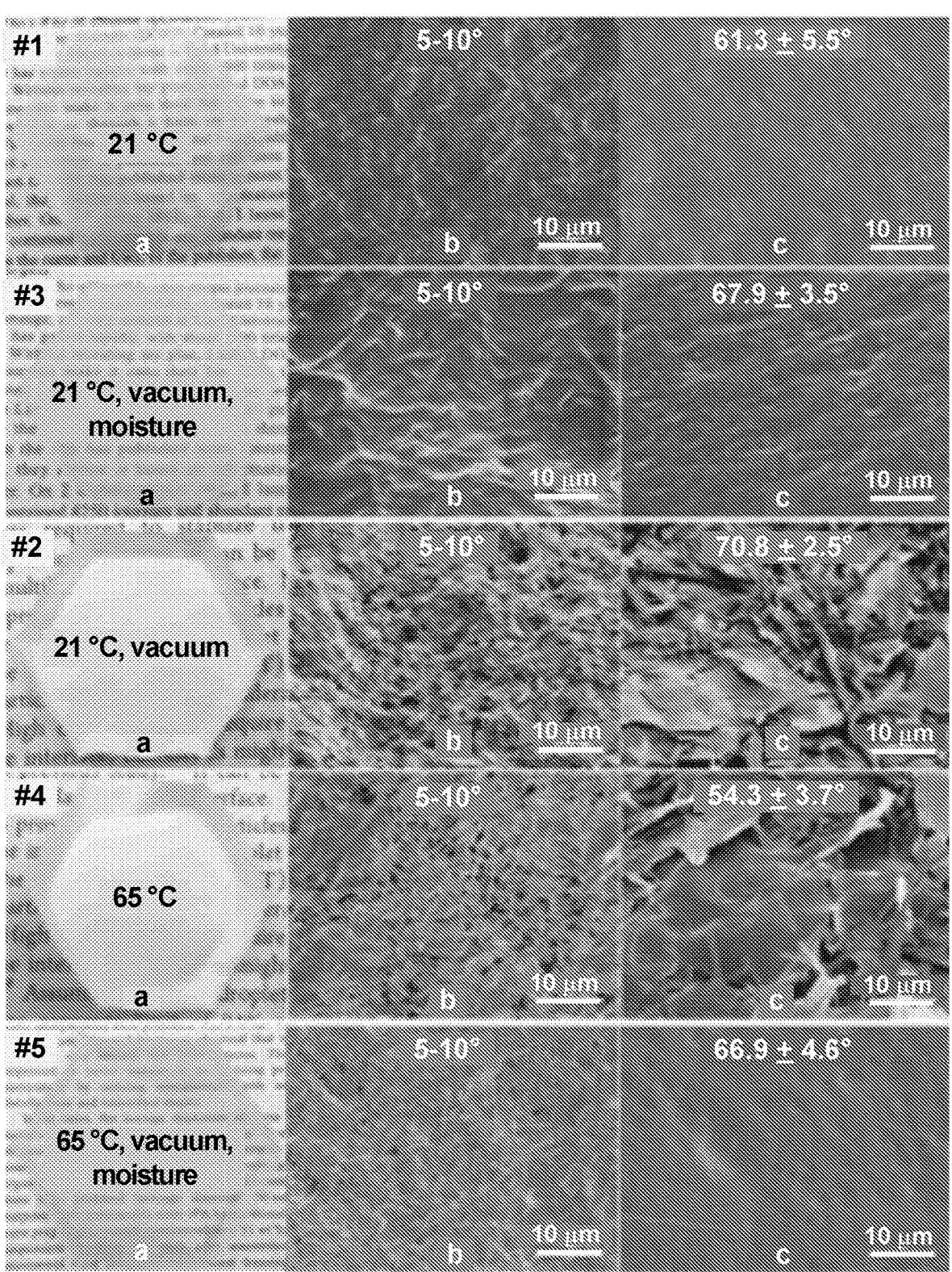
FIG. 13 shows photographs (left column) and SEM images of the top (middle column) and bottom (right column) surfaces of films/membranes dried in PS weight boats with the water contact angle (N=5) denoted: #1 (21° C.); #2 (21° C., vacuum); #3 (21° C., vacuum, moisture); #4 (65° C.); #5 (65° C., vacuum, moisture).

Surface characteristics of films/membranes as affected by drying conditions. EtOH dispersions of SP microfibrils in the average width of 1.29 μm and length of 52.8 μm, were dried in hydrophobic PS weight boats at 21 or 65° C. with different amount of environmental moisture to investigate how drying conditions influenced the structural characteristics of assembled films/membranes. Both #1 and 2 were derived at 21° C. with the same relative humidity (RH) of 30-35%, however, #2 was fully dried within 16 h instead of 72 h (#1) owing to the accelerated evaporation of EtOH driven by the vacuum (Table 4). Consequently, pale-yellow and translucent film #1 dried through a substantially slower process (ca. 72 h) had a thickness of merely 0.09 mm and two smoother and more fused surfaces, although a few cracks were visible on the top surface (FIG. 13, Table 4). Whereas the opaquely white membrane #2 with the thickness of 0.17 mm was generated with visibly rough surfaces, appearing as abundantly unfused microfibrils and pieces of sheet-like structures under SEM (FIG. 13, Table 4). A high RH of 75-82% was identified in the vacuum chamber with a beaker of water at 21° C. after reaching the equilibrium, which slowed down the evaporation and led to the formation of the translucent film #3 after ca. 48 h (FIG. 13, Table 4). Two surfaces of film #3 fused into one whole piece with embedded microfibrils on the top surface and some concave structures observed on the bottom one (FIG. 13, Table 4). Both #4 and 5 were generated at a higher 65° C. within 2 h but obtained distinctly opaqueness and thickness (0.17 mm vs 0.06 mm, Table 4). While #4 exhibited similar appearance to opaque membrane #2, the top surface of translucent film #5 maintained microstructural motifs and the bottom one completely fused into one piece with a few surface depressions (FIG. 13, Table 4), probably attributed to the different amount of environmental moisture (RH: <8% vs 55-60%, Table 4). Overall, the fusion degree of microfibrils was consistent with the thickness and opaqueness of films/membranes, higher degree of fusion leading to thinner and more translucent films. Slower drying process (#1 vs 2) and/or the more humid environment (#2 vs 3, #4 vs 5) seemed to promote the association and fusion of SP microfibrils by establishing more intermolecular forces and/or hydrating SP microfibrils.

TABLE 4

SP films/membranes cast from microfibril EtOH dispersions (1 w/v %, 10 mL): drying conditions, relative humidity (RH), drying time, appearance and thickness.

| Sample# (drying conditions) | RH (%) | Drying time (h) | Appearance | Thickness (mm, N = 3) |
|---|---|---|---|---|
| #1 (21° C.) | 30-35 | 72 | Pale yellow, translucent | 0.09 (±0.01) |
| #2 (21° C., vacuum) | 30-35 | 16 | White to slightly pale yellow, opaque | 0.17 (±0.02) |
| #3 (21° C., vacuum, moisture) | 75-82 | 48 | Pale yellow, translucent | 0.06 (±0.02) |
| #4 (65° C.) | <8 | 2 | White to slightly pale yellow, opaque | 0.17 (±0.03) |
| #5 (65° C., vacuum, moisture) | 55-60 | 2 | Pale yellow, translucent | 0.06 (±0.02) |

Unlike the very hydrophilic (5-10° and visually rougher top surface that exposed to air during the drying process, the average water contact angle (WCA) on the bottom surface dried on the hydrophobic PS were determined as 54.3-70.9° on average (FIG. 13), remarkably more hydrophobic. When water drops were added on both surfaces of films (i.e. #2 and 4) in a vertical position, they immediately wetted their top surfaces but retained the meniscus on the bottom surfaces for ca. 2 min. Adding a drop of water to the more hydrophobic bottom surface also caused the film #1, 3 and 5 to deform or arch and tend to roll off it. The average root mean squared (RMS) roughness of film #3 and 5 as determined by AFM further confirmed that the more hydrophobic (66.9° and 67.9°) bottom surfaces were overall smoother than that of the hydrophilic (5°-10°) top ones (44.0 vs 138.8 nm; 37.6 vs 164.0 nm), suggesting that the roughness or surface topography should not be the only reason for the improved hydrophobicity of the bottom surfaces.

SP microfibrils were also respectively dried on a hydrophilic glass petri dish and a hydrophobic Teflon plate to further investigate the impact of the hydrophilicity/hydrophobicity of substrates. Under the same drying conditions with #2 and 4, both bottom surfaces on glass were very hydrophilic (5-10° and top ones had an average WCA of 47.3±4.1° and 26.3±4.4° (N=5), respectively. When drying under the condition #1, the bottom surface of the film strongly adhered to the glass surface and the film was unable to be completely peeled, implying the strong affinity of SP microfibrils to glass probably due to the building of intense intermolecular interactions (i.e. H-bondings) during the slow drying process. On the Teflon plate, similar water contact angles on the top (ca. 5-10°) and bottom surfaces (ca. 50-60°) of films were also determined as the ones dried on the PS under the same conditions. The hydrophobic and hydrophilic moieties of amphiphilic SP microfibrils seemed to respond to the hydrophilicity or hydrophobicity of the substrates and organize themselves in a way to encourage the hydrophilic-hydrophilic or hydrophobic-hydrophobic interactions.

The contact angle of a rough surface is defined by cos θ*=r cos θ, where θ* is the apparent contact angle at equilibrium state; r is the roughness ratio, which is the ratio of the true area to the apparent area of the surface (>1 for a rough surface); θ is the Young's contact angle for the ideal surface of the same material. Earlier studies indicate that the surface of hydrophilic material generally becomes more hydrophilic and the hydrophobic one gets more hydrophobic with the increasing of the surface roughness. In the case of SP films/membranes, it seems that amphiphilic microfibrils tend to adapt to the hydrophobic substrate by encouraging the hydrophobic moieties towards it, which is probably the major reason for the increased water contact angles. The roughness of the bottom surface may aid but should not be the only contributor. Prior works also reported SP cast films with two hydrophobic surfaces by arylation with benzilic acid (53.6°-65.0°), mixing with 0.7-1.9% of the polydopamine-modified cellulose (64.2°-74.8°), or growing copper phosphate nanoflowers on surfaces (ca. 130°-150°). Both the hydrophobicity of functional groups or components and the roughness were attributed to the increased surface hydrophobicity. It is noteworthy that neither extra chemical modification, particularly harsh and toxic ones, nor extra components has been involved in this work.

Crystallinity, secondary structure composition and thermal behavior. X-ray diffraction diagrams of both FD SPs and films were collected and analyzed by applying the peak fitting method to study the crystalline domains of SPs. Two major types of characteristic peaks at $2\theta=14.1$-$21.6°$ and $22.3$-$28.1°$ with corresponding d-spacings of 4.1-6.3 Å and 3.2-4.0 Å were resolved (FIG. 14A), respectively assigned to the inner strand distance within $\alpha$-helical and $\beta$-structures. The minor one at 7.7-9.0° corresponding to the equatorial reflection of 9.8-11.5 Å is considered to be correlated to the inter-sheet or -helix spacing. The crystalline index (CrI) of films were determined as 50-56%, overall 9-15% larger than that of FD SPs (41%, FIG. 14A). Amide I region was also characterized by FTIR-ATR, showing a very similar peak morphology that suggests similar secondary structure compositions, except for a remarkable peak shift towards lower wavenumbers that correlated to $\beta$-sheets observed on film #5 (FIG. 14B). SPs in all five films contained a high content (80-92%) of ordered secondary structures, maintaining the semi-crystalline nature of the raw material (FD SPs: 80%) and particularly containing 12-21% more $\beta$ domains (FIG. 14C).

Figure 14A:
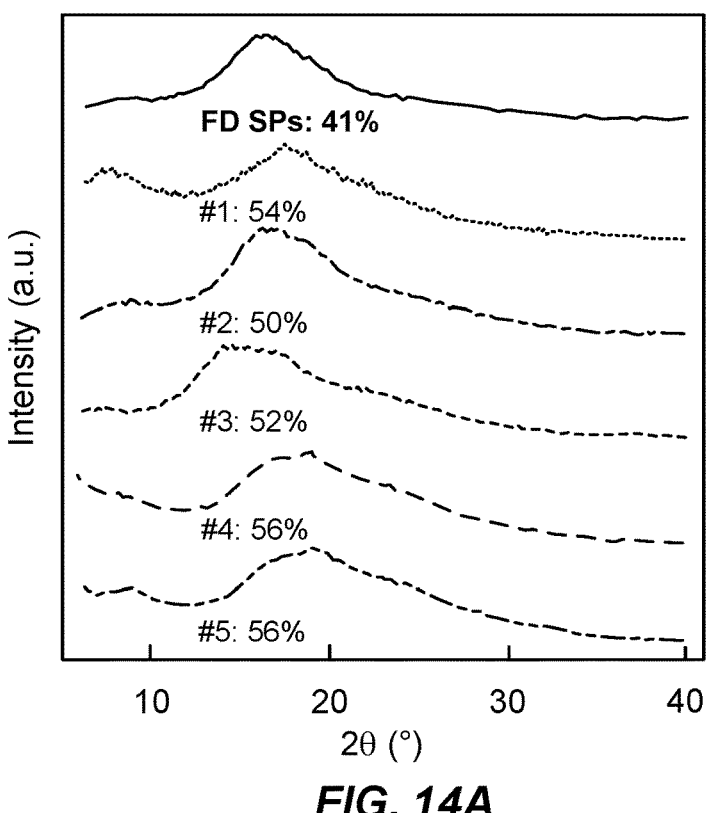
Figure 14B:
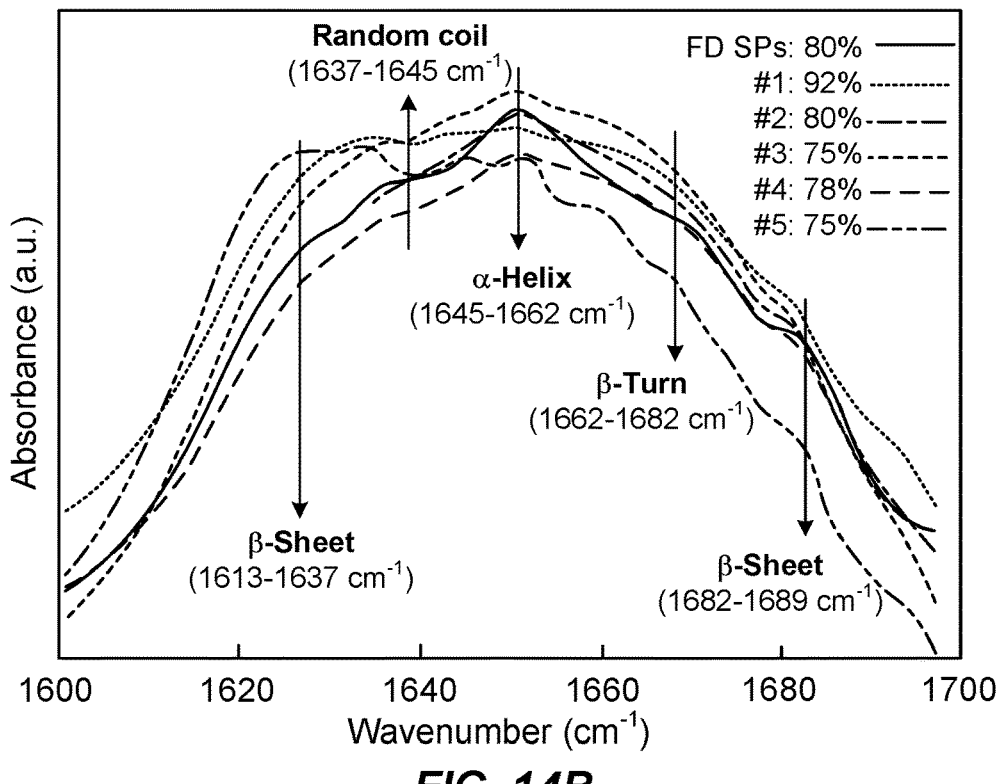

Film #1 derived via the slowest drying process (21° C., 72 h) owned the highest content of ordered secondary structures (92%) and a high CrI of 54% as determined by FTIR-ATR and XRD (FIGS. 14A-14C). Opaque membrane #2 that quickly dried within 16 h at 21° C. in vacuum possessed the lowest amount (80%) of ordered secondary structures and the lowest CrI (50%). When a high RH of 75-82% was induced in vacuum at 21° C., film #3 obtained a very similar secondary structure composition to those in #1 (72 h), including 28% (vs 26%) $\alpha$-helix, 34% (vs 33%) $\beta$-sheet and 23% (vs 25%) $\beta$-turn, and a similar CrI was also identified as 52% (vs 54%, FIGS. 14A-14B). Quick drying (2 h) at a higher 65° C. (#4) also achieved a CrI of 56% and 88% ordered secondary structures, quite similar to those of film #1 (54% and 92%), however, as high as 40% $\beta$-sheets were obtained (FIGS. 14A-14C). In the moister environment with the RH of 55-60% (#5), drying at 65° C. not only achieved the highest CrI of 56% but also further induced the formation of more $\beta$-sheets (48% vs 40%) as compared to #4. Analyses on X-ray diffraction diagrams also confirmed that more $\beta$ domains were generated in #4 (23%) and 5 (23%) at 65° C. as compared to #1-3 (5-12%). Slower drying speed, more moisture and higher drying temperature were found to be correlated to the formation of more ordered secondary structures, particularly $\beta$-sheets.

To date, many methods have been reported to successfully induce the secondary structural transition of proteins (mainly silk fibroin) towards more $\beta$-sheets, such as the most common approach by using organic solvents (i.e. methanol and EtOH, ca. 36-56% $\beta$-sheet) for the short—(i.e. 10 min) or long-term (i.e. 2-4 d) immersion or as the co-solvent (i.e. formic acid, ca. 40% $\beta$-sheet) to interrupt original H-bondings and encourage the exposure of hydrophobic side groups, water vapor annealing at 4-10° C. for 12 h (ca. 14-60% $\beta$-sheet or at 121° C. through the steam-autoclaving (ca. 60% $\beta$-sheet), and slowing down the evaporation rate of water (ca. 23% $\beta$-sheet) to influence the formation of H-bondings or the crystallization. In this work, some of these approaches, such as applying less polar organic solvent (EtOH), water vapor annealing, higher temperature (65° C.) and slow drying, were also systematically demonstrated to be effective on SPs for the first time. Especially, the combination of water vapor and a higher temperature at 65° C. were thought to efficiently contribute to the formation of 48% $\beta$-sheets of SPs in film #5 within merely 2 h. Drying at a higher 65° C. may provide more and sufficient thermal energy for the large-scale molecular motion of polypeptide chains to induce the crystallization and lead to an increase in the kinetics of crystallization.

Thermal behaviors of SPs were also studied, and all samples were found to be hygroscopic with all films losing 8.0-11.5% moisture more gradually by ca. 150° C. as compared to FD SPs that quickly losing all 7.0% before ca. 80° C. (FIGS. 14D-14E). The slower moisture loss of films suggested more bound water. All SPs started to decompose approximately at above 210° C. and lost a significant mass of 42-50.3% by 400° C. (FIG. 14D). Film #1-3 derived in a substantially slower evaporation process (16-72 h) not only lost 6.6-8.3% less weight but also exhibited 4.5-6.2° C. higher peak degradation temperature ($T_{max}$) than those of FD SPs. Whereas #4-5 that dried within the shortest time (2 h) lost similar amount of mass (49.5 and 50.3%) to FD SPs (FIG. 14C). Although the $T_{max}$ of #4 was even 5.4° C. lower than FD SP, film #5 had a 16.9-28.5° C. higher $T_{max}$ than all other films, which may be related to its as high as 64% $\beta$ domains.

Figure 15A:
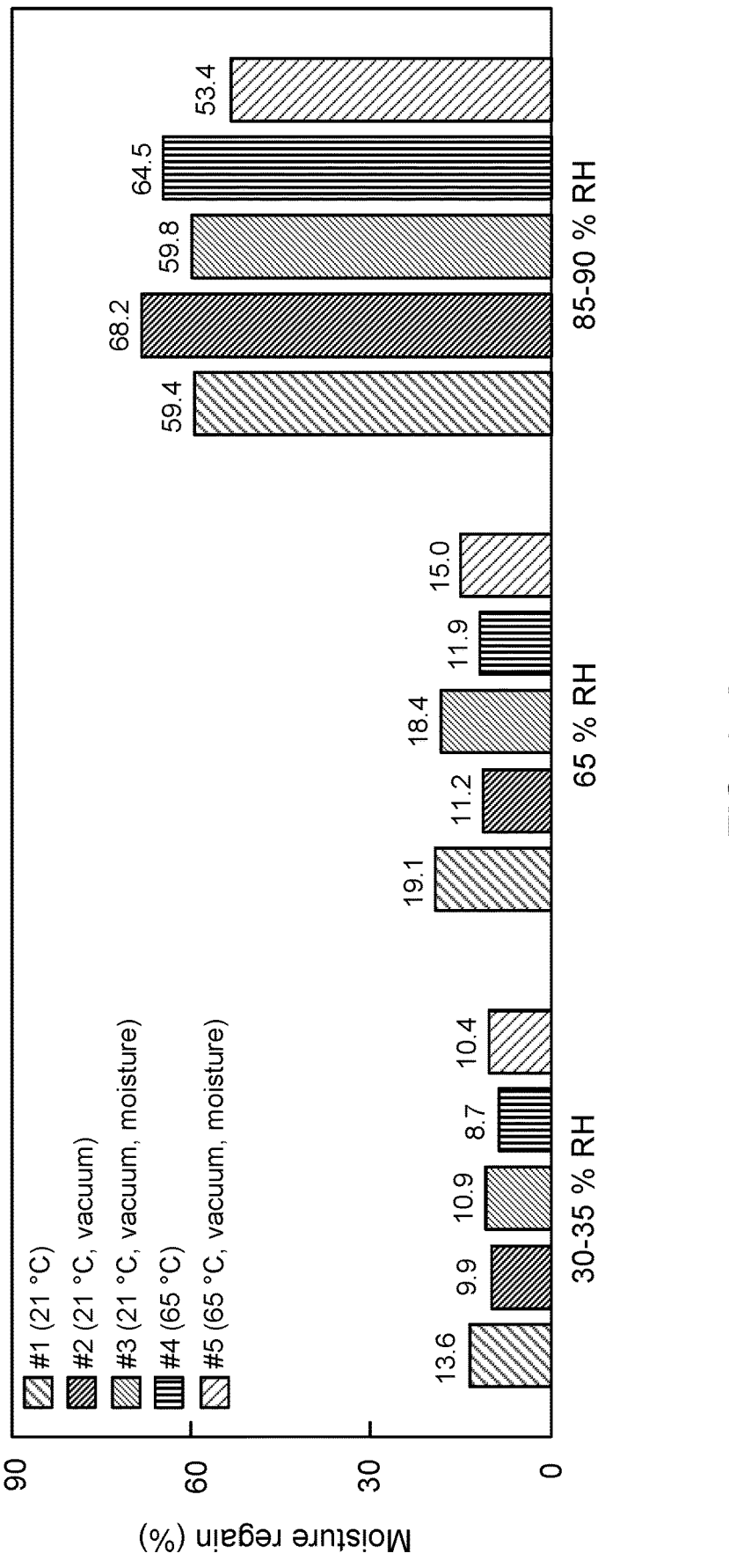
FIG. 15A shows moisture regain of SP film/membrane #1 (21° C.), #2 (21° C., vacuum), #3 (21° C., vacuum, moisture), #4 (65° C.) and 5 (65° C., vacuum, moisture) respectively conditioned at 30-35, 65 and 85-90% RH.

Moisture regain and pH-responsive swelling behavior in aq. media. Bending 180° led to the breakage of all five films/membranes after being conditioned under the RH of 65% at 21° C. However, they were highly moisture-sensitive and became foldable in a highly humid environment with the RH of >80%. Films/membranes stored at 21° C. with 30-35% RH were then investigated regarding the moisture regain by reconditioning them under different RH for 24 h, which turned out to be sufficient to saturate them with the moisture based on their mass gain. By defining their moisture content at 150° C. as 0.0%, moisture regains of translucent film #1, 3 and 5 were found to be similar and slightly higher (0.5-4.9% or 3.1-7.9%) than those of #2 and 4 at 30-35% or 65% RH (FIG. 15A). Whereas opaque membrane #2 and 4, with the least degree of fusion of SP microfibrils, absorbed as high as 68.2 and 64.5% moisture at 85-90% RH (FIG. 15A). Films gained similar or slightly higher moisture regain as compared to wool (14.0-19.0%) and silk (11.0%) textiles at 65% RH, however, they obtained approximately at least twice amount of moisture regain than any known hygroscopic textiles, the one of which is generally far below 30% when conditioned at 100% RH.

Figure 15B:
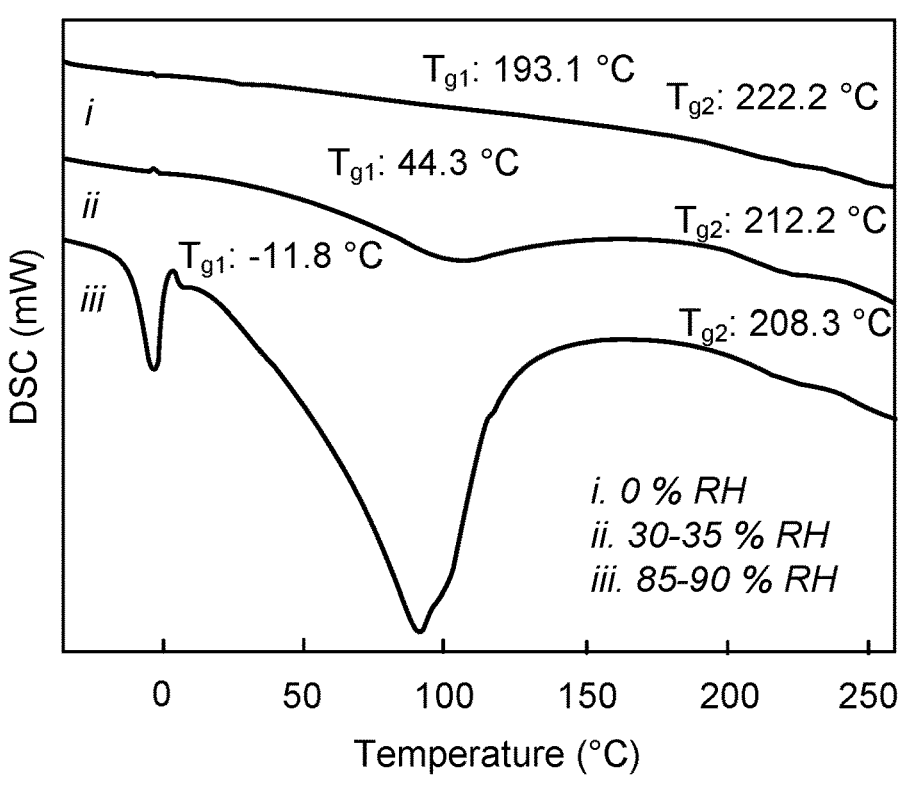
FIG. 15B shows DSC of film #5, completely dried (0% RH) or conditioned at 30-35 and 85-90% RH.

DSC was then conducted to determine the glass transition temperature ($T_g$) of SPs in film #5 to explore the potential reasons for the improved flexibility in a highly moist environment. Double glass transitions were observed (FIG. 15B), which was consistent with prior reports and thought to correspond to two major SP components ($\beta$-conglycinin and glycinin). When the film #5 was conditioned at 30-35 and 85-90% RH, the first glass transition temperature ($T_{g1}$) dramatically decreased from 193.1° C. (completely dried at 150° C.) to 44.3 and −11.8° C., and the second one slightly dropped from 222.2° C. to 212.2° C. and 208.3° C., respectively (FIG. 15B). The significantly lower $T_{g1}$ (−11.8° C.) below the room temperature may explain the foldable and rollable film #5 in a highly humid environment. $T_g$ of proteins is well known to be moisture sensitive and on average drops ca. 10° C. for every 1% increased moisture content. For instance, when conditioning silk cast films at 13 or 75% RH, the merely 2 and 25% moisture respectively reduced the $T_g$ from 178-180° C. for completely dry silk to ca. 140 and 25° C. As proposed by McGrath et al., water molecules, particularly the bound water, may act as the plasticizer to disrupt intermolecular cohesive forces among the peptide chains of SPs and reduce the steric hindrance for the chain movement and reorientation in the non-crystalline region, thus leading to the dramatic reduction of $T_g$ in film #5. Contrary to generally accepted ideas, a relatively fast heating rate of 10° C./min has been applied in this study and this is known to lead to a relatively higher $T_g$ determined due to the thermal lag. However, such fast heating rate could actually help mitigate the evaporation of bound water to study its effect on the glass transition.

Membrane #2 and 4 were spontaneously disintegrated when submerged in water, and film #1 was visibly stable in water for at least 24 h but easily broken upon being picked up by the tweezer. Therefore, only film #3 and 5 were further studied with regard to their swelling behavior in aq. media. They both swelled but were strong enough to be picked up by the tweezer after being respectively immersed in aq. media at pH 0, 1, 3, 7 and 10 for two weeks, overall only losing less than 5% mass. When the pH was further increased to 12, both films immediately swelled and completely disintegrated within 10 min. Even when the thickness of both films was doubled, they could only remain integral for a few more minutes only.

Figure 15C:
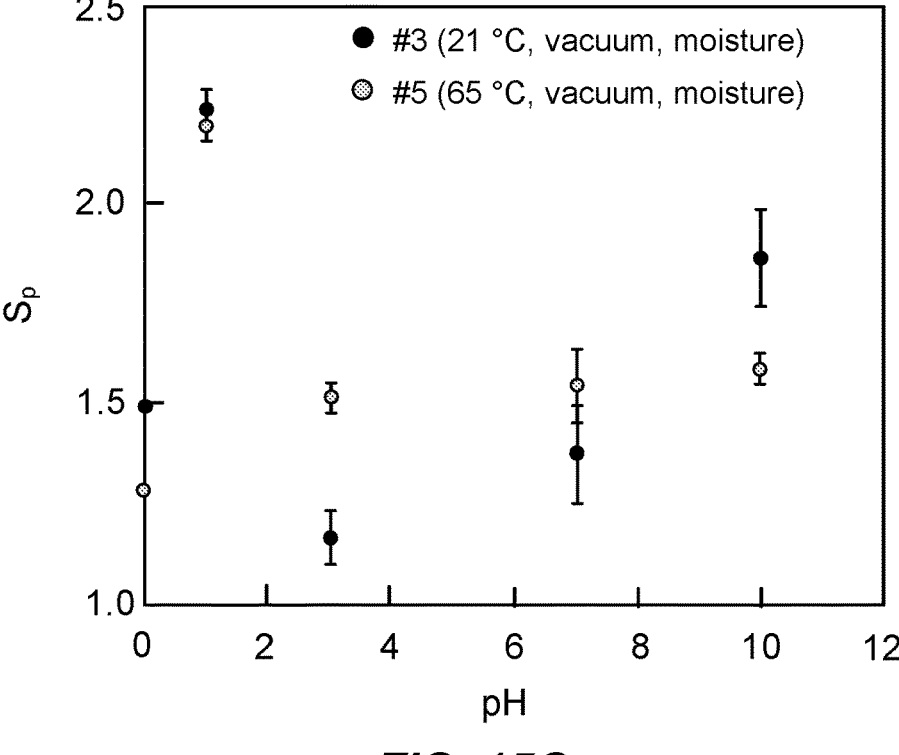
FIG. 15C shows planar swelling ratio ($S_p$, N=3) of film #3 and 5 in aq. HCl or NaOH at different pH (0-10).

Film #3 and 5 both swelled instantaneously and reached to the swelling equilibrium based on the planar swelling ratio ($S_p$) within 5 min in aq. HCl or NaOH expect that film #3 would further swell to have a $S_p$ of 4.13 and a higher 4.63 at pH 10 after one- and two-week immersion, respectively (FIG. 15C). They both swelled the least at pH 3 (1.17 or 1.52) that close to the isoelectric point (PI, 4.51) of SPs and the most at the pH far from it (pH=1, 2.24 or 2.24; pH=10, 1.87 or 1.59) expect at pH 0 (1.50 or 1.29) (FIG. 15C). Moreover, when film #3 and 5 were air-dried after the two-week immersion in water, films shrank to their original sizes and would swell to a similar dimension again in water and remained resilient after being submerged in water for at least another two weeks. Although the surface liquid was very gently wiped off for the mass swelling ratio measurement, it was still hard to control the experimental error using current methods. The thickness swelling was not discerned because the change on the thickness was so minor that it was not measurable since the Vernier scale was only read to the nearest 0.01 mm.

The pH-responsive swelling behavior of film #3 and 5 reflected the amphoteric nature of SPs that would be deprotonated into —COO⁻ below the PI or protonated into —NH₃⁺ above the PI to generate repulsive forces. Since SPs in film #1 owned the largest content of ordered secondary structures (92.1%), the instability of the film in aq. media was probably correlated to the relatively lower degree of fusion of microfibrils and especially those cracks observed in its less dense structure (FIG. 13). The outstanding pH-resistant property of film #3 and 5 under extremely acidic (pH=0) and basic (pH=10) condition was thus attributed to not only the high content of ordered secondary structures (84.5 and 85.9%) and crystalline domains (52.3 and 56.2%)

but also the higher degree of fusion of microfibrils in their dense structures that promoted by water vapor and/or high temperature.

When the solvent (EtOH) was progressively eliminated through the evaporation during the air-drying process, SP microfibrils were extensively concentrated and densely packed. Non-covalent intermolecular interactions, especially H-bondings, electrostatic and hydrophobic interactions, would be established among microfibrils. Consequently, the cohesion of the final network would determine the structural and functional properties of the films obtained. Slow drying at ambient temperature (72 h, #1) probably allowed to establish more sufficient intermolecular interactions, therefore, led to a relatively dense structure with the highest amount of ordered secondary structures (92%, by FTIR-ATR) and the CrI of 54% by XRD. Both high temperature (65° C.) and water vapor annealing were also found to play a major role in inducing more ordered secondary structures probably by influencing the rearrangement of the H-bondings. When both factors were combined in #5, as high as 64% β structures and the highest CrI of 56% were achieved within merely 2 h. Amphiphilic SP microfibrils also seem to respond to the hydrophilicity or hydrophobicity of the substrates, leaving the bottom surface with the water contact angle of ca. 5-10° or up to 70.8° by simply drying them on a hydrophilic or hydrophobic substrate. Pristine SP film #5 (65° C., vacuum, moisture) was sensitive to moisture and owned a moisture regain of 53.4% when conditioned at 85-90% RH, leading to the decrease of the glass transition temperature of SPs from 193.1° C. (completely dry) to −11.8° C. It was also intrinsically insoluble in extremely acidic (pH=0) and basic (pH=10) aq. media probably due to its densely packed and fused structures and semi-crystallinity, particularly the 48% β-sheets. It was also amphoteric and showed a pH-responsive swelling behavior in a broad range of pH, swelling to the least extent ($S_p$=1.17) at pH near the PI (pH=3) and to the largest ($S_p$=2.24 or 1.87) at pH far from the PI (i.e. pH=1 or 10).

Example 6: Controlled Release of a Drug Using Soy Protein Film

Figure 16A:
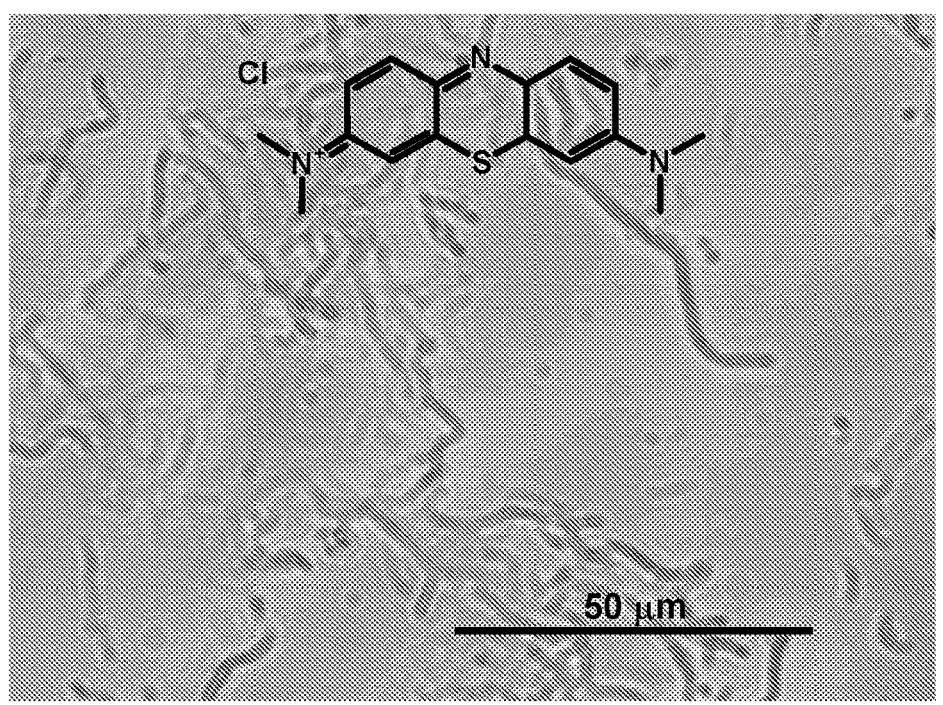
FIG. 16A shows SP microfibrils with methylene blue (MB) encapsulated air-dried and imaged by the transmission microscopy (chemical structure of MB and image under the crossed polar inserted); SP/MB films (65° C., vacuum, moisture) in PBS (pH=7.4), $CH_3COOH/CH_3COONa$ (pH=4.5) and HCl/KCl (pH=1.5) buffer in vitro.
Figure 16B:
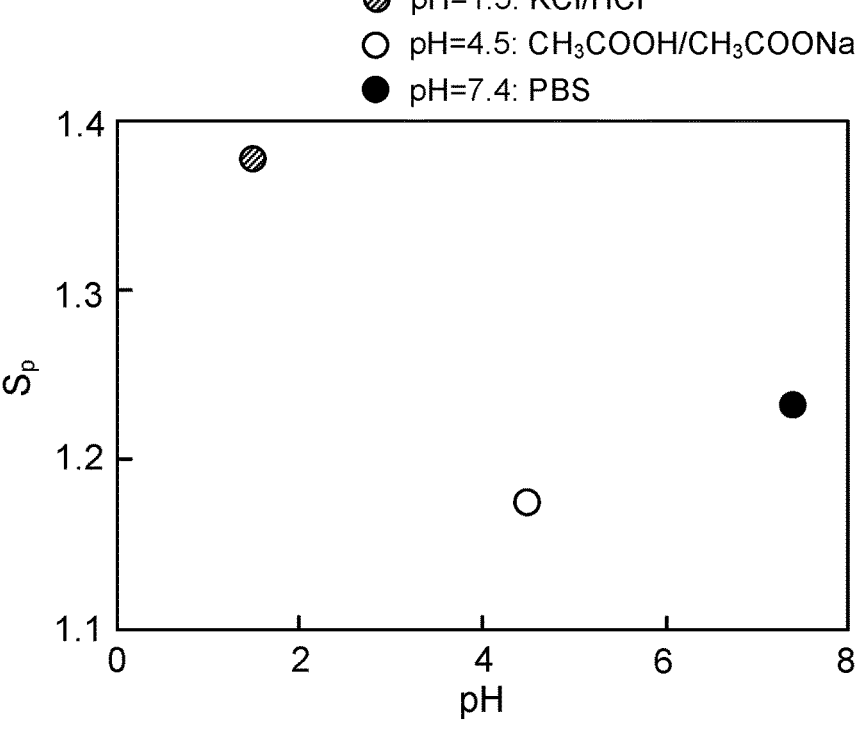
FIG. 16B shows planar swelling ratio ($S_p$).
Figure 16C:
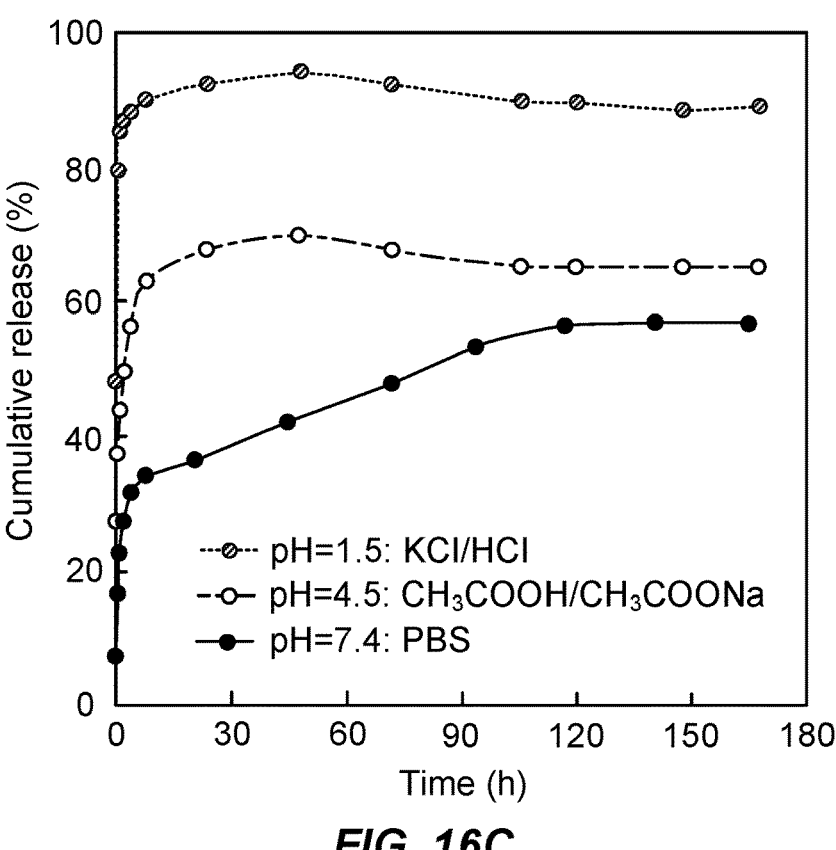
FIG. 16C shows cumulative release of MB.
Figure 16D:
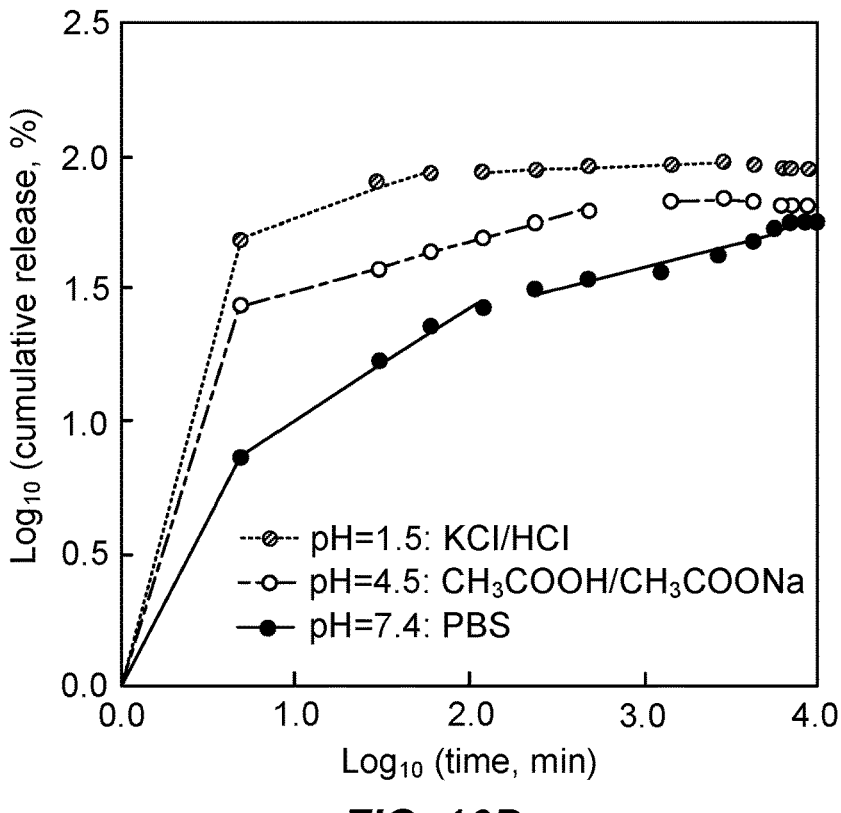
FIG. 16D shows Korsmeyer-Peppas model fitting of MB release.

Controlled release of methylene blue (MB) in vitro. Film #5 with the optimal performance was further investigated as potential carrier substrates for the controlled release of functional and cationic MB in vitro by directly encapsulating and bounding it to microfibrils (FIG. 16A). Directly adding 0.025 w % or 0.08 mM MB to 1 w % SP colloids could facilely generate SP/MB microfibrils with similar dimensions to pristine SP microfibrils without affecting the self-assembling behavior of SP colloidal particulates and the following selective disassembly. Ca. 94.1% MB was found to be encapsulated into microfibrils or adsorbed on their surfaces after dispersing FD SP/MB in EtOH as determined by UV-vis. SP/MB (40:1, w/w) microfibrils exhibited similar bluish birefringence under the crossed polar and were similarly wide (1.2-1.3 μm) and long (20-100 μm) as pristine SP microfibrils (FIG. 16A). Such microfibrils in EtOH were then directly cast into films under the optimal condition (65° C., vacuum, moisture). The pH-responsive swelling behavior and the release of MB from the SP/MB film in vitro were then respectively studied in PBS (pH=7.4), CH₃COOH/ CH₃COONa (pH=4.5) and HCl/KCl (pH=1.5) buffers at 37° C. (FIG. 16B-16D). The swelling of SP/MB films reached to the equilibrium within the first 5 min and would not significantly change afterwards (FIG. 16B). The least extent of swelling with the $S_p$ of 1.08-1.18 was identified in the $CH_3COOH/CH_3COONa$ buffer at pH 4.5 that was very close to the PI (4.51) of SPs. And they swelled to a larger extent of 1.16-1.23 in PBS buffer (pH=7.4) and 1.38-1.49 in HCl/KCl (pH=1.5) in vitro. The cumulative release of MB in three different buffers fitted the Korsmeyer-Peppas model well with the $R^2$ of 0.93-0.99 and parameters were calculated accordingly (Table 5). After the stage I release of 7.53% MB within 5 min in PBS buffer (pH=7.4), 17.8 and 31.9% were then released with the release exponent (n) of 0.42 and 0.17 in the following distinct stage II and III, taking 1.4 h and 167.7 h, respectively (FIG. 16C-16D, Table 5). At pH 7.4, in total 57.2% MB was released from SP/MB films within two weeks and films still remained the blue color till the end (FIG. 16C-16D, Table 5). In the $CH_3COOH/CH_3COONa$ buffer (pH=4.5), the burst release of 27.4% MB was identified within the initial 5 min and then another 40.6% was released within 11.6 h with then of 0.18 (FIG. 16C-16D, Table 5). A rapid release of as high as 48.8% MB occurred within the first 5 min in HCl/KCl buffer with the pH of 1.5, and then another 36.4% was quickly released in the following 1 h (FIG. 16C-16D, Table 5). Consequently, originally dark blue SP/MB films remarkably turned pale yellow within 1 h. The release exponent of MB in three buffers was all smaller than 0.5 except for the initial burst release stage, corresponding to the quasi-Fickian diffusion mechanism that commonly observed in a polydisperse release system, in which MB diffused through a swollen and positively/negatively charged matrix.

TABLE 5

Parameters of MB release in vitro fitted by
Korsmeyer-Peppas model

| pH of Buffer | Release stage | Time (h) | Cumulative release (%) | Release exponent, n | Correlation coefficient, $R^2$ |
|---|---|---|---|---|---|
| 7.4 | I | 0.08 | 7.53 | N.A. | N.A. |
| | II | 1.4 | 17.8 | 0.42 | 0.9922 |
| | III | 167.7 | 31.9 | 0.17 | 0.9320 |
| 4.5 | I | 0.08 | 27.4 | N.A. | N.A. |
| | II | 11.6 | 40.6 | 0.18 | 0.9986 |
| 1.5 | I | 0.08 | 48.8 | N.A. | N.A. |
| | II | 0.7 | 36.4 | 0.24 | 0.9765 |

The burst release of MB within the first 5 min in all three buffers seemed to be correlated to the ca. 6% of MB released from microfibrils during the dispersion process and those released from the fulfilled swelling of films. Through the deprotonation of carboxylic acid groups at pH 7.4, negative charges generated from the carboxylates of SPs are thought to stabilize the cationic MB through strong attractive electrostatic interactions, which may explain overall the least (57.2%) amount of release in the PBS buffer and particularly the substantially slower release of the encapsulated MB from microfibrils in the III stage (31.9%, 167.7 h, Table 5). Whereas primary amines were protonated at pH 1.5 to carry positive charges, which not only repel cationic MB molecules but also cause the largest swelling extent ($S_p$=1.38-1.49) of the film, thus leading to the release of the highest 85.2% MB within less than 1 h (Table 5). In the buffer with the pH of 4.5, films slightly swelled with the $S_P$ of 1.08-1.18 and may stabilize MB only by relatively weak H-bondings and hydrophobic interactions due to the almost zero net charge of SPs. Therefore, the total release of 68.0% MB within 11.7 h at pH 4.5 were in-between as compared to the ones at pH 1.5 and 7.4. In theory, the three-stage release behavior of cationic MB at pH 7.4 could be expected on a similarly water-soluble anionic drug from the films in HCl/KCl buffer (pH=1.5).

When incorporating functional agents into microfibrils and casting them into films under the optimal condition (65° C., vacuum, moisture), the very water-soluble cationic MB from the SP/MB film showed a three-stage (7.53%: 0.08 h; 17.8%: 1.4 h; 31.9%: 167.7 h) steady release in PBS buffer (pH=7.4) and followed a quasi-Fickian diffusion mechanism in vitro.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A gel fiber composition comprising:
   a soy protein colloid (SPC) or soy protein microfibril (SPMF);
   sodium alginate (SA); and
   a hydrocarbon solvent or soy oil.

2. The composition of claim 1, comprising SPMF and SA in a ratio of 1:1 to 4:1 (w/w).

3. The composition of claim 1, wherein the hydrocarbon solvent is cyclohexane or hexadecane.

4. The composition of claim 1, wherein the gel fiber composition comprises cyclohexane, hexadecane, or soy oil.

5. The composition of claim 1, wherein the gel fiber composition comprises:
   SPMF and SA in a ratio of 2:1 (w/w); and
   hexadecane in an amount of 75% (v/v).

6. The composition of claim 1, wherein the gel fiber has a diameter of 300 to 1000 μm.

7. A method for preparing the gel fiber of claim 1, the method comprising:
   (a) forming a reaction mixture comprising a soy protein colloid (SPC) or soy protein microfibril (SPMF), sodium alginate (SA), and a hydrocarbon solvent or soy oil; and
   (b) spinning the reaction mixture into a $CaCl_2$ aqueous solution, thereby forming the gel fiber.

8. The method of claim 7, wherein the reaction mixture comprises SPMF and SA in a ratio of 1:1 to 4:1 (w/w), and wherein the combination of SPMF and SA is present in an amount of about 2% (w/w).

9. The method of claim 7, wherein the $CaCl_2$ aqueous solution comprises 0.5 M $CaCl_2$.

* * * * *